(12) United States Patent
Nudelman et al.

(10) Patent No.: US 7,598,239 B2
(45) Date of Patent: *Oct. 6, 2009

(54) CONJUGATED PSYCHOTROPIC DRUGS AND USES THEREOF

(75) Inventors: Abraham Nudelman, Rechovot (IL); Ada Rephaeli, Herzlia (IL); Irit Gil-Ad, Herzlia (IL); Abraham Weizman, Tel-Aviv (IL)

(73) Assignees: Ramot At Tel Aviv University Ltd., Tel-Aviv (IL); Bar-Ilan University, Ramat-Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/005,342

(22) Filed: Dec. 27, 2007

(65) Prior Publication Data

US 2008/0108606 A1  May 8, 2008

Related U.S. Application Data

(63) Continuation of application No. 10/808,541, filed on Mar. 25, 2004, which is a continuation-in-part of application No. PCT/IL02/00795, filed on Sep. 29, 2002.

(60) Provisional application No. 60/324,936, filed on Sep. 27, 2001.

(51) Int. Cl.
    *A61K 31/54* (2006.01)
    *C07D 417/00* (2006.01)

(52) U.S. Cl. .................................. 514/222.8; 544/44

(58) Field of Classification Search .................. None
     See application file for complete search history.

(56) References Cited

U.S. PATENT DOCUMENTS

| | | | | |
|---|---|---|---|---|
| 2,914,528 | A | * | 11/1959 | Craig ........................... 544/41 |
| 2,944,053 | A | * | 7/1960 | Edgerton ...................... 544/41 |
| 2,989,358 | A | * | 1/1961 | Cusic ........................... 544/45 |
| 3,956,493 | A | | 5/1976 | Yale |
| 3,966,930 | A | | 6/1976 | Buus et al. |
| 4,629,691 | A | | 12/1986 | Collins et al. |
| 5,051,448 | A | | 9/1991 | Shashoua |
| 5,525,727 | A | | 6/1996 | Bodor et al. |
| 5,994,392 | A | | 11/1999 | Shashoua et al. |
| 6,121,325 | A | | 9/2000 | Chen et al. |
| 6,197,764 | B1 | | 3/2001 | Bradley et al. |
| 6,569,853 | B1 | * | 5/2003 | Borisy et al. ............. 514/226.2 |
| 2002/0010208 | A1 | | 1/2002 | Shashoua et al. |
| 2004/0242570 | A1 | | 12/2004 | Nudelman et al. |
| 2006/0058219 | A1 | | 3/2006 | Miller |
| 2006/0142181 | A1 | | 6/2006 | Miller |
| 2007/0099977 | A1 | | 5/2007 | Nudelman et al. |
| 2007/0197514 | A1 | | 8/2007 | Nudelman et al. |

FOREIGN PATENT DOCUMENTS

| | | | |
|---|---|---|---|
| EP | 0361485 | | 4/1990 |
| GB | 829 246 | * | 3/1960 |
| JP | 60-72868 | | 3/1994 |
| WO | WO 97/44063 | | 11/1997 |
| WO | WO 02/28881 | | 4/2002 |
| WO | WO 02/43652 | | 6/2002 |
| WO | WO 03/026563 | | 4/2003 |
| WO | WO 03/061656 | | 7/2003 |
| WO | WO 2005/032474 | | 4/2005 |
| WO | WO 2005/092392 | | 10/2005 |
| WO | WO 2006/027711 | | 3/2006 |
| WO | WO 2008/010222 | | 1/2008 |
| WO | WO 2008/010223 | | 1/2008 |

OTHER PUBLICATIONS

Hadad et al. "Pharmacokinetic Analysis and Antiepileptic Activity of N-Valproyl Derivatives of GABA and Glycine", Pharmaceutical Research, 112(6): 905-910, 1995.

Rephaeli et al. "Observation of Sequence-Dependent Interaction Between Prodrugs of Carboxylic-Acid-Esters and Doxorubicin in Cancer Cells", Proceedings of the American Association for Cancer Research, Annual Meeting, 40: 592-, 1999. Abstract. & 90th Annual Meeting of the American Association for Cancer Research, Philadelphia, PA, USA, 1999.

Scriba et al. "Synthesis and Anticovulsant Activity of N-Benzyloxycarbonyl-Amino Acid Prodrugs of Phenytoin", Journal of Pharmacy and Pharmacology, 51: 549-553, 1999.

Yogev-Falach et al. "The Importance of Propargylamine Moiety in the Anti-Parkinson Drug Rasagiline and Its Derivatives in MAPK-Dependent Amyloid Precursor Protein Processing", The FASEB Journal, 17: 2325-2327, 2003. Abstract.

Zaugg et al. "Modification of Hemoglobin With Analogs of Aspirin", The Journal of Biological Chemistry, 255(7): 2816-2821, 1980.

"New Edition of Pharmaceutics", People's Hygiene Publishing House, 14: 178, 1998. Abstract in Chinese Only!

Budavari et al. "The Merck Index", Merck & Co., USA, 12th Ed., 1996. P.Ther- 8, First col., 6th Line From the Bottom, 2nd col., Line 13.

Budavari et al. "The Merck Index", Merck & Co., USA, 12th Ed, 1996. p. 1260, § 1.

Budavari et al. "The Merck Index", Merck & Co., USA, 12th Ed., 1996. p. 1246, Last §.

Capasso et al. "Anticonvulsive Activity of A New GABA Mimetic Drug", European Neuropsychopharmacology, 7: 57-63, 1997.

Fingl et al. "General Principles", The Pharmacological Basis of Therapeutics, Chap.1: 1-46, 1975.

(Continued)

Primary Examiner—Paul A Zucker

(57) ABSTRACT

Novel chemical conjugates of psychotropic drugs and organic acids, uses thereof in the treatment of psychotic and/or proliferative disorders and diseases and as chemosensitizing agents, and their syntheses are disclosed. The organic acids are selected to reduce side effects induced by the psychotropic drugs and/or to exert an anti-proliferative activity.

8 Claims, 23 Drawing Sheets
(23 of 23 Drawing Sheet(s) Filed in Color)

OTHER PUBLICATIONS

Geyer et al. "Animal Behavior Models of the Mechanisms Underlying Antipsychotic Atypicality", Progress in Neuro-Psychopharmacology & Biological Psychiatry, 27: 1071-1079, 2003.
Köpf-Maier et al. "An Organoid Culture Assay (OCA) for Determining the Drug Sensitivity of human Tumors", Int. J. Cancer, 51: 99-107, 1992.
Lloyd et al. "The Potential Use of GABA Agonists in Psychiatric Disorders: Evidence From Studies With Progabide in Animal Models and Clinical Trials", Pharmacology, Biochemistry & Behavior, 18: 957-966, 1983.
McCaffrey et al. "A Rapid Fluorometric DNA Assay for the Measurement of Cell Density and Proliferation In Vitro", In Vitro Cellular Development Biology, 24(3): 247-252, 1988. Abstract.
Nicoletti et al. "A Rapid and Simple Method for Measuring Thymocyte Apoptosis by Propidium Iodide Staining and Flow Cytometry", Journal of Immunological Methods, 139: 271-279, 1991.
Nordenberg et al. "Effects of Psychotropic Drugs on Cell Proliferation and Differentiation", Biochemical Pharmacology, 58: 1229-1236, 1999.
Pouzet et al. "Effects of the 5-HT7 Receptor Antagonist SB-258741 in Animal Models for Schizophrenia", Pharmacology, Biochemistry and Behavior, 71: 655-665, 2002.
Quadri et al. "Effects of Centrally Acting Drugs on Serum Prolactin Levels in *Rhesus* Monkeys", Neuroendocrinology, 27(3-4): 134-147, 1978. Abstract.
Scriba et al "Anticonvulsant Activity of Phenytoin-Lipid Conjugates, A New Class of Phenytoin Prodrugs"—Journal of Pharmaceutical Pharmacology, 47: 197-203, 1996. Scheme 1, p. 198, Abstract.
Scriba et al. "Synthesis and Anticovulsant Activity of N-Benzyloxycarbonyl-Amino Acid Prodrugs of Phenytoin", Journal of Pharmacy and Pharmacology, 51: 549-533, 1999.
Shalitin et al. "The Effect of Angiotensin II on Myosin Heavy Chain Expression in Cultured Myocardial Cells", In Vitro Cellular Development Biology—Animal, 32: 573-578, 1996.
Toth "A Novel Chemical Approach to Drug Delivery: Lipidic Amino Acid Conjugates", Journal of Drug Targeting, 2(3): 217-239, 1994. p. 223, col. II, 3rd §.
Wolffe "Transcriptional Control. Sinful Repression", Nature, 387: 16017, 1997.
Worms et al. "Dopamine-Like Activities of an Aminopyridazinde Derivative, CM 30366: A Behavioural Study", Naunyn-Schmiedeberg's Archives of Pharmacology, 334: 246-252, 1986.
Official Action Dated Sep. 16, 2008 From the US Patent Office Re.: U.S. Appl. No. 12/005,342.
Examiner's Report Dated May 2, 2007 From the Australian Government Re.: Application No. 2004201240.
Official Action Dated Sep. 9, 2005 From the Patent Office of the People's Republic of China Re.: Application No. 02823600.9 and Its Translation Into English.
Communication Under Rule 112 EPC Dated Oct. 2, 2007 From the European Patent Office Re.: Application No. 05718914.4.
Communication Pursuant to Article 96(2) EPC Dated Nov. 24, 2006 From the European Patent Office Re.: Application No. 02772790.8.
Examiner's Report Dated May 23, 2007 From the Government of India Patent Office Re.: Application No. 642/CHENP/2004-SPS.
Official Action Dated Feb. 14, 2008 From the Government of India Patent Office Re.: Application No. 642/CHENP/2004-SPS.
Official Action Dated May 15, 2008 From the Government of India Patent Office Re.: Application No. 642/CHENP/2004-SPS.
International Search Report Dated Aug. 23, 2006 From the International Searching Authority Re.: Application No. PCT/IL2005/000341.
Written Opinion Dated Aug. 23, 2006 From the International Searching Authority Re.: Application No. PCT/IL2005/000341.
Partial International Search Report Jun. 13, 2006 From the International Searching Authority Re.: Application No. PCT/IL2005/000341.
International Preliminary Examination Report Dated Oct. 12, 2006 From the International Searching Authority By Patent Cooperation Treaty Re.: Application No. PCT/IL2005/000341.
Office Action Dated Jul. 25, 2006 From the US Patent and Trademark Office Re.: U.S. Appl. No. 10/808,541.
Office Action Dated Feb. 1, 2007 From the US Patent and Trademark Office Re.: U.S. Appl. No. 10/808,541.
Office Action Dated Mar. 30, 2006 From the US Patent and Trademark Office Re.: U.S. Appl. No. 10/808,541.
Notice of Allowance Dated Mar. 11, 2008 From the US Patent And Trademark Office Re.: U.S. Appl. No. 10/808,541.
International Search Report Dated Feb. 13, 2008 From the International Searching Authority Re.: Application No. PCT/IL2007/000902.
Written Opinion Dated Feb. 13, 2008 From the International Searching Authority Re.: Application No. PCT/IL2007/000902.
Partial International Search Report Dated Nov. 20, 2007 From the International Searching Authority Re.: Application No. PCT/IL2007/000902.
International Search Report Dated Feb. 12, 2008 From the International Searching Authority Re.: Application No. PCT/IL2007/000903.
Written Opinion Dated Feb. 12, 2008 From the International Searching Authority Re.: Application No. PCT/IL2007/000903.
Partial International Search Report Dated Nov. 27, 2007 From the International Searching Authority Re.: Application No. PCT/IL2007/000903.
Office Action Dated Jun. 19, 2008 From the US Patent and Trademark Office Re.: U.S. Appl. No. 11/636,599.
Office Action Dated May 9, 2008 From the US Patent and Trademark Office Re.: U.S. Appl. No. 11/636,599.
Office Acttion Dated May 16, 2008 From the US Patent and Trademark Office Re.: U.S. Appl. No. 11/636,594.
Office Action Dated Apr. 17, 2008 From the US Patent and Trademark Office Re.: U.S. Appl. No. 11/636,594.
Supplementary European Search Report Dated Apr. 25, 2006 From the European Patent Office Re.: Application No. 02772790.8.
International Search Report Dated Jul. 11, 2003 From the International Searching Authority Re.: Application No. PCT/IL02/00795.

\* cited by examiner

CONJUGATED PSYCHOTROPIC DRUGS AND USES THEREOF

RELATED APPLICATIONS

This is a continuation of U.S. patent application Ser. No. 10/808,541 filed on Mar. 25, 2004 which is a continuation-in-part of PCT International Application No. PCT/IL02/00795, filed on Sep. 29, 2002, which claims the benefit of priority from U.S. Provisional Patent Application No. 60/324,936, filed on Sep. 27, 2001.

FIELD AND BACKGROUND OF THE INVENTION

The present invention relates to novel chemical conjugates of psychotropic drugs and organic acids, and uses thereof. More particularly, the present invention relates to novel chemical conjugates of psychotropic drugs (which may also have anti-proliferative activity and/or chemosensitization activity), and organic acids selected so as to reduce side effects induced by the psychotropic drugs and/or so as to exert an anti-proliferative activity, and uses thereof in the treatment of psychotropic and/or proliferative disorders and diseases and in chemosensitization. The novel chemical conjugates of the present invention are characterized by minimized adverse side effects as compared to prior art psychotropic drugs.

Psychotropic drugs are pharmacological agents that act mainly in the central nervous system (CNS) by modulating neuronal signals transduction. Psychotropic drugs are therefore known, and are referred to herein, as pharmacological agents that exert an activity in the CNS to thereby treat a CNS associated impairment, and include, for example, anti-psychotic drugs, anti-depressants, anti-convulsants, anxiolytics, inhibitors of brain derived enzymes and the like.

Unfortunately, the administration of psychotropic drugs is typically associated with adverse side effects, such as seizures, headaches, fatigue, hyperactivity, dizziness, and many more, which severely limit their use. A comprehensive list of such side effects can be found, for example, in "The Merck Manual of Medical Information" (Merck & Co. Inc.).

Neuroleptic drugs, for example, which are also known as neuroleptic agents or neuroleptics, are classical anti-psychotic drugs that are widely used in the treatment of central nervous system psychotic diseases and disorders, such as schizophrenia. The anti-psychotic efficacy of neuroleptics is attributed to their ability to antagonize/block central dopamine receptors. The neuroleptic drugs are known as typical anti-psychotic drugs and include, for example, phenothiazines, amongst which are aliphatics (e.g., chlorpromazine), piperidines (e.g., thioridazine) and piperazines (e.g., fluphenazine); butyrophenones (e.g., haloperidol); thioxanthenes (e.g., flupenthixol); oxoindoles (e.g., molindone); dibenzoxazepines (e.g., loxapine) and diphenylpiperidines (e.g., pimozide).

However, the administration of currently available neuroleptic drugs is frequently associated with adverse side effects. It is well known in the art that neuroleptic agents induce extrapyramidal symptoms, which include rigidity, tremor, bradykinesia (slow movement), and bradyphrenia (slow thought), as well as tardive dyskinesia, acute dystonic reactions and akathasia. In fact, about 5% of patients that are treated with chronic therapy of neuroleptic drugs for over a year develop pathology of tardive dyskinesia.

A different class of anti-psychotic drugs includes the atypical anti-psychotics. Atypical anti-psychotic drugs have a receptor binding profile that includes binding to central serotonin 2 receptors (5-HT2) in addition to dopamine D2 receptors. Atypical anti-psychotic drugs include, for example, closeting, olanzapine and risperidone, and are generally characterized by high anti-serotonin activity and relatively low affinity to dopamine D2 receptors. Some atypical anti-psychotic drugs, such as clozapine, are known to further antagonize adherenic, cholinergic and histaminergic receptors.

Unlike the neuroleptics, atypical anti-psychotics cause minimal extrapyramidal symptoms and thus rarely cause tardive dyskinesias, akathasia or acute dystonic reactions. However, the administration thereof involves other side effects such as increase of body weight, mood disturbances, sexual disfunction, sedation, orthostatic hypotension, hypersalivation, lowered seizure threshold and, in particular, agranulocytosis.

The sever side effects that are associated with both typical and atypical anti-psychotic drugs, also referred to herein as anti-psychotics, establish a major limitation to their use and extensive efforts have been made to develop anti-psychotic drugs devoid of these side effects.

U.S. Pat. No. 6,197,764 discloses chemical conjugates of clozapine (an atypical anti-psychotic drug) and a fatty acid of 12-26 carbon atoms, preferably 16-22 carbon atoms. These conjugates are characterized by extended therapeutic effectiveness, which permits administration of lower doses thereof to yield an anti-psychotic therapeutic effect and thereby reduce the chances of developing serious side effects. Hence these conjugates are beneficial and advantageous over non-conjugated atypical anti-psychotic drugs. However, U.S. Pat. No. 6,197,764 fails to disclose such advantageous conjugates that include other anti-psychotic agents and is further limited to conjugates including long-chain fatty acids. It should be mentioned that ester conjugates of other anti-psychotics, mainly neuroleptics, and long-chain fatty acids are well known in the art. Nevertheless, such conjugates are aimed mainly at facilitating the brain penetration of the drug and are not designed to actively reduce or prevent side effects.

U.S. Pat. No. 3,966,930 discloses fluoro-substituted phenothiazine derivatives that have pronounced neuroleptic properties and a relatively low degree of undesired side effects. However, while some of the claimed fluoro-substituted phenothiazine derivatives of U.S. Pat. No. 3,966,930 include an acyl radical that has 1-17 carbon atoms in its chain, the experimental data is limited to phenothiazine derivatives that include only acyl radicals derived from either oxalic acid or maleic acid (i.e., organic acids that include 2 and 4 carbon atoms, respectively). The disclosed phenothiazine derivatives have longer therapeutic effect as compared to other known neuroleptics and are therefore characterized by a relatively low degree of induced side effects. The prolonged therapeutic effect of these compounds is mainly attributed to the phenothiazine substituents (e.g., fluoro and trifluoromethyl) while their conjugation with the organic acids is aimed chiefly at facilitating their pharmaceutical formulation.

Recent studies on the development of extrapyramidal symptoms as a result of treatment with psychotropic drugs, mainly neuroleptics, have suggested a mechanism that involves an imbalance in the dopaminergic receptors D1 and D2, which is further accompanied by decreased activity of the γ-aminobutyric acid (GABA) system in the brain.

GABA is an important inhibitory neurotransmitter in the brain, which is known to affect mood stabilizing activity, anxiolytic activity and muscle relaxant activity, and is further known to be related to some central nervous system disorders and diseases. The recent studies on extrapyramidal symptoms suggest that GABA agonists may be further used to reduce neuroleptic-induced side effects and thus have an additional therapeutic potential.

Previous studies have already suggested that GABA agonists can interfere with other brain neurotransmitters and, in particular, with the dopamine system. Thus, it was found that GABA agonists can antagonize the neuroleptic-induced increase of dopamine receptors sensitivity and are therefore capable of improving neuroleptic-induced dyskinesia [1]. Furthermore, it was found that some known direct GABA agonists (e.g., muscimol and SL 76002) cause a biphasic effect on haloperidol-induced catalepsy, such that while low doses of the agonist inhibit the stereotypic catalepsy behavior, high doses of the agonist potentiate the haloperidol-induced catalepsy. Other studies have reported that GABA agonists further induce anti-convulsive activity [2].

The use of GABA agonists is limited since they include hydrophilic functional groups (e.g., a free carboxylic acid group and a free amino group) and therefore do not readily cross the blood brain barrier (BBB). However, it was found that chemical conjugation of such compounds with fatty amino acids or peptides could substantially facilitate their passage across the blood brain barrier (BBB) [3].

Indeed, U.S. Pat. Nos. 3,947,579; 3,978,216; 4,084,000; 4,129,652 and 4,138,484 disclose that GABA-like compounds (compounds that are pharmacologically related to GABA) which are known to cross the blood brain barrier, such as γ-hydroxybutyrolactone, γ-hydroxybutyrate, aminooxyacetic acid, 5-ethyl-5-phenyl-2-pyrrolidone, 1-hydroxy-3-amino-2-pyrrolidone and β-(4-chlorophenyl)-γ-aminobutyric acid, when co-administered with neuroleptic drugs, allow the use of somewhat lower doses of neuroleptic drugs to obtain the same anti-psychotic effect as obtained with higher doses of neuroleptic drug without administering these GABA-like compounds and, at the same time, somewhat reduce extrapyramidal side effects. The same anti-psychotic effect is said to be obtained although lower doses of neuroleptic drugs are used because the GABA-like compounds are said to potentiate anti-psychotic activity of the co-administered anti-psychotic drug.

Recent studies revealed that some psychotropic drugs and, in particular, the phenothiazines, further exert a potent anti-proliferative activity in different cell lines, such as neuronal cells, glial cells, melanoma cells, breast cells, colon cells, prostate cells, lymphoma and leukemia, as well as in primary human keratocytes [4]. The "new half mustard type phenothiazines", which is known to exert a specific inhibitory effect on calmodulin, were tested by the National Cancer Institute (NCI). The anti-proliferative activity of the phenothiazines was observed in the in vitro screen of 60 different human cancer cell lines. Some phenothiazines further showed significant inhibition of tumor growth in animal models. These findings are consistent with the low frequency of cancer occurrence in schizophrenic patients on neuroleptic medication, as compared with the general population.

WO 02/43652, which is incorporated by reference as if fully set forth herein, teaches the use of various typical and atypical psychotropic agents in the treatment of proliferative diseases. In particular, WO 02/43652 teaches that cyclic psychotropic agents (e.g., tricyclic, bicyclic and monocyclic) can serve as effective agents in the treatment of numerous tumors, including glioma, melanoma, neuroblastoma, colon, lung and prostate cancers, as well as in the treatment of multi drug resistant (MDR) cancer cells, such as B16 melanoma cells (known to be resistant to doxorubicin and colchicine) and Neuroblastoma (SH-SY5T, resistant to 5-FU and doxorubicin). Moreover, apart from teaching the activity of psychotropic agents in the treatment of MDR cancer, WO 02/43652 further teaches the use of the psychotropic drugs as chemosensitizers, namely, as compounds that effectively sensitize cancer cells, particularly MDR cancer cells, to cytotoxic drugs.

However, although the teachings of WO 02/43652 are highly advantageous, particularly with respect to the anti-proliferative and chemosensitization activity of psychotropic agents in the treatment of MDR cancer, the use of these psychotropic agents is highly limited by the adverse side effects induced thereby.

Butyric acid (BA) and 4-phenylbutyric acid (PBA), of which GABA is a derivative, are also known to act as differentiating and anti-proliferative agents in a wide spectrum of neoplastic cells in vitro [5]. Both the butyric acid and the 4-phenylbutyric acid are known as pleotropic agents and one of their most notable activities is the reversible increase of the acetylation level in nuclear histones, which leads to chromatin relaxation and changes in transcription activity [6]. It is assumed that this mechanism of action is further related to the anticancer activity of butyric acid and the 4-phenylbutyric acid.

Thus, the prior art teaches the use of psychotropic drugs in the treatment of central nervous system disorders and diseases, as well as in the treatment of proliferative disorders and diseases such as malignant and benign tumors and MDR cancer, as anti-proliferative agents and as chemosensitizers. The prior art further teaches the use of GABA agonists (including GABA itself) as potential agents for reducing neuroleptic-induced side effects as well as the use of butyric acid and derivatives thereof as anti-proliferative agents.

Nevertheless, there is still a widely recognized need for, and it would be highly advantageous to have, psychotropic drugs characterized by improved therapeutic activity and yet reduced side effects, which can also serve as anti-proliferative drugs and as chemosensitizers.

SUMMARY OF THE INVENTION

According to the present invention there are provided (i) chemical conjugates of psychotropic drugs and organic acids selected to reduce the side effects induced by the psychotropic drugs and/or to exert anti-proliferative activity; (ii) chemical conjugates of psychotropic drugs and GABA agonists (including GABA itself); (iii) chemical conjugates of psychotropic drugs and anti-proliferative agents; (vi) methods for their synthesis; (v) use thereof in the treatment and/or prevention of psychotropic disorders and diseases while reducing the side effects characteristic of conventional psychotropic drugs; (v) use thereof in the treatment and/or prevention of proliferative disorders and diseases; and (vi) use thereof as chemosensitizing agents.

It is shown herein that such chemical conjugates of psychotropic drugs are characterized by minimized adverse side effects (e.g., extrapyramidal symptoms), enhanced psychotropic therapeutic activity and anti-proliferative activity and by chemosensitization activity. It is further shown herein that such chemical conjugates unexpectedly provide synergistic effects as compared to their parent compounds both with respect to their therapeutic effects and with respect to the minimization of side effects.

Thus, according to one aspect of the present invention there is provided a chemical conjugate comprising a first chemical moiety covalently linked to a second chemical moiety, wherein the first chemical moiety is a psychotropic drug residue and further wherein the second chemical moiety is an organic acid residue that is selected so as to reduce side effects induced by the psychotropic drug when the psychotropic drug is administered per se and/or to exert anti-proliferative activity.

According to another aspect of the present invention there is provided a pharmaceutical composition comprising, as an active ingredient, the chemical conjugate of the present invention and a pharmaceutically acceptable carrier.

The pharmaceutical composition of the present invention is preferably packaged in a packaging material and is identified in print, on or in the packaging material, for use in the treatment of a psychotropic disorder or disease, for use in the treatment of a proliferative disorder or disease and/or for use in chemosensitization, in combination with a chemotherapeutic agent and/or in a medical condition for which chemosensitization is beneficial.

According to yet another aspect of the present invention there is provided a method of treating or preventing a psychotropic disorder or disease in a subject, the method comprising administering to the subject a therapeutically effective amount of the chemical conjugate of the present invention.

According to further features in preferred embodiments of the invention described below, the psychotropic disorder or disease is selected from the group consisting of a psychotic disorder or disease, an anxiety disorder, a dissociative disorder, a personality disorder, a mood disorder, an affective disorder, a neurodegenerative disease or disorder, a convulsive disorder, a boarder line disorder and a mental disease or disorder.

According to still further features in the described preferred embodiments the psychotropic disorder or disease is selected from the group consisting of schizophrenia, paranoia, childhood psychoses, Huntington's disease, Gilles de la Tourette's syndrome, depression, manic depression, anxiety, Parkinson disease, Alzheimer disease and epilepsy.

According to still another aspect of the present invention there is provided a method of treating or preventing a proliferative disorder or disease in a subject, the method comprising administering to the subject a therapeutically effective amount of the chemical conjugate of the present invention.

According to further features in preferred embodiments of the invention described below, the proliferative disorder or disease is selected from the group consisting of a brain tumor, a brain metastase and a peripheral tumor.

According to still further features in the described preferred embodiments the proliferative disorder is cancer, such as multidrug resistant cancer.

According to an additional aspect of the present invention, there is provided a method of chemosensitization. The method comprises administering to a subject in need thereof a chemotherapeutically effective amount of one or more chemotherapeutic agent(s) and a chemosensitizing effective amount of the chemical conjugate of the present invention.

According to further features in preferred embodiments of the invention described below, the subject has cancer such as multidrug resistant cancer.

According to further features in preferred embodiments of the invention described below, the second chemical moiety is covalently linked to the first chemical moiety via an ester bond selected from the group consisting of a carboxylic ester bond, an alkyoxy carboxylic ester bond, an amide bond and a thioester bond.

According to still further features in the described preferred embodiments the second chemical moiety is selected from the group consisting of an anti-proliferative agent residue, an analgesic residue and a GABA agonist residue.

According to still further features in the described preferred embodiments the psychotropic drug has an anti-proliferative activity.

According to still further features in the described preferred embodiments the psychotropic drug has a chemosensitization activity.

According to still further features in the described preferred embodiments the psychotropic drug residue is selected from the group consisting of a phenothiazine residue and a phenothiazine derivative residue.

According to still further features in the described preferred embodiments the psychotropic drug residue is an anti-psychotic drug residue.

According to still further features in the described preferred embodiments the anti-psychotic drug residue is selected from the group consisting of a typical anti-psychotic drug residue and an atypical psychotic drug residue.

According to still further features in the described preferred embodiments the psychotropic drug residue is selected from the group consisting of an anxiolytic drug residue, an anti-depressant residue, an anti-convulsive drug residue, an anti-parkinsonian drug residue, an acetylcholine esterase inhibitor residue, a MAO inhibitor residue, a tricyclic psychotropic drug residue, a bicyclic psychotropic drug residue, a monocyclic psychotropic drug residue, a phenothiazine residue, a benzodiazepine residue and a butyrophenone residue.

According to still further features in the described preferred embodiments the psychotropic drug residue is selected from the group consisting of a chlorpromazine residue, a perphenazine residue, a fluphenazine residue, a zuclopenthixol residue, a thiopropazate residue, a haloperidol residue, a benperidol residue, a bromperidol residue, a droperidol residue, a spiperone residue, a pimozide residue, a piperacetazine residue, an amilsuipride residue, a sulpiride residue, a clothiapine residue, a ziprasidone residue, a remoxipride residue, a sultopride residue, an alizapride residue, a nemonapride residue, a clozapine residue, an olanzapine residue, a ziprasidone residue, a sertindole residue, a quetiapine residue, a fluoxetine residue, a fluvoxamine residue, a desipramine residue, a paroxetine residue, a sertraline residue, a valproic acid residue, a temazepam residue, a flutemazepam residue, a doxefazepam residue, an oxazepam residue, a lorazepam residue, a lormetazepam residue, a cinolazepam residue, a flutazolam residue, a lopirazepam residue, a meprobamate residue, a carisoprodol residue, an acetophenazine residue, a carphenazine residue, a dixyrazine residue, a priciazine residue, a pipothiazine residue, a homophenazine resdiue, a perimetazine residue, a perthipentyl residue, a flupentixol residue, a piflutixol residue, a teflutixol residue, an oxypethepin residue, a trifluperidol residue, a penfluridol residue, a meclobemide residue, a norclomipramine residue, an amoxapine residue, a nortriptyline residue, a protriptyline residue, a reboxetine residue, a tacrine residue, a rasagiline residue, an amatadine residue, a phenobarbital residue and a phenyloin residue.

According to still further features in the described preferred embodiments the GABA agonist residue is selected from the group consisting of a (±) baclofen residue, an γ-aminobutyric acid (GABA) residue, a γ-hydroxybutyric acid residue, an aminooxyacetic acid residue, a β-(4-chlorophenyl)-γ-aminobutyric acid residue, an isonipecotic acid residue, a piperidine-4-sulfonic acid residue, an 3-aminopropylphosphonous acid residue, an 3-aminopropylphosphinic acid residue, an 3-(aminopropyl)methylphosphinic acid residue, a 1-(aminomethyl)cyclohexaneacetic acid residue (gabapentin), a 4-amino-5-hexenoic acid (γ-vinyl GABA, vigabatrin) and an 3-(2-imidazolyl)-4-aminobutanoic acid residue.

According to still further features in the described preferred embodiments the anti-proliferative agent residue is selected from the group consisting of a butyric acid residue and a 4-phenylbutyric acid residue.

According to still further features in the described preferred embodiments the organic acid residue has a general formula —R—C(═O)— wherein, R is selected from the group consisting of a substituted or non-substituted hydrocarbon residue having 1-20 carbon atoms, a substituted or non-substituted hydrocarbon residue having 1-20 carbon atoms and at least one heteroatom selected from the group consisting of oxygen, nitrogen and sulfur and $R_1$, whereas, $R_1$ is a residue of a general formula -Z-C(═O)O—$CHR_2$—$R_3$ wherein, Z is selected from the group consisting of a single bond, a substituted or non-substituted hydrocarbon residue having 1-20 carbon atoms and a substituted or non-substituted hydrocarbon residue having 1-20 carbon atoms and at least one heteroatom selected from the group consisting of oxygen, nitrogen and sulfur; $R_2$ is selected from the group consisting of hydrogen and an alkyl having 1-10 carbon atoms; and $R_3$ is selected form the group consisting of hydrogen, a substituted or non-substituted hydrocarbon residue having 1-20 carbon atoms and a substituted or non-substituted alkyl having 1-20 carbon atoms and at least one heteroatom selected from the group consisting of oxygen, nitrogen and sulfur.

According to still further features in the described preferred embodiments R is a substituted or non-substituted alkyl having 3-5 carbon atoms.

According to still further features in the described preferred embodiments the organic acid residue is selected from the group consisting of a butyric acid residue, a valeric acid residue, a 4-phenylbutyric acid residue, an 4-aminobutyric acid residue, a retinoic acid residue, a sulindac acid residue, an acetyl salicylic acid residue, an ibuprofen residue, a malonic acid residue, a succinic acid residue, a glutaric acid residue, a fumaric acid residue and a phthalic acid residue.

According to a further aspect of the present invention there is provided a method of synthesizing the chemical conjugates of the present invention. The method comprises reacting an organic acid and a psychotropic drug, so as to obtain a residue of the organic acid covalently linked to a residue of the psychotropic drug.

According to further features in preferred embodiments of the invention described below, the residue of the organic acid is covalently linked to the residue of the psychotropic drug via a carboxylic ester bond, and the method further comprising, prior to the reacting, converting the organic acid into an acyl chloride derivative thereof.

According to still further features in the described preferred embodiments the residue of the organic acid is covalently linked to the residue of the psychotropic drug via a thioester bond, and the method further comprising, prior to the reacting, converting the organic acid into an acyl chloride derivative thereof and converting the psychotropic drug into a thiol derivative thereof.

According to still further features in the described preferred embodiments the residue of the organic acid is covalently linked to the residue of the psychotropic drug via an amide bond, and the method further comprising, prior to the reacting, converting the organic acid into an acyl chloride derivative thereof and converting the psychotropic drug into an amine derivative thereof.

According to still further features in the described preferred embodiments the residue of the organic acid is covalently linked to the residue of the psychotropic drug via an alkyloxy carboxylic ester bond and the method further comprising, prior to the reacting, converting the psychotropic drug into a chloroalkyl ester derivative thereof.

The organic acid and the psychotropic drug used in the method described above are preferably derived from the organic acid residue and the psychotropic drug residue of the present invention, described hereinabove.

In cases where the organic acid is a GABA agonist that comprises a free amino group, the method further comprising protecting the free amino group with a protecting group, prior to the reacting, so as to obtain by the reacting an amino-protected residue of the organic acid covalently linked to the residue of the psychotropic drug, and removing the protecting group after obtaining the amino-protected residue of the organic acid covalently linked to the residue of the psychotropic drug. Preferably, the method further comprises, after the protecting and prior to the reacting, converting the organic acid into an acyl imidazole derivative thereof.

The present invention successfully addresses the shortcomings of the presently known configurations by providing new and potent chemical conjugates of psychotropic drugs that induce minimized adverse side effects for the treatment and prevention of psychotropic and/or proliferative disorders and diseases and for use as chemosensitizers.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
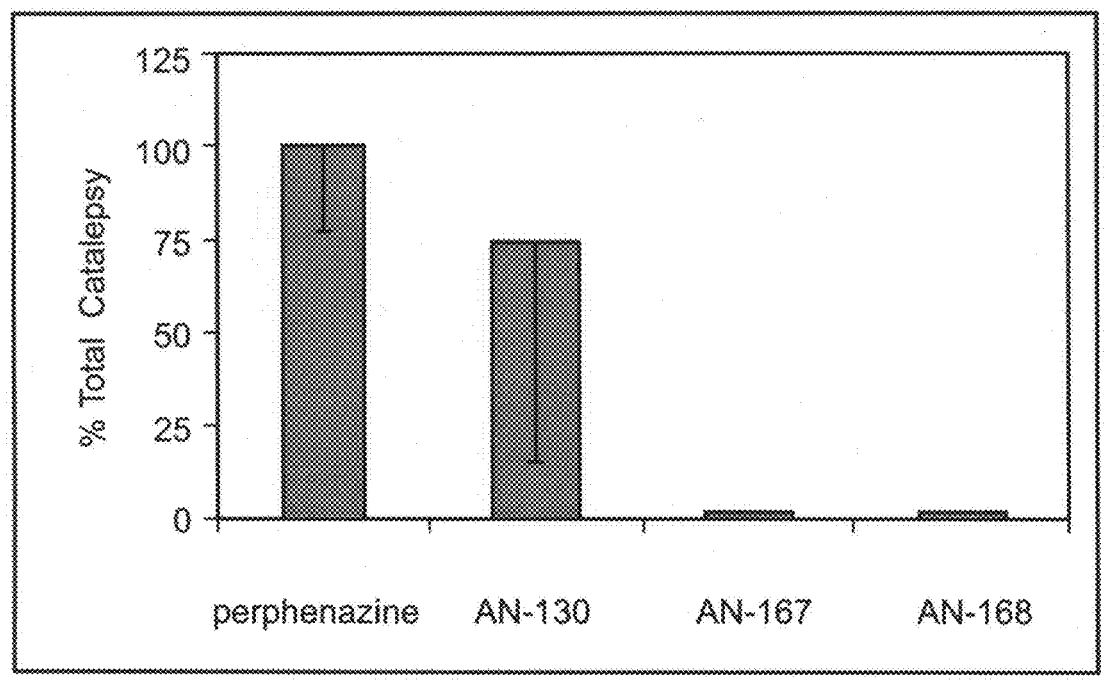
Figure 1B:
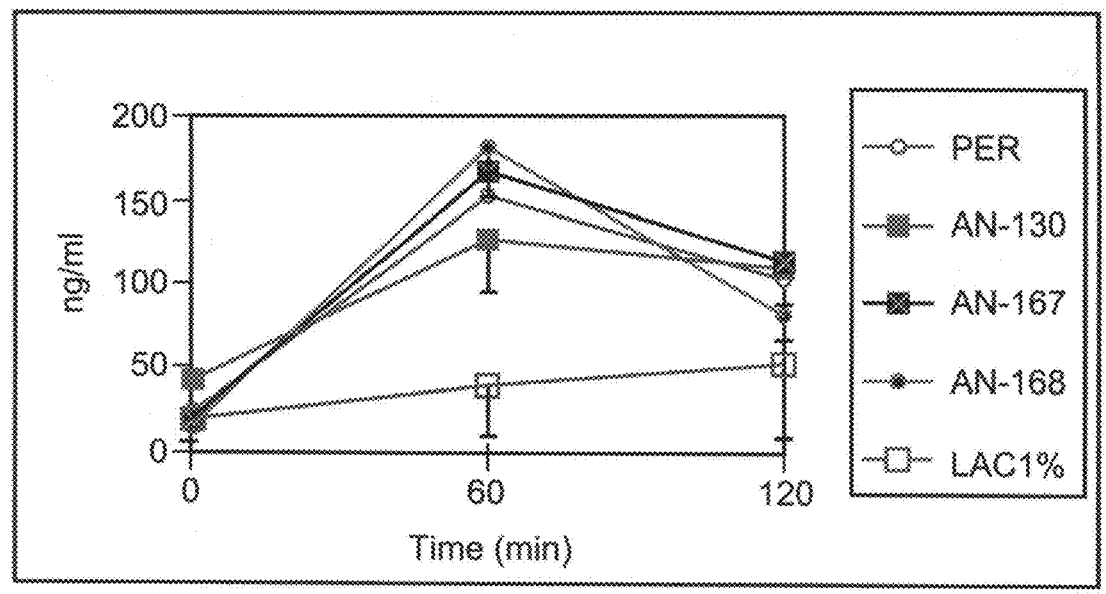
Figure 2:
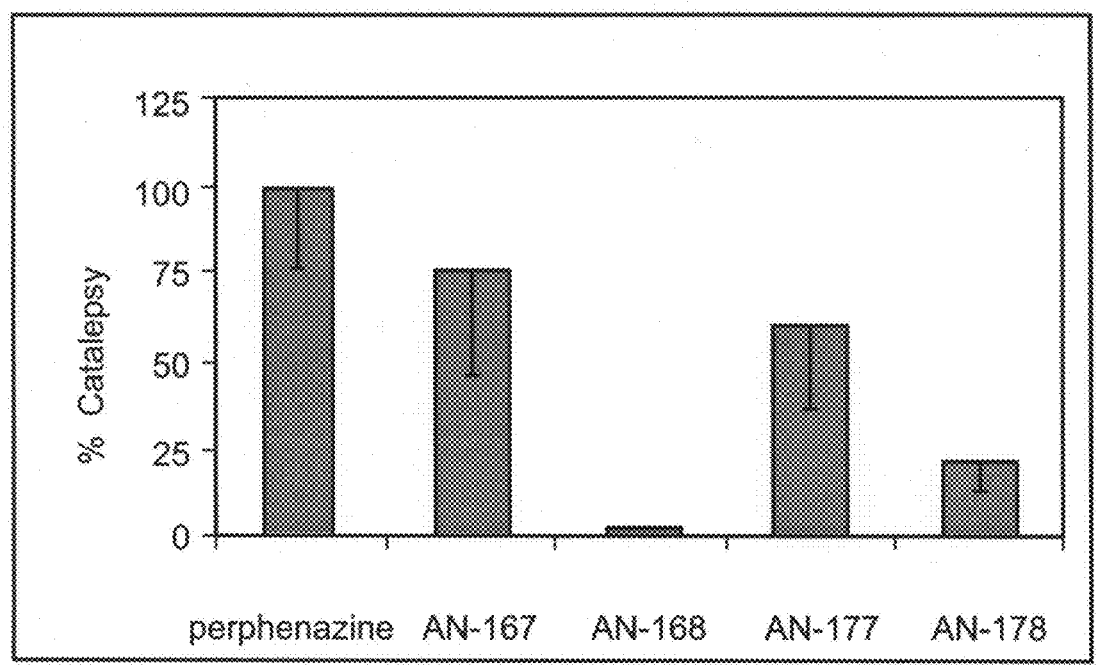
Figure 3A:
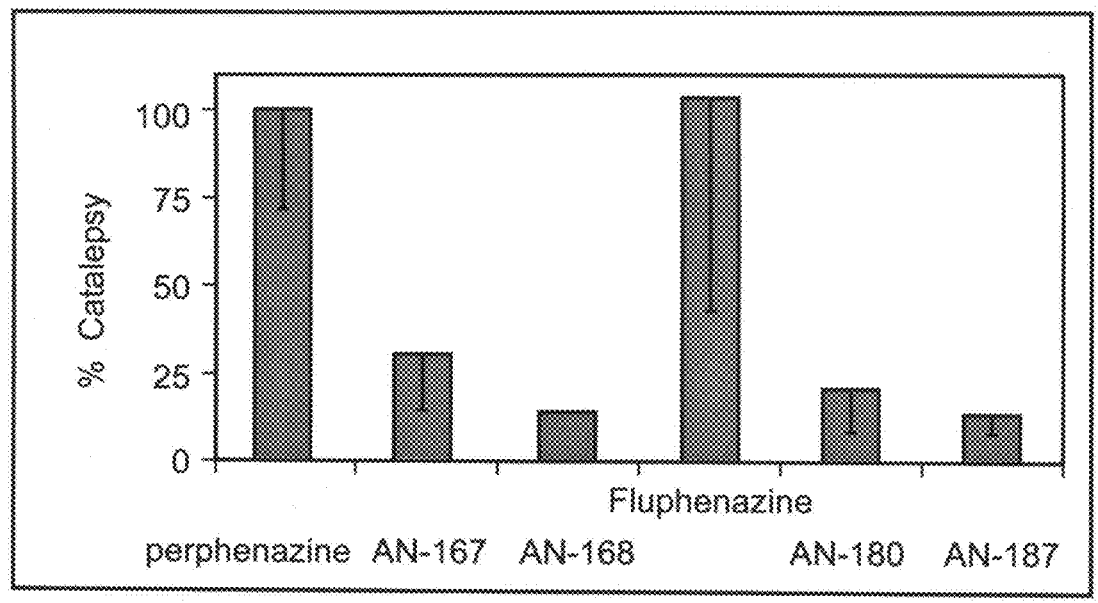
Figure 3B:
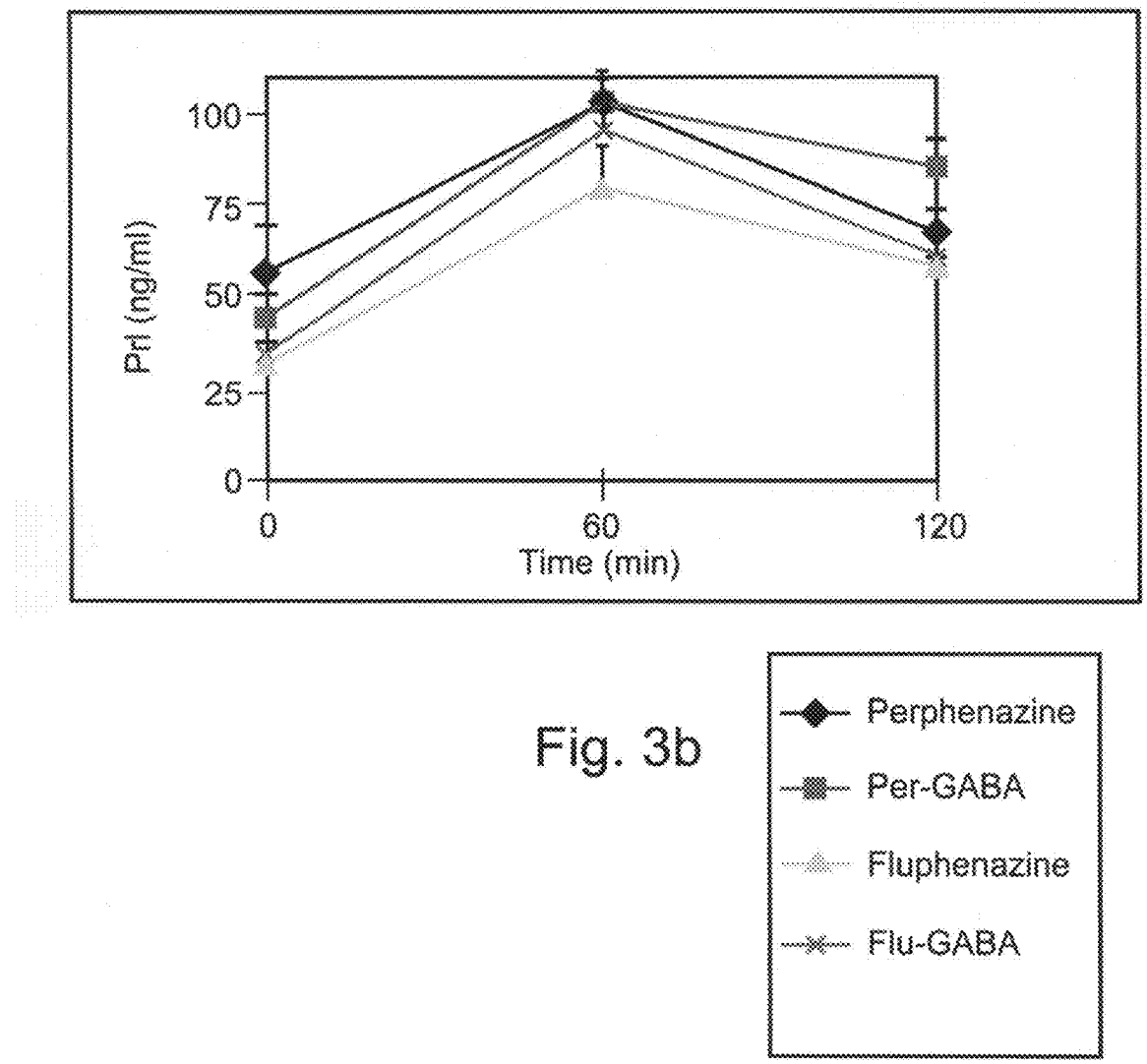
Figure 4A:
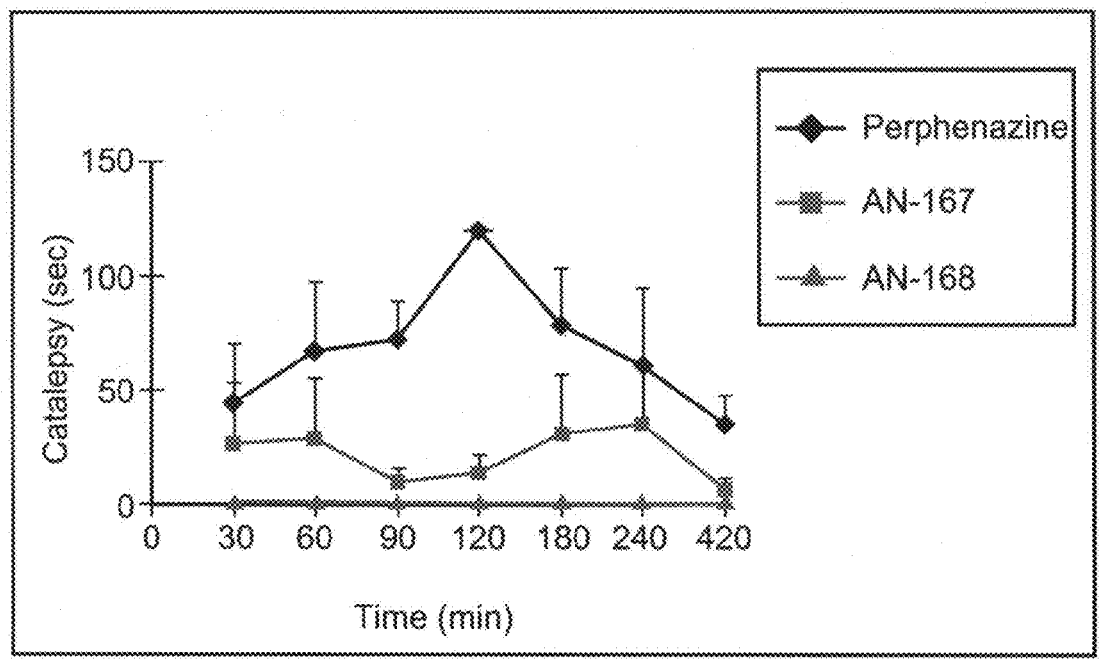
Figure 4B:
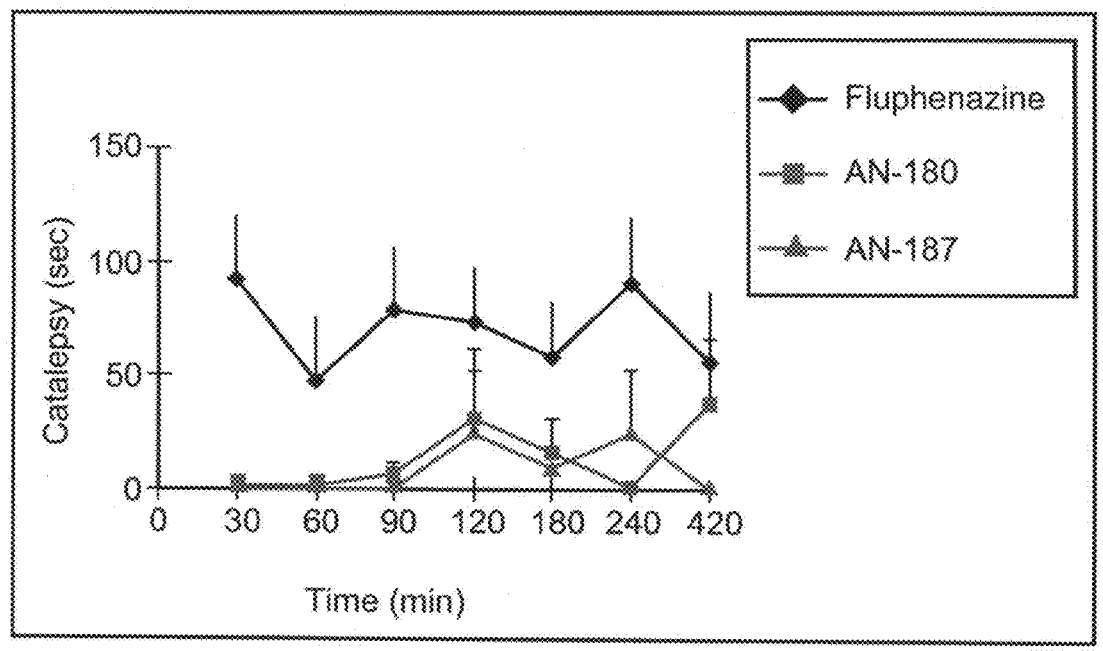
Figure 5A:
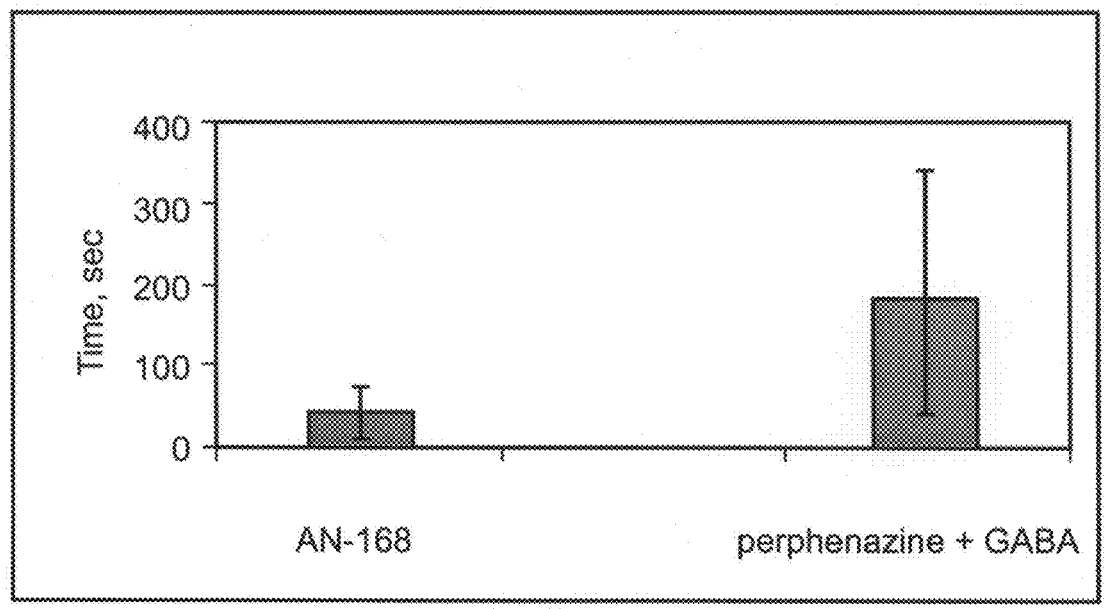
Figure 5B:
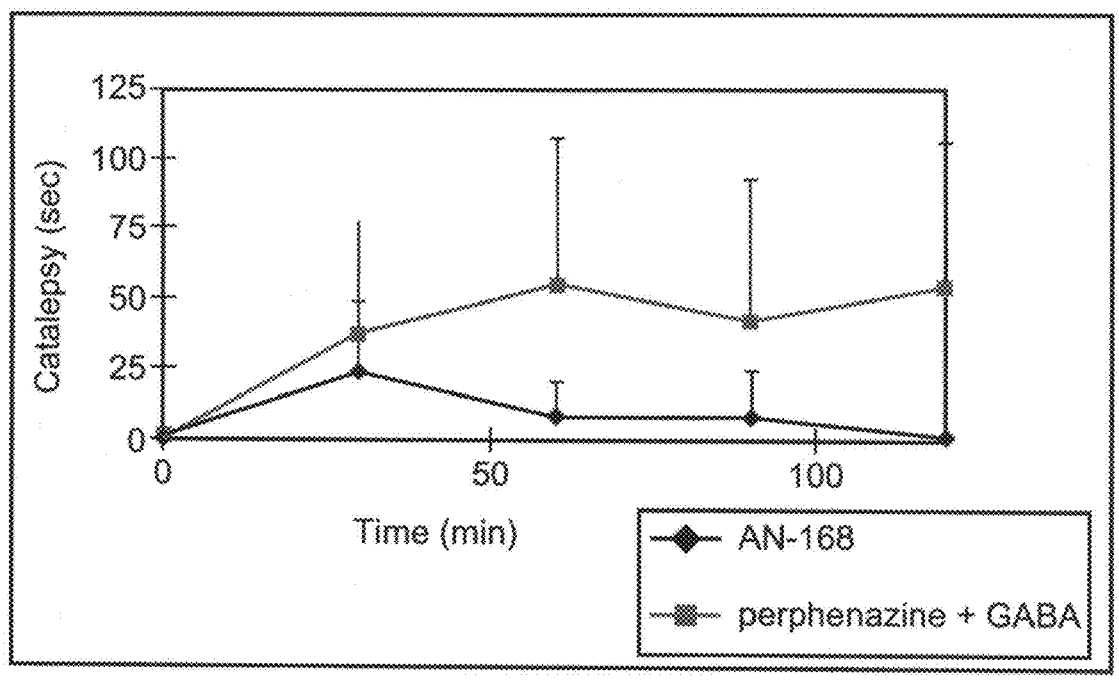
Figure 6:
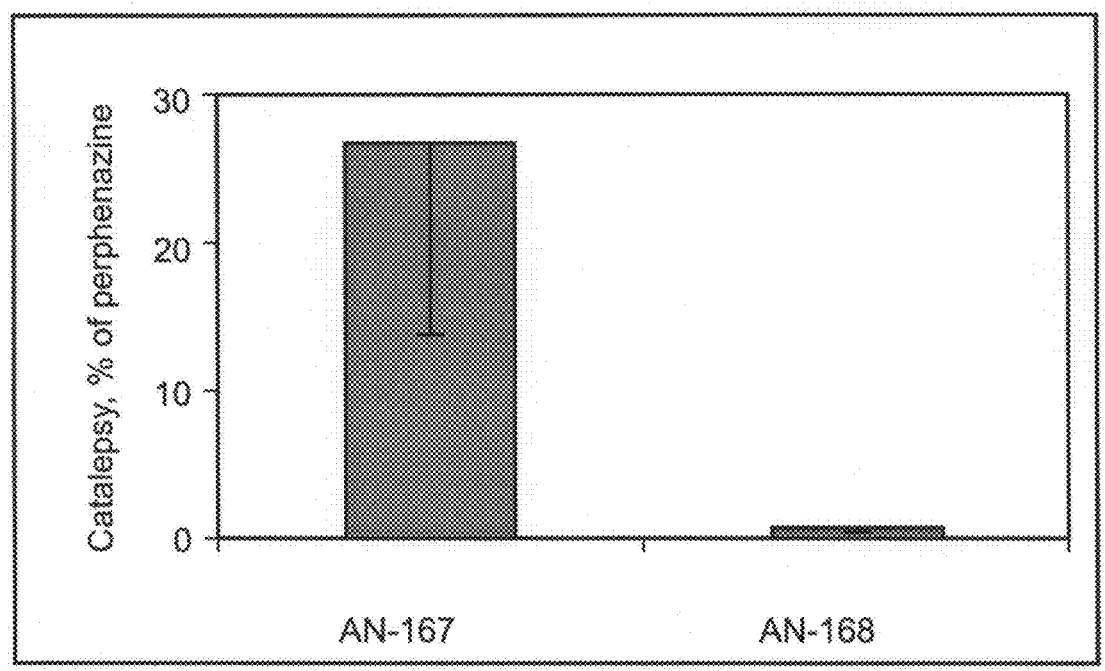
Figure 7A:
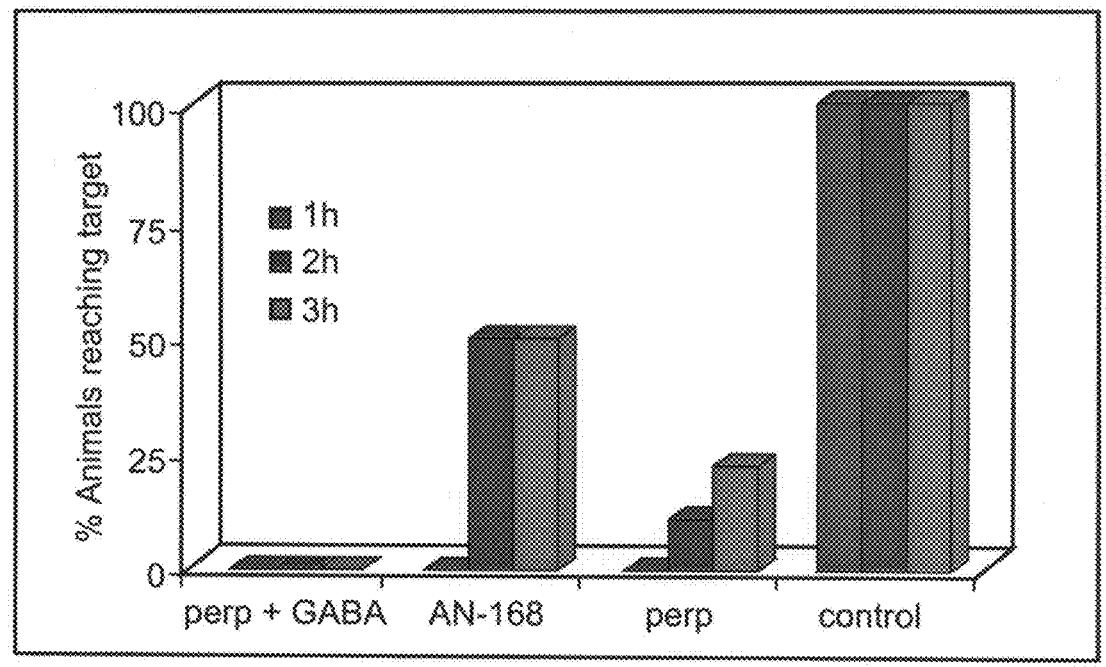
Figure 7B:
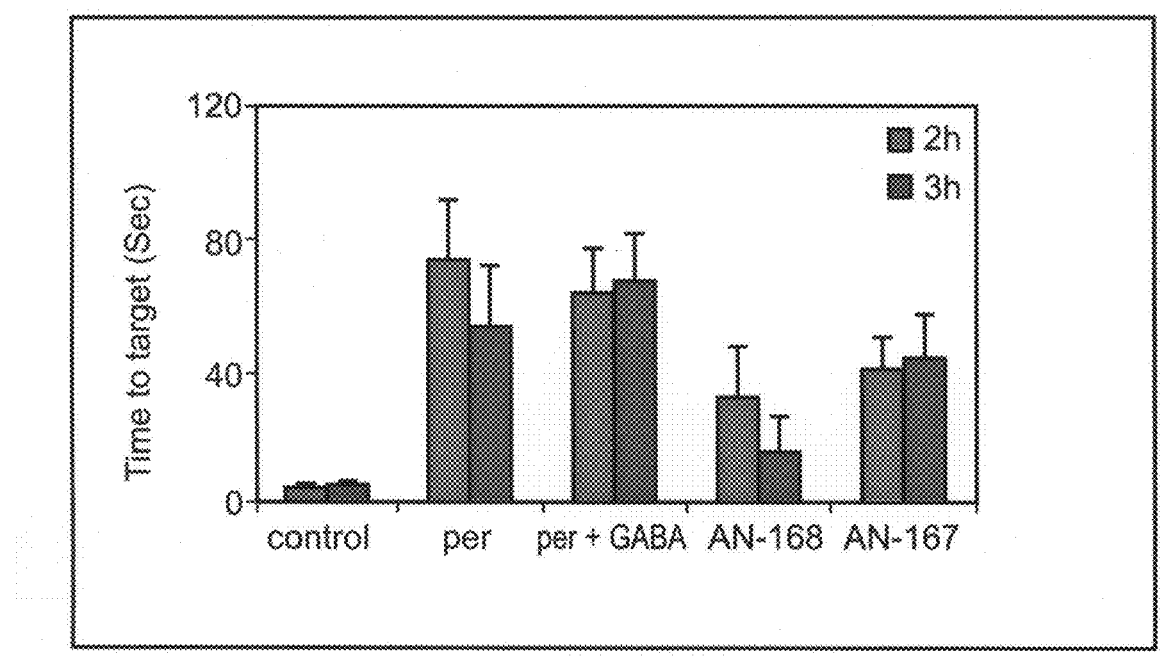
Figure 8A:
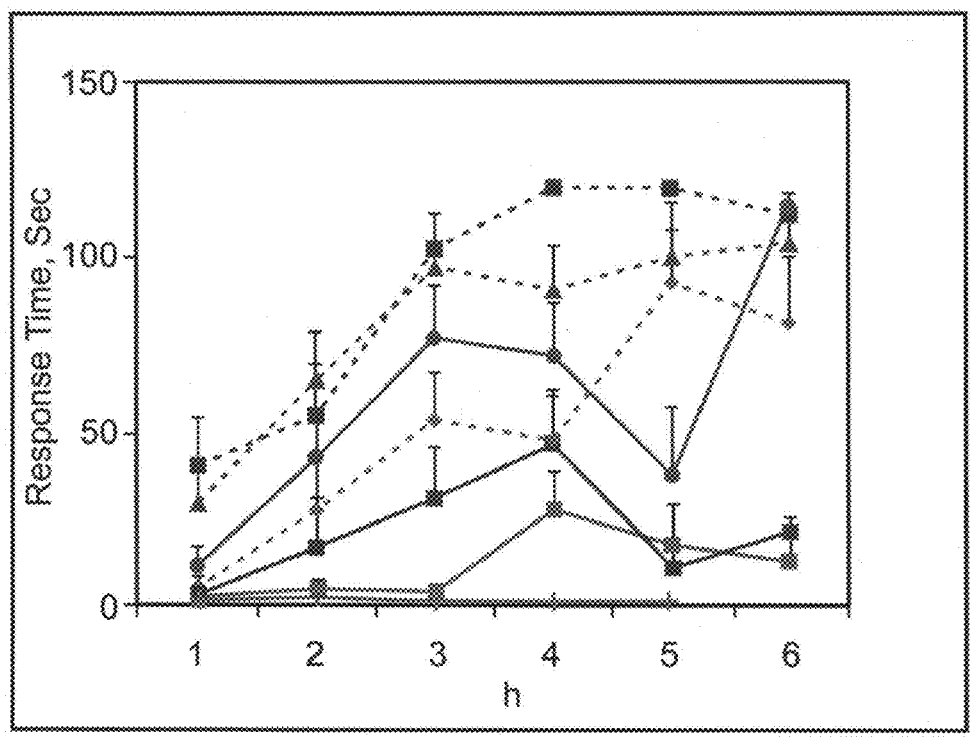
Figure 8B:
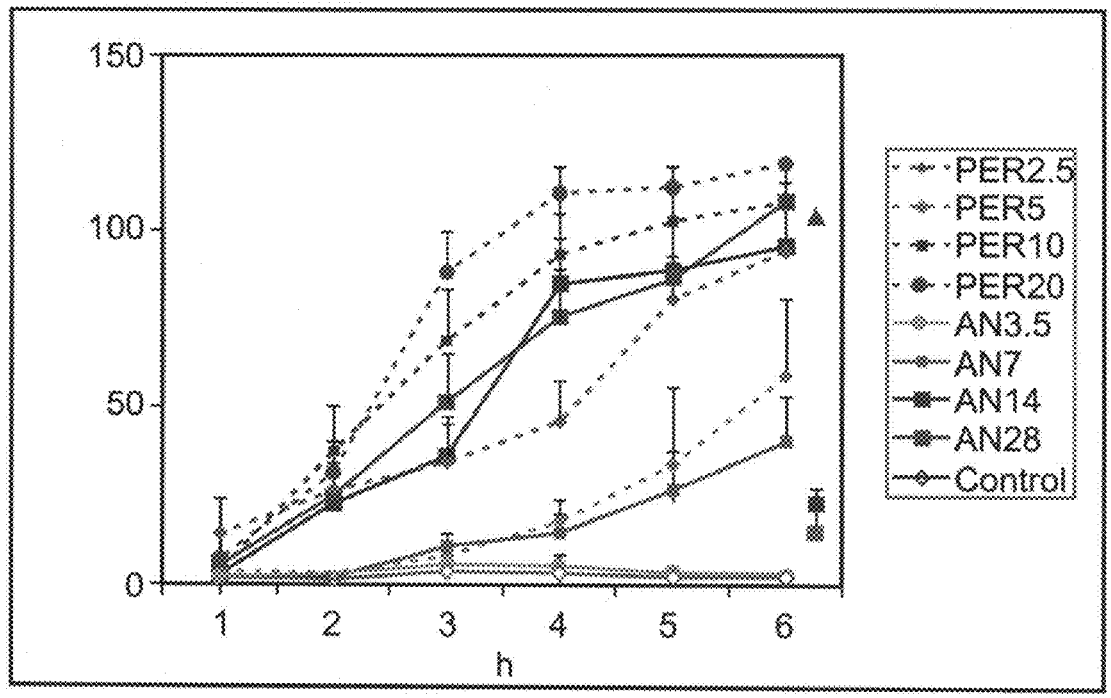
Figure 9A:
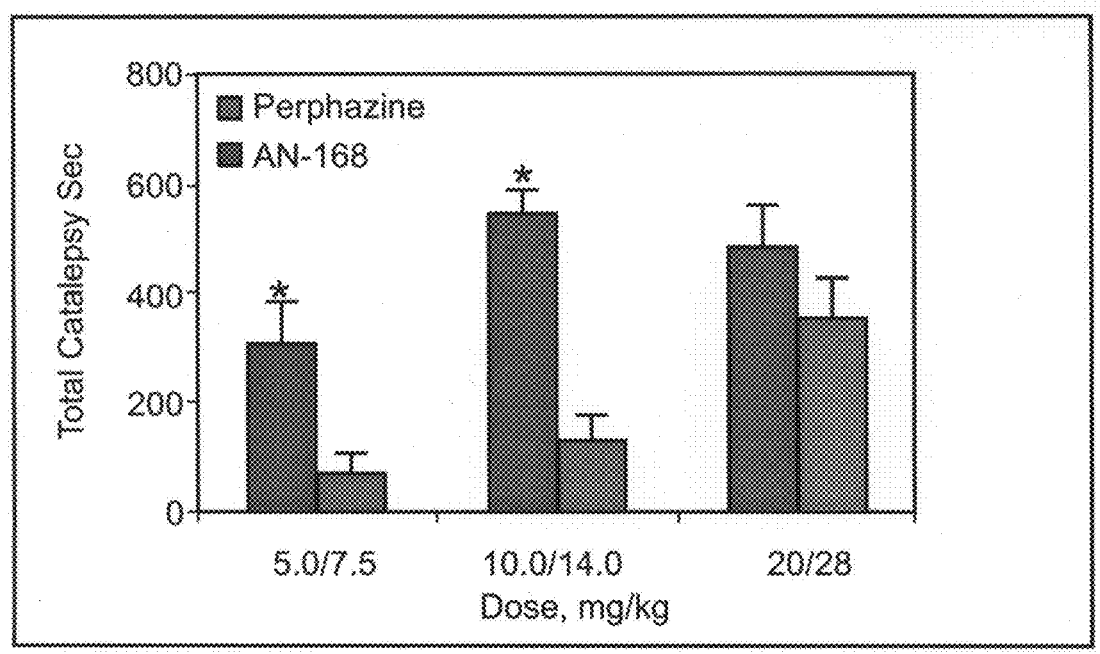
Figure 9B:
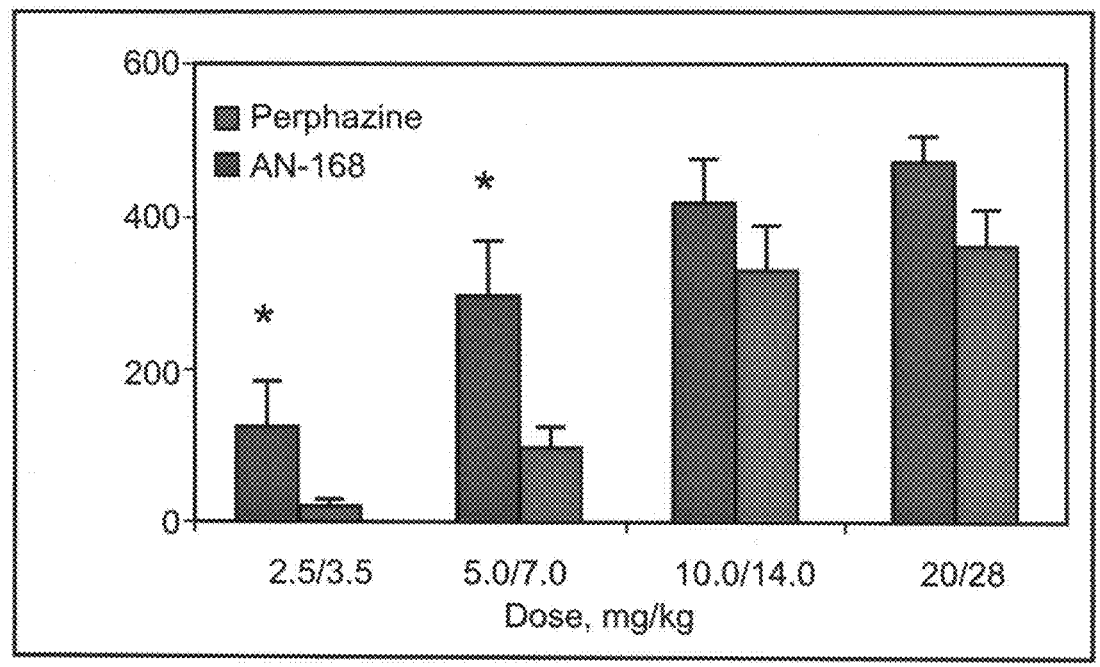
Figure 10A:
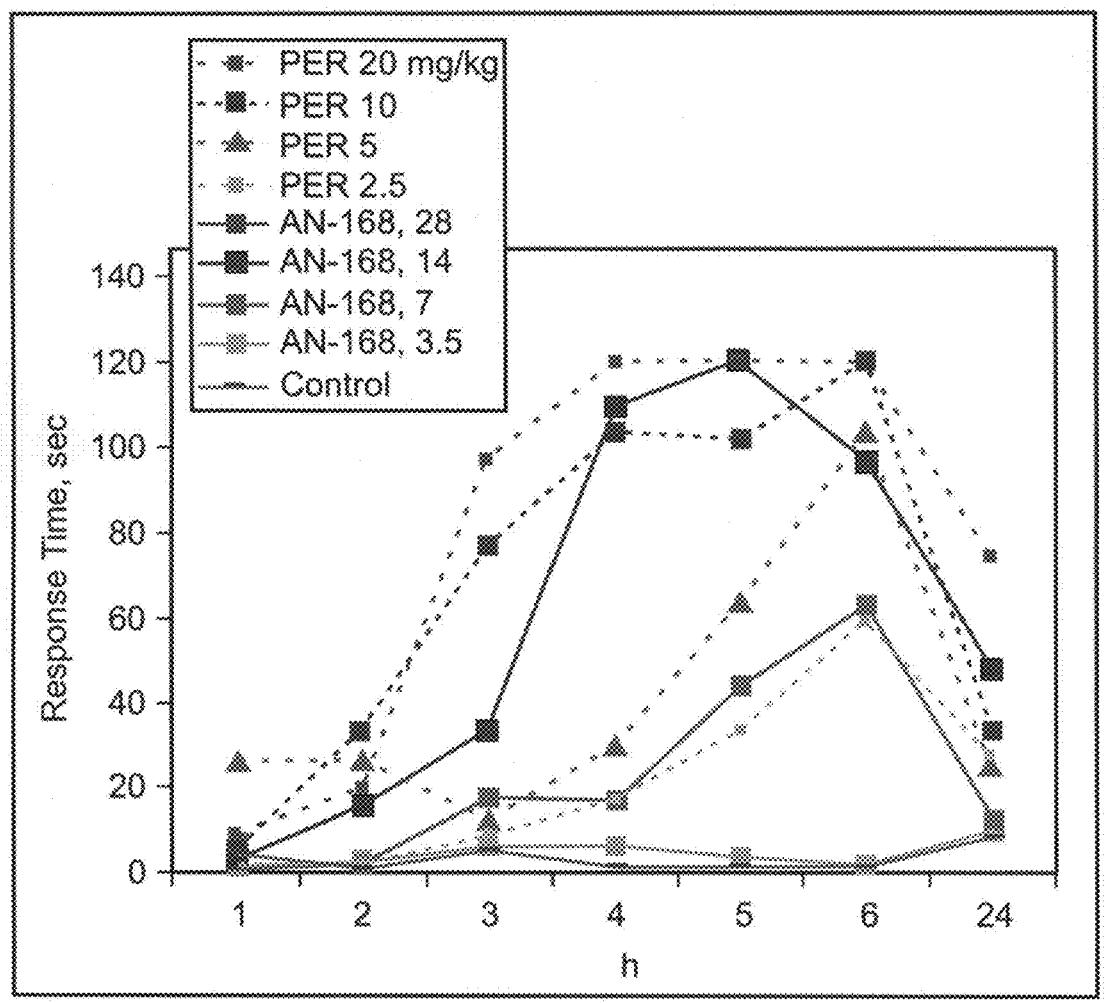
Figure 10B:
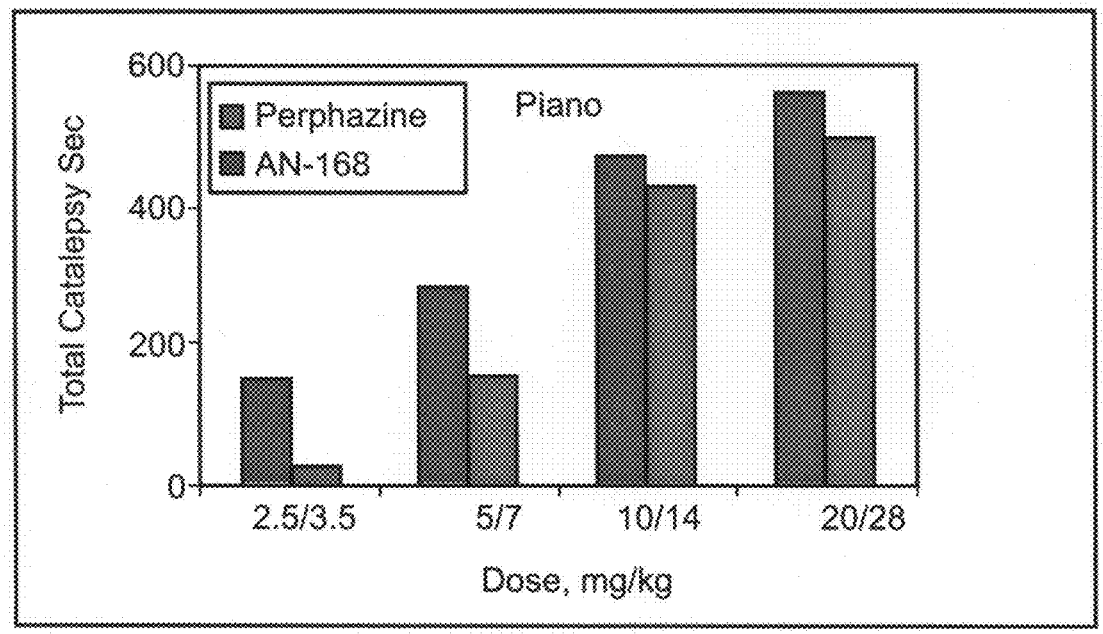
Figure 11:
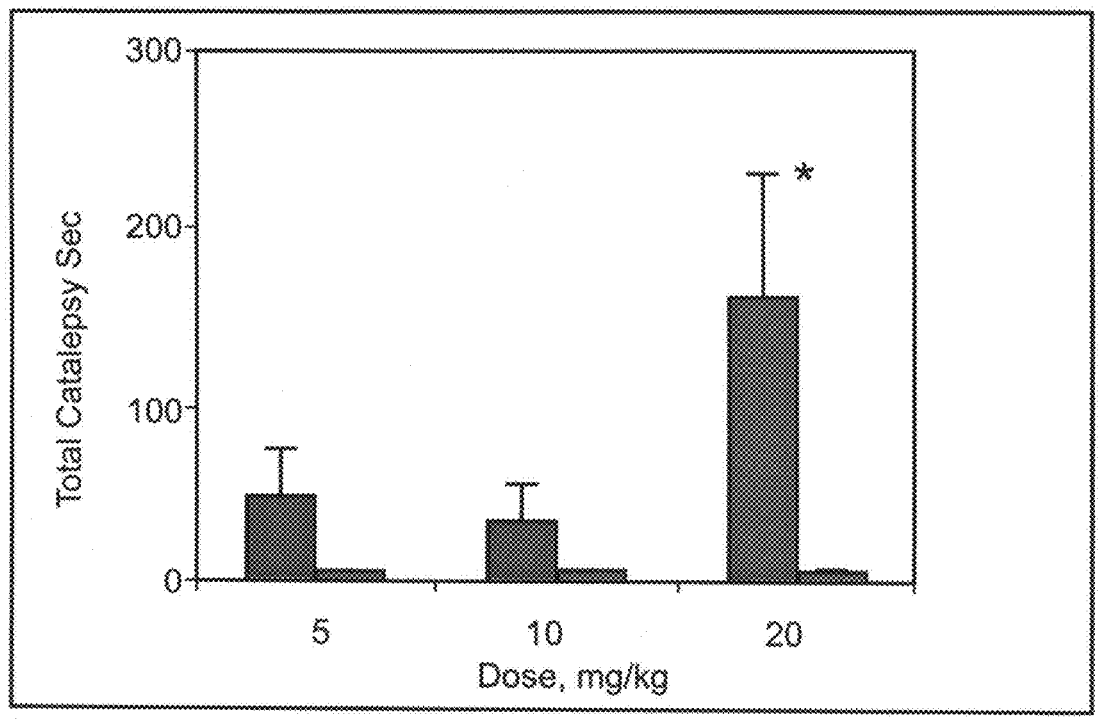
Figure 12:
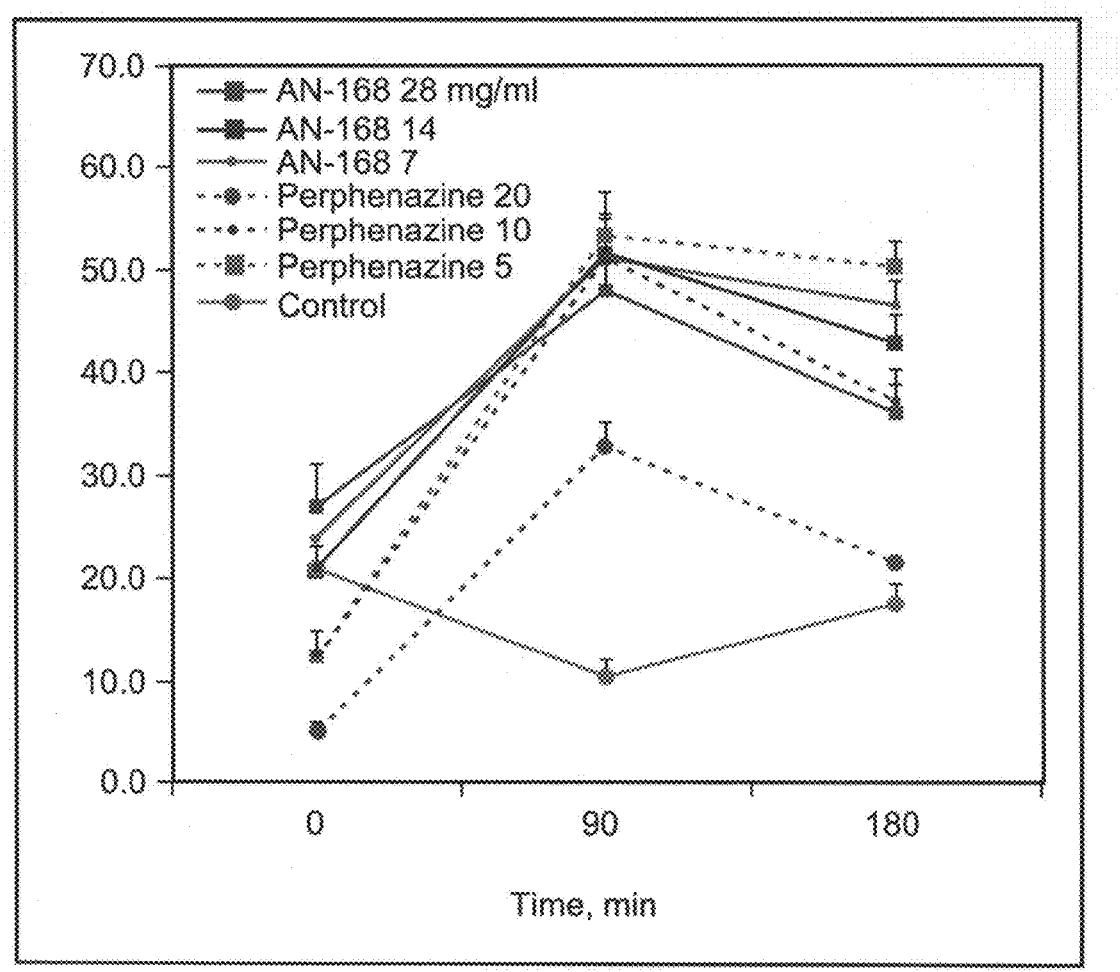
Figure 13:
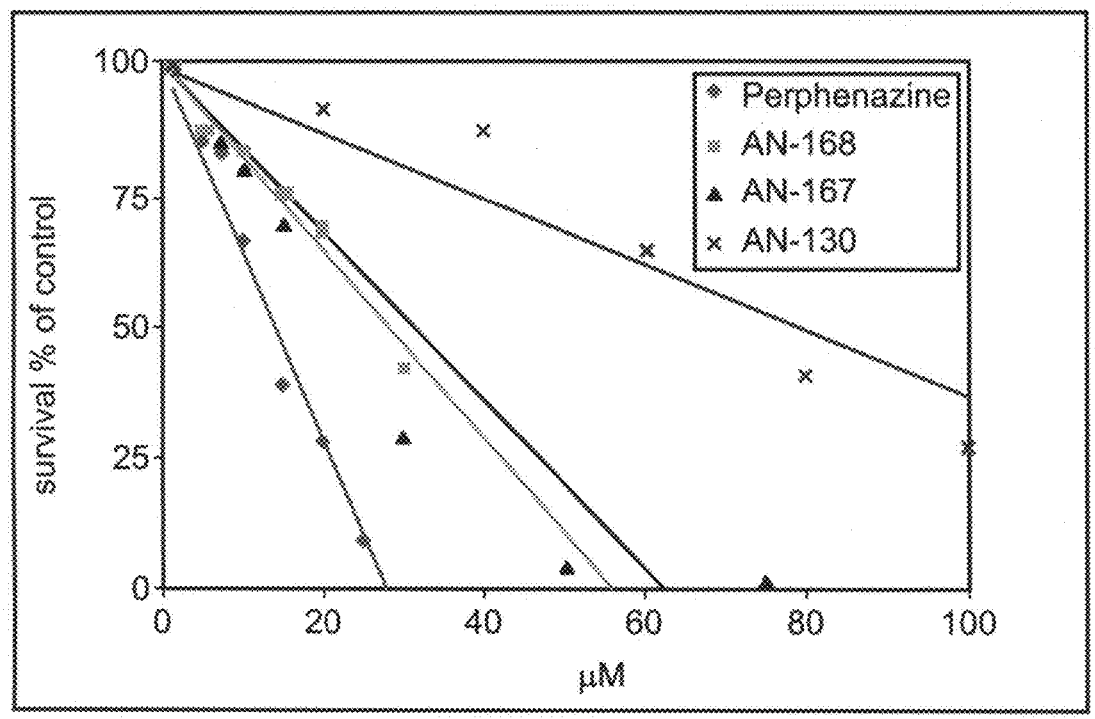
Figure 14:
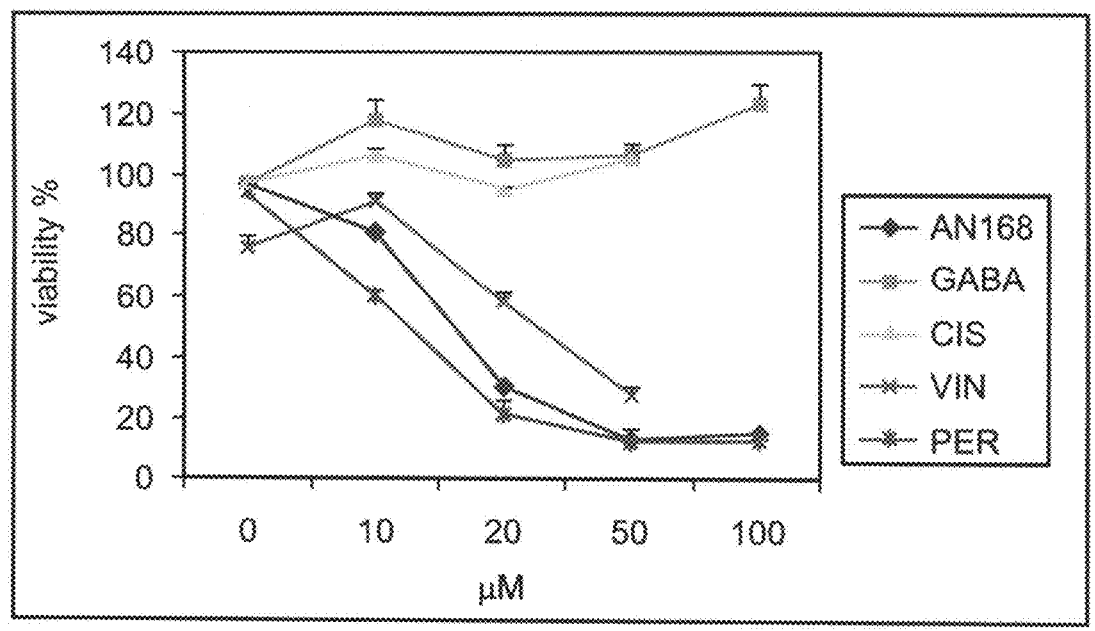
Figure 15:
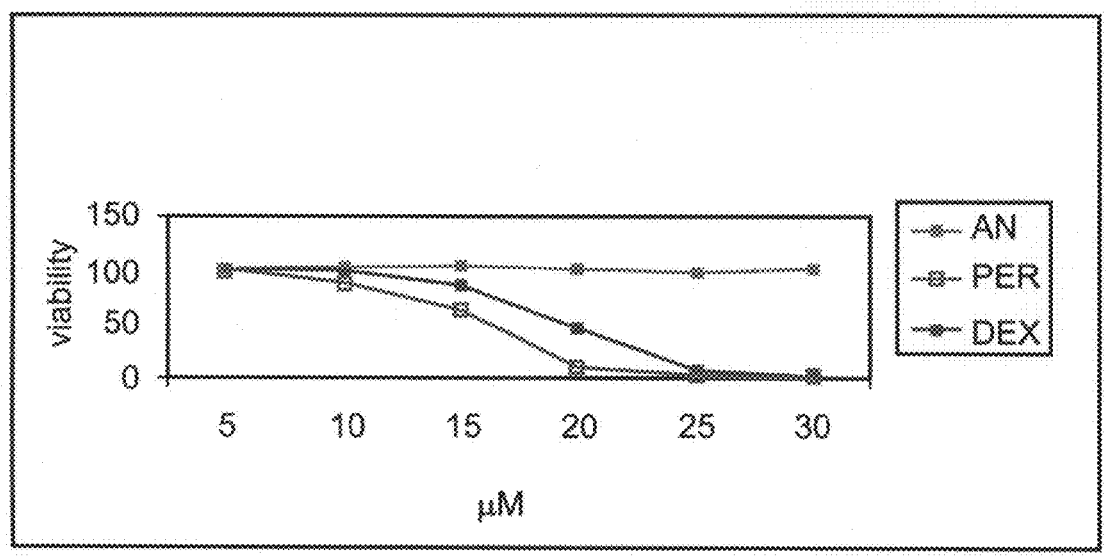
Figure 16:
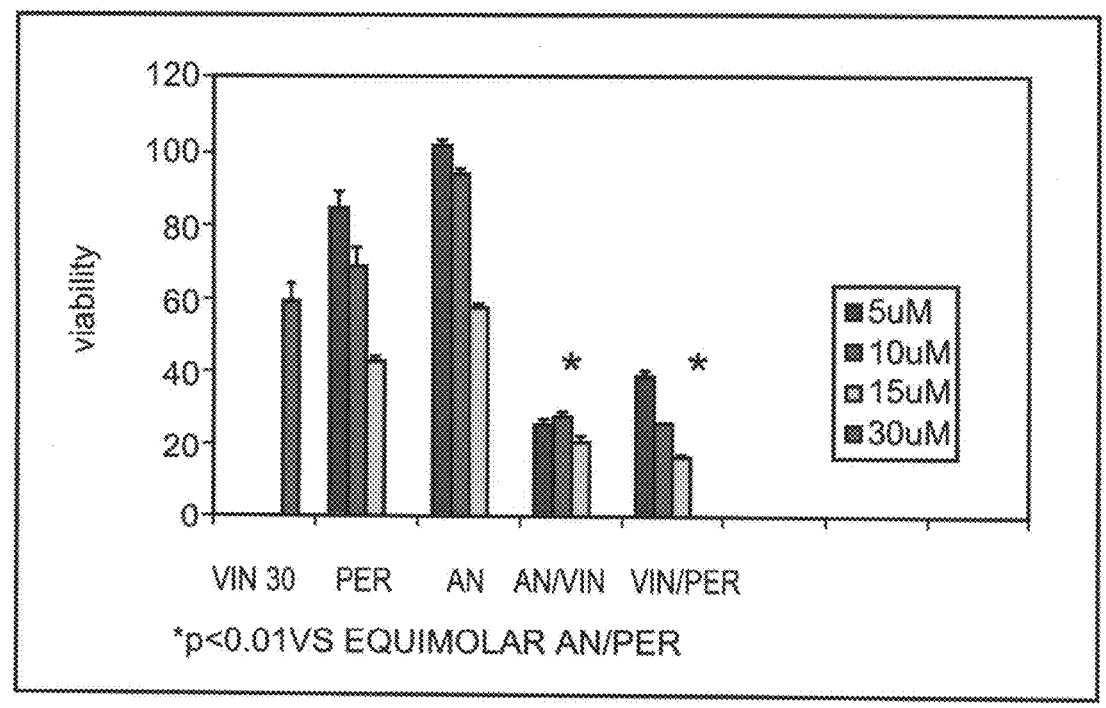
Figure 17:
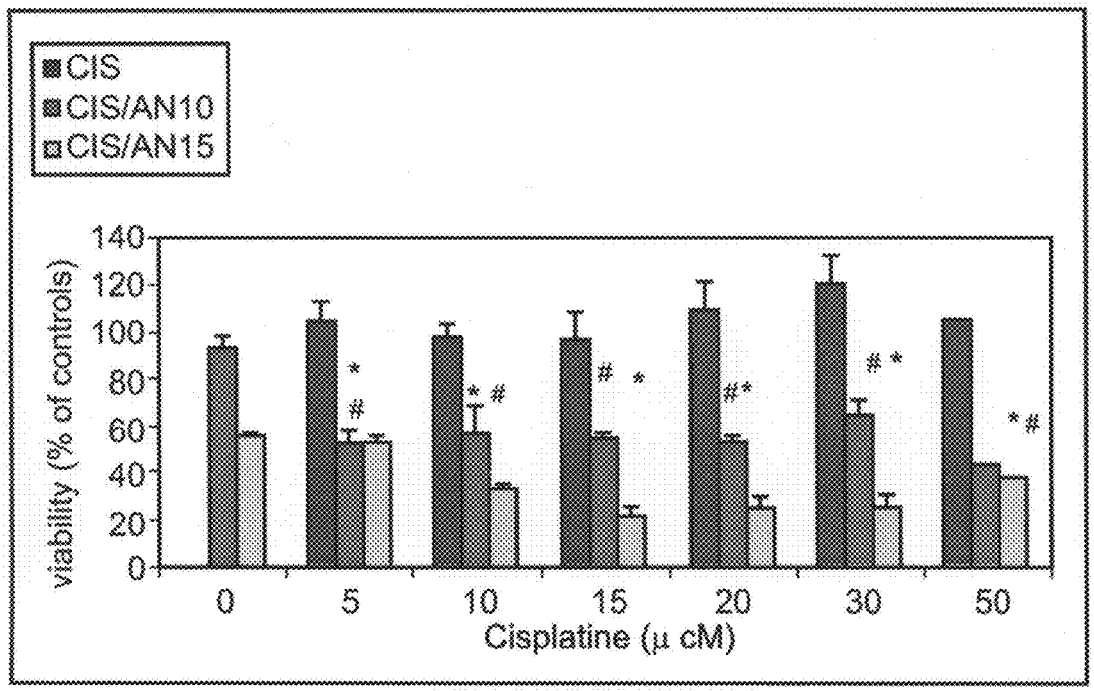
Figure 18:
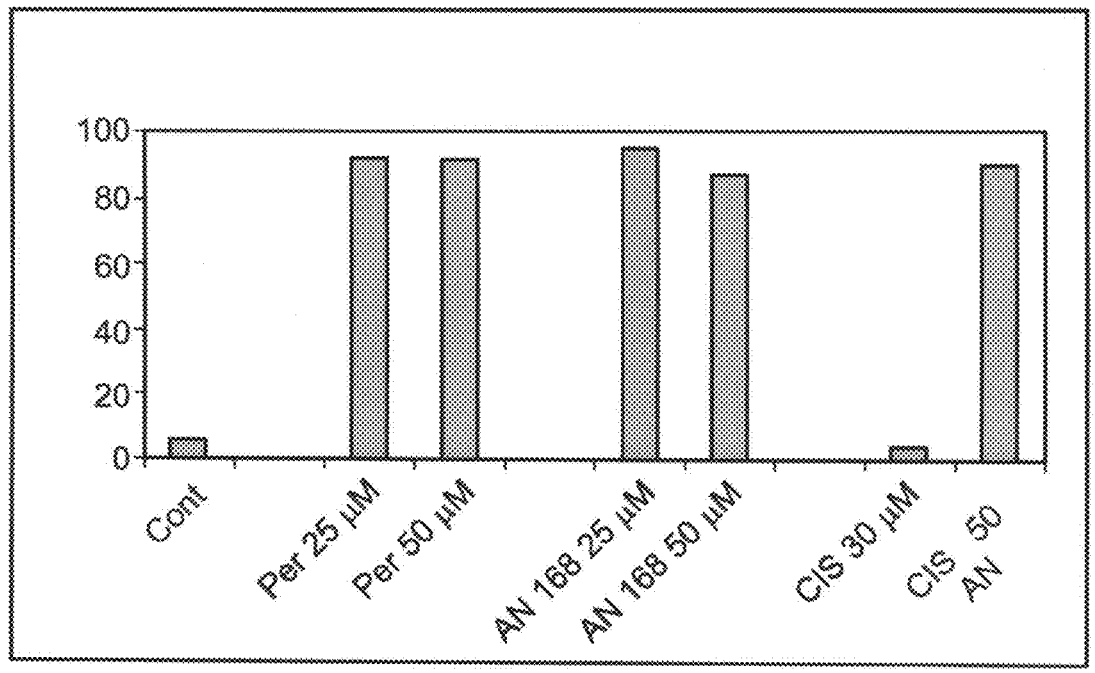
Figure 19:
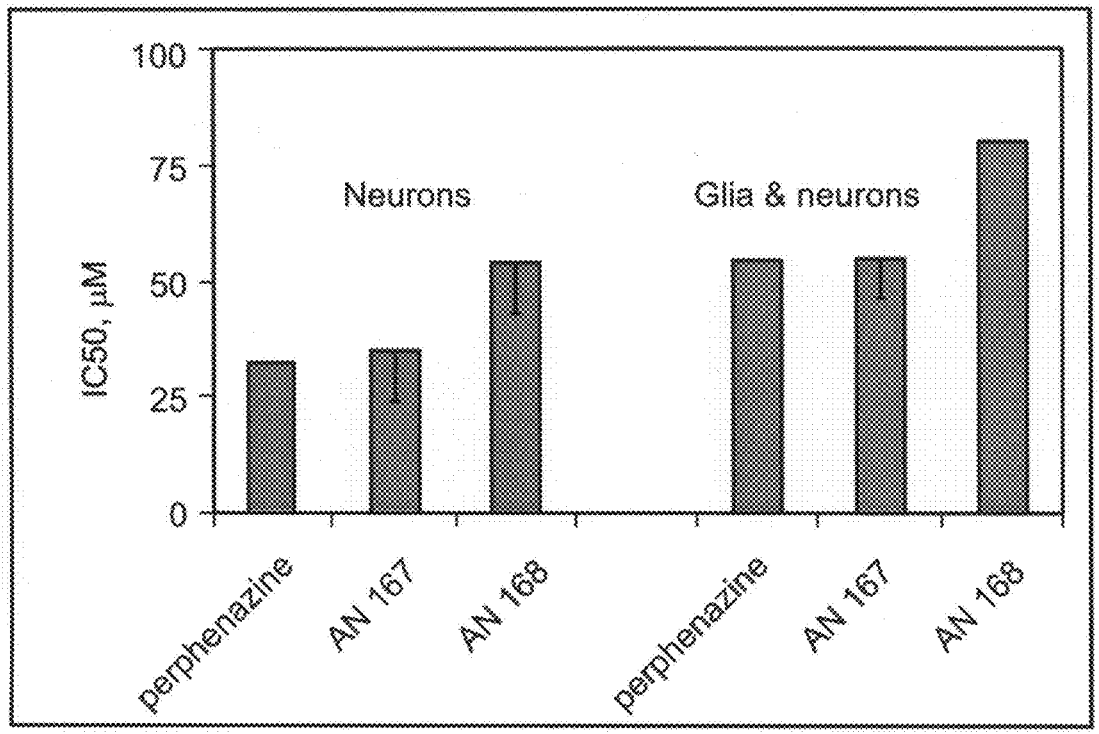
Figure 20:
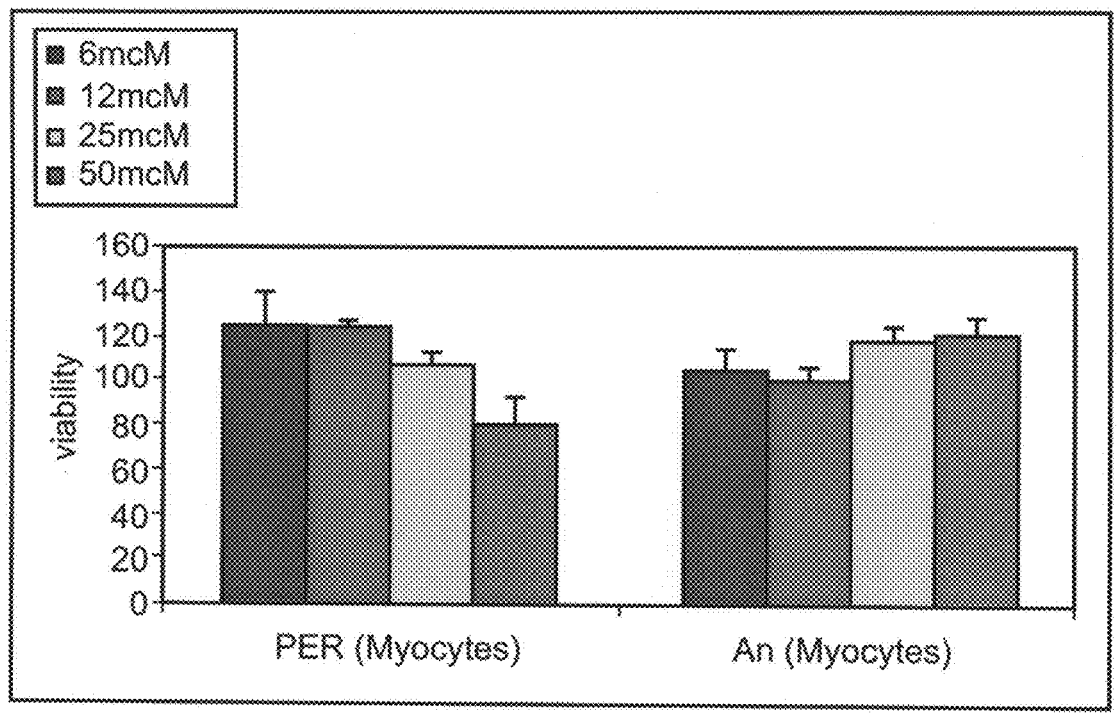
Figure 21:
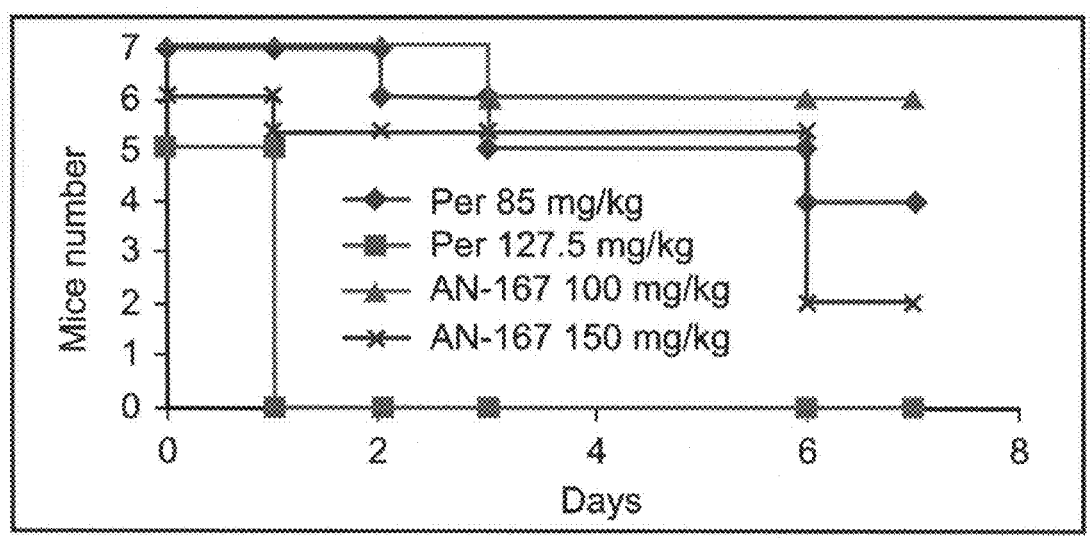
Figure 22:
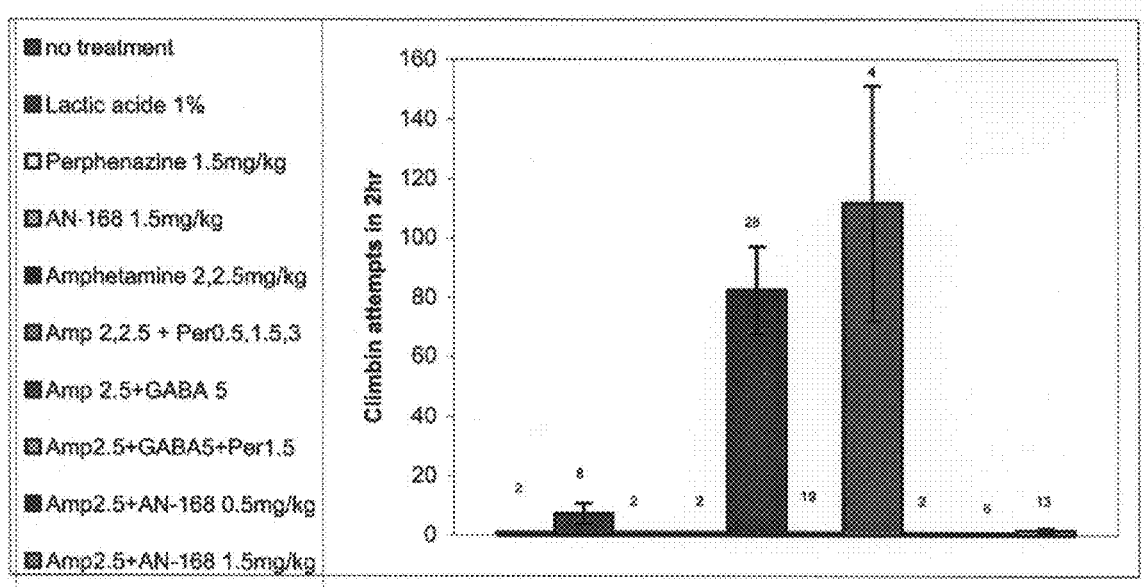
Figure 23:
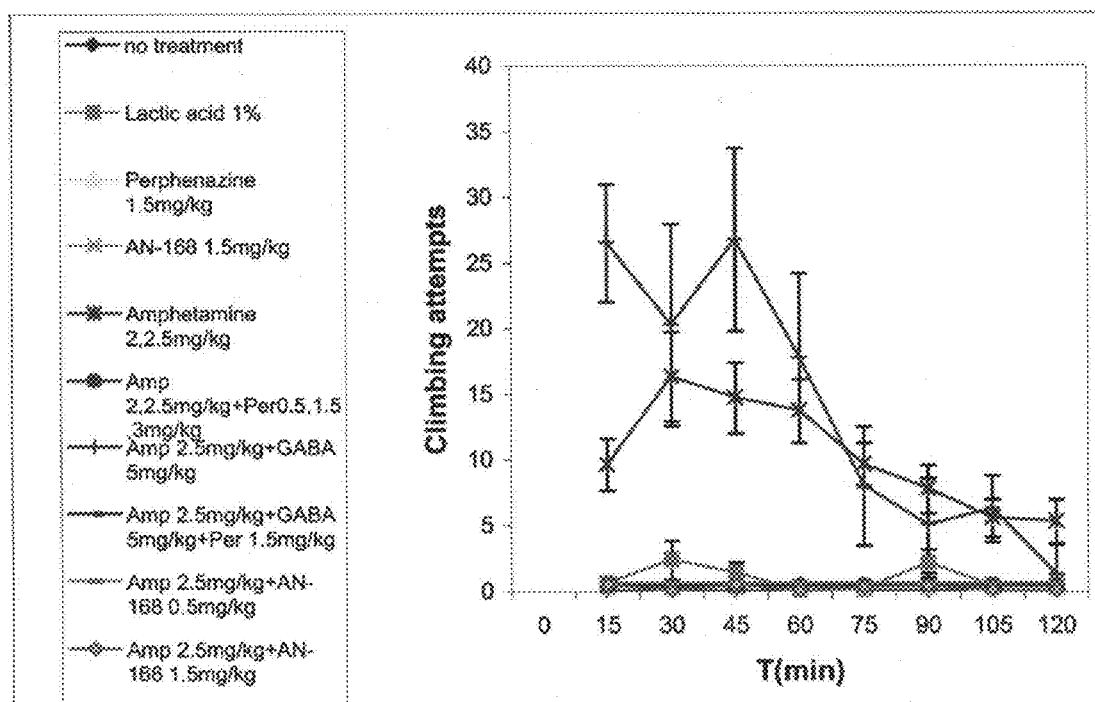
Figure 24:
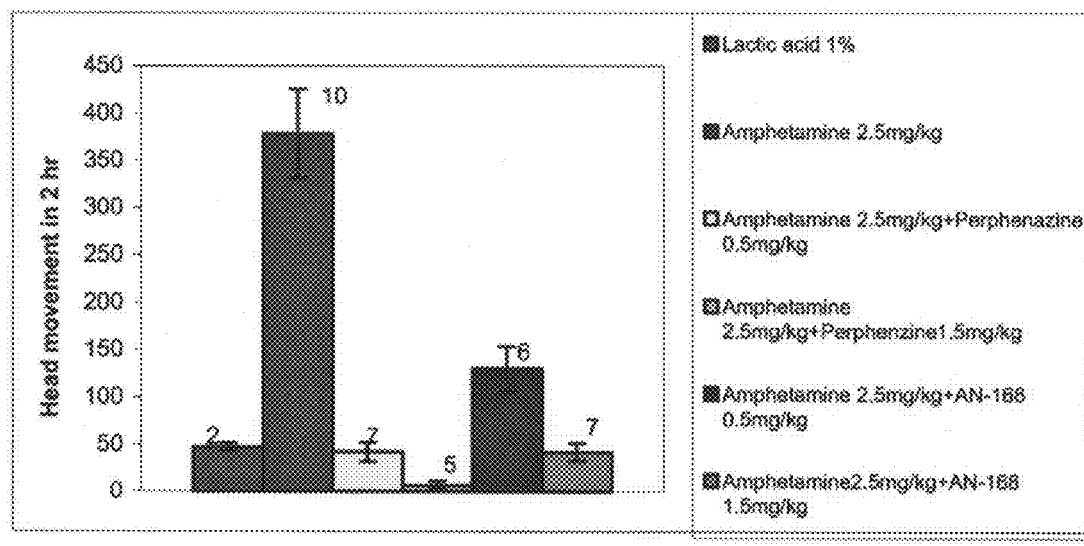
Figure 25:
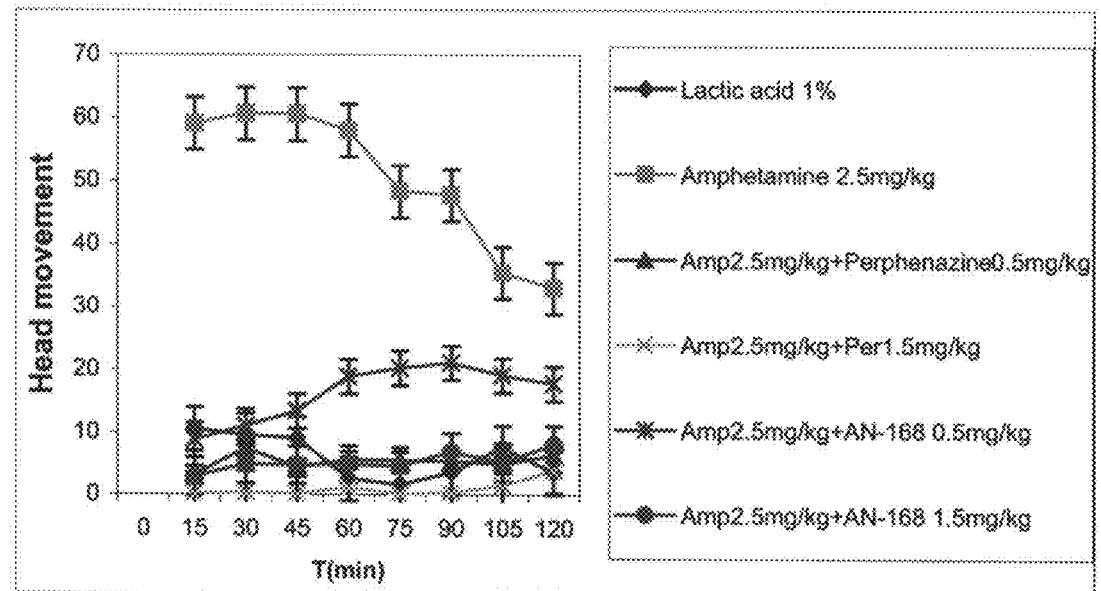
Figure 26:
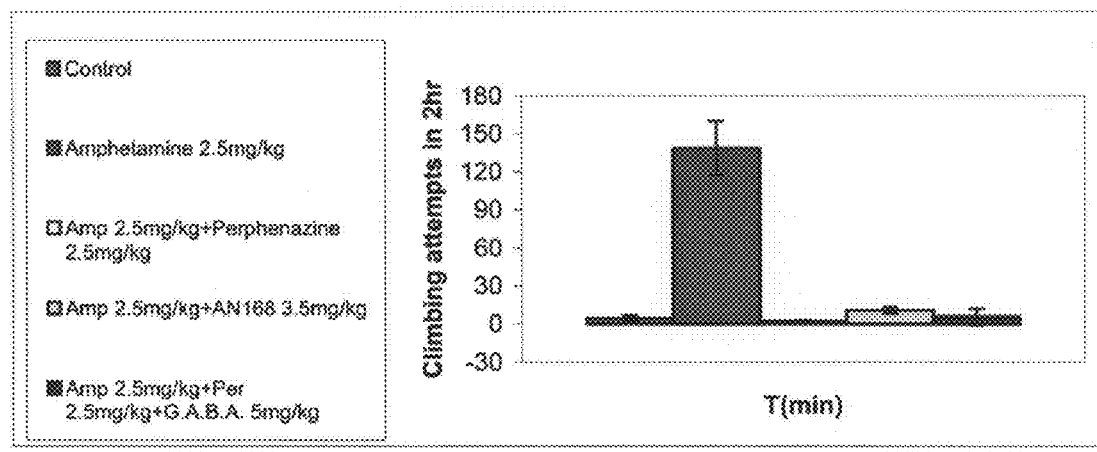
Figure 27:
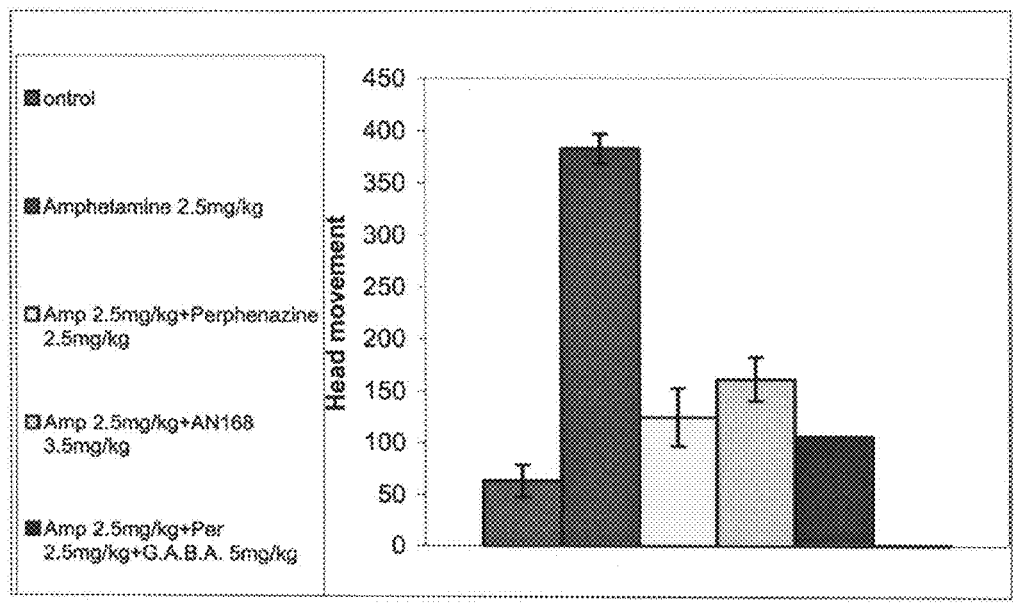
Figure 28:
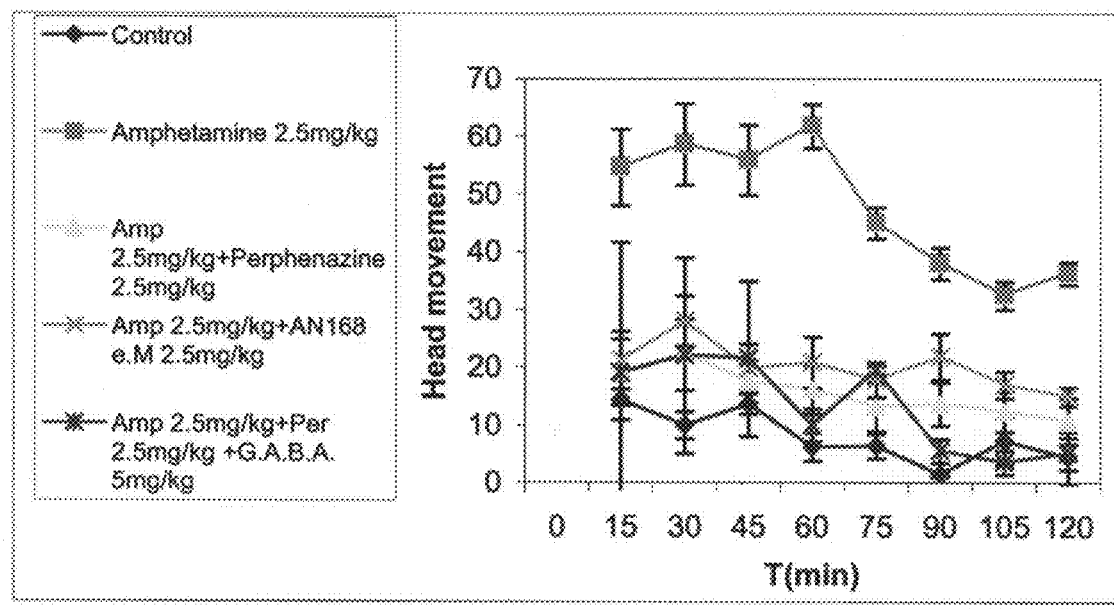
Figure 29:
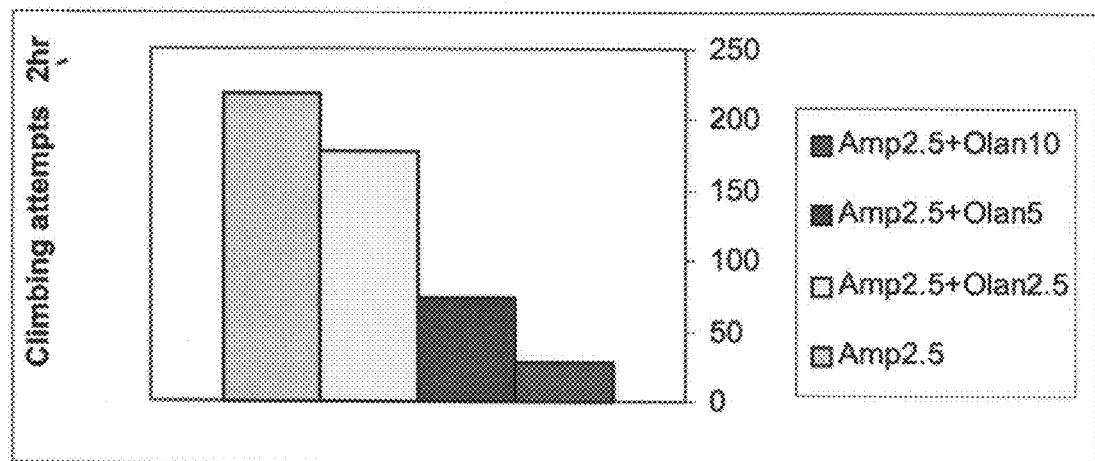
Figure 30:
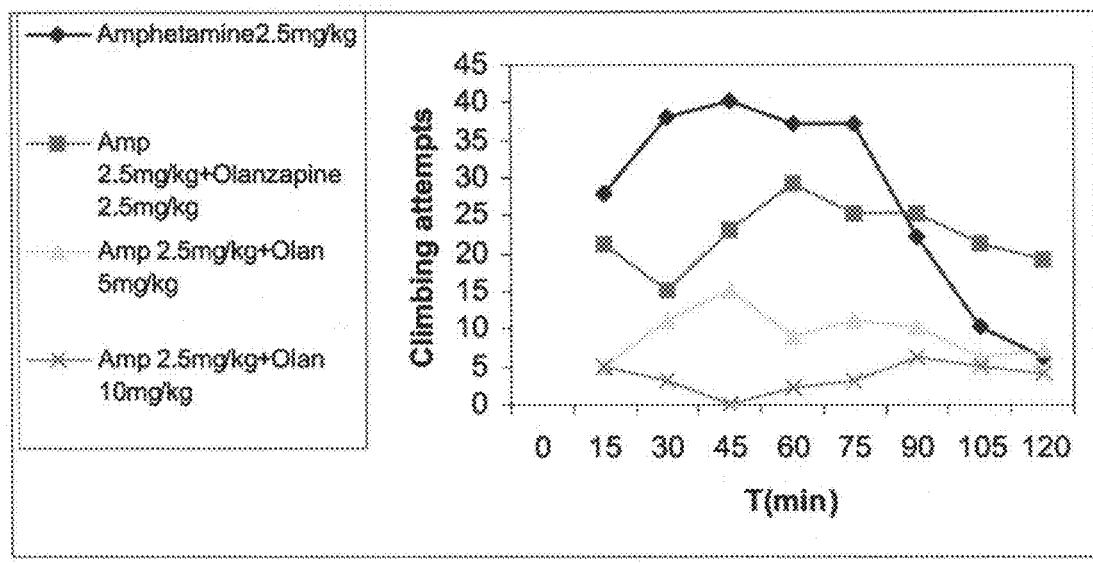
Figure 31:
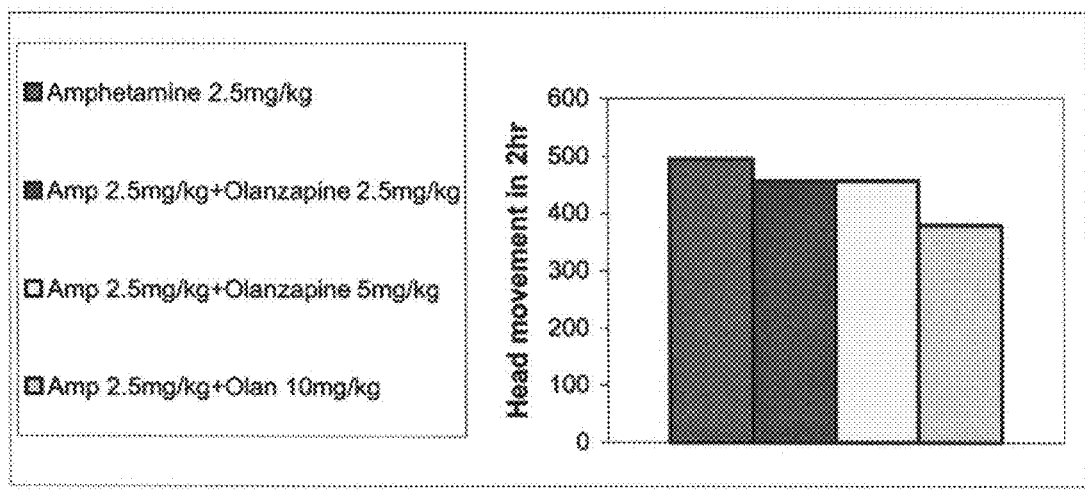

FIGS. 1a and 1b show a bar graph and plots, obtained by Structure Activity Relationship (SAR) studies, demonstrating the effect of perphenazine and its chemical conjugates according to the present invention (AN 167, AN 168 and AN 130) on total catalepsy (FIG. 1a) and on prolactin blood levels (FIG. 1b) in rats injected intraperitoneally with 5 mg/Kg body weight perphenazine and equimolar doses of its chemical conjugates;

FIG. 2 is a bar graph demonstrating the total catalepsy in rats following treatment with 5 mg/Kg perphenazine and equimolar doses of its chemical conjugates according to the present invention (SAR studies);

FIGS. 3a and 3b show a bar graph and plots demonstrating the effect of perphenazine (5 mg/Kg), fluphenazine (7.5 mg/Kg) and their chemical conjugates (AN 167, AN 168, AN 180 and AN 187) according to the present invention (administered in equimolar doses) on total catalepsy in rats (FIG. 3a)

and the effect of perphenazine, fluphenazine and their GABA chemical conjugates AN 168 and AN 187 on prolactin blood levels in rats (FIG. 3b);

FIGS. 4a-b are comparative plots demonstrating the time course of catalepsy in rats, induced by perphenazine and its chemical conjugates according to the present invention (FIG. 4a) and fluphenazine and its chemical conjugates according to the present invention (FIG. 4b);

FIGS. 5a and 5b show a bar graph and comparative plots demonstrating the effect of a chemical conjugate of perphenazine and GABA (compound AN 168) of the present invention and an equimolar dose of a mixture of perphenazine and GABA on catalepsy in rats;

FIG. 6 is a bar graph demonstrating the effect of the chemical conjugates AN 167 and AN 168 of the present invention on total catalepsy in rats (averages of four independent experiments);

FIGS. 7a and 7b show bar graphs demonstrating the effect of the chemical conjugate AN 168, an equimolar dose of perphenazine and an equidose of a mixture of perphenazine and GABA on catalepsy in mice, measured in terms of the percentage of animals reaching the target within 2 minutes (FIG. 7a) and in terms of the time it took the animals to reach the target (FIG. 7b);

FIGS. 8a and 8b present comparative plots demonstrating the effect of orally administered perphenazine and its chemical conjugate AN 168 on catalepsy in rats, as measured by the "piano" test (FIG. 8b presents the data obtained in experiments conducted 3 months after the experiments presented in FIG. 8a);

FIGS. 9a and 9b present bar graphs demonstrating the total catalepsy induced in rats by orally administered perphenazine and its chemical conjugate AN 168, at various concentrations, as measured by the "piano" test (FIG. 9b presents the data obtained in experiments conducted 3 months after the experiments presented in FIG. 9a);

FIGS. 10a and 10b are comparative plots and a bar graph demonstrating the effect of various concentrations of orally administered perphenazine and its chemical conjugate AN 168 on the time course of catalepsy (FIG. 10a) and on total catalepsy (FIG. 10b) in rats, as measured by the "piano" test during 24 hours;

FIG. 11 is a bar graph demonstrating the effect of perphenazine and AN 168, orally administered at various concentrations, on total catalepsy in rats, as measured by the "wall" test;

FIG. 12 presents comparative plots demonstrating the effect of orally administered perphenazine and AN 168 on prolactin blood levels in rats;

FIG. 13 presents comparative plots demonstrating the effect of perphenazine and its chemical conjugates of the present invention, AN 130, AN 167 and AN 168, on the proliferation of B16 murine melanoma cells;

FIG. 14 presents comparative plots demonstrating the effect of increasing concentrations of perphenazine, AN 168, GABA, Vincristine and Cisplatin on the viability of C6 rat glioma cells;

FIG. 15 presents comparative plots demonstrating the effect of increasing concentrations of perphenazine, AN 168 and Dexamethasone on the viability of Jurkat T lymphoma cells;

FIG. 16 is a bar graph demonstrating the effect of various concentrations of perphenazine and AN 168 on the viability of C6 rat glioma cells treated with 30 μM Vincistine;

FIG. 17 is a bar graph demonstrating the effect of Cisplatin (5-50 μM) and a combination of Cisplatin (5-50 μM) and AN 168 (10 and 15 μM) on the viability of C6 rat glioma cells;

FIG. 18 is a bar graph demonstrating the effect of perphenazine, AN 168 and Cisplatin on DNA fragmentation in C6 rat glioma cells;

FIG. 19 is a bar graph demonstrating the effect of perphenazine and its chemical conjugates AN 130, AN 167 and AN 168 on normal brain cells ($IC_{50}$ values);

FIG. 20 is a bar graph demonstrating the effect of equimolar doses of perphenazine and AN 168 on the viability of rat myocytic cell;

FIG. 21 presents comparative plots demonstrating the time course of mortality in rats intraperitoneally injected with perphenazine (per) and compound AN 167 of the present invention;

FIG. 22 is a bar graph demonstrating the effect of intraperitoneal administration of various concentrations of perphenazine and/or GABA, and of equimolar doses of the chemical conjugate AN-168 on D-amphetamine-induced climbing behavior in rats, by the total number of climbing attempts recorded during two hours in each test group (each point represents the Mean +/– SEM, and the number of animal treated);

FIG. 23 presents comparative plots demonstrating the time course of the effect of intraperitoneal administration of various concentrations of perphenazine and/or GABA, and of equimolar doses of the chemical conjugate AN-168 on D-amphetamine-induced climbing behavior in rats during two hours;

FIG. 24 is a bar graph demonstrating the effect of intraperitoneal administration of various concentrations of perphenazine and equimolar doses of the chemical conjugate AN-168 on D-amphetamine-induced head movement in rats, recorded during two hours in each test group (each point represents the Mean +/– SEM, number of animal treated added);

FIG. 25 presents comparative plots demonstrating the time course of the effect of intraperitoneal administration of various concentrations of perphenazine and equimolar doses of the chemical conjugate AN-168 on D-amphetamine-induced head movement in rats during two hours;

FIG. 26 is a bar graph demonstrating the effect of oral administration of 2.5 mg/kg perphenazine, with or without 5 mg/kg GABA, and of equimolar dose of the chemical conjugate AN-168 on D-amphetamine-induced climbing behavior in rats, by the total number of climbing attempts recorded in each test group during two hours (each point represents the Mean +/– SEM and the number of animal treated);

FIG. 27 is a bar graph demonstrating the effect of oral administration of 2.5 mg/kg perphenazine with or without 5 mg/kg GABA and of equimolar dose of the chemical conjugate AN-168 on D-amphetamine-induced head movement in rats in each test group during two hours (each point represents the Mean +/– SEM);

FIG. 28 presents comparative plots demonstrating the time course of the effect of oral administration 2.5 mg/kg perphenazine with or without 5 mg/kg GABA and of equimolar dose of the chemical conjugate AN-168 on D-amphetamine-induced head movement in rats during two hours;

FIG. 29 is a bar graph demonstrating the effect of oral administration of various concentrations of olanzapine on D-amphetamine-induced climbing behavior in rats;

FIG. 30 presents comparative plots demonstrating the time course of the effect of oral administration of various concentrations of olanzapine on D-amphetamine-induced climbing behavior in rats; and FIG. 31 is a bar graph demonstrating the effect of oral administration of various concentrations of olanzapine on D-amphetamine-induced head movement in rats.

DESCRIPTION OF THE PREFERRED EMBODIMENTS

The present invention is of chemical conjugates of psychotropic drugs covalently linked to organic acids, methods of their preparation and their use in the treatment of psychotropic disorders and diseases, such as, but not limited to, schizophrenia, as well as proliferative disorders and diseases such as, but not limited to, brain tumors, brain metastases, peripheral tumors, MDR cancer and other proliferative diseases, and as chemosensitizers.

The principles and operation of the chemical conjugates according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated by the examples. The invention is capable of other embodiments or of being practiced or carried out in various ways. Also, it is to be understood that the phraseology and terminology employed herein is for the purpose of description and should not be regarded as limiting.

While conceiving the present invention, it was hypothesized that a chemical conjugate covalently coupling a psychotropic drug (which may have also anti-proliferative and/or chemosensitization activity) and a GABA agonist or an anti-proliferative agent could exert high psychotropic and/or anti-proliferative therapeutic activity, as well as chemosensitization activity, associated with minimized adverse side effects.

The underlying basis for this hypothesis is as follows: psychotropic disorders and diseases in general and psychotic disorders and diseases, such as schizophrenia, in particular, are treatable by several types of psychotropic drugs. However, the administration of the psychotropic drugs is typically accompanied by short and long term adverse side effects such as extrapyramidal symptoms (mainly induced by typical antipsychotics) and agranulocytosis (mainly induced by atypical anti-psychotics). The development of these adverse side effects, in particular the extrapyramidal symptoms, is attributed to an induced imbalance in the dopaminergic D1 and D2 receptors and to decreased activity of the GABA system in the brain.

Therefore, it was hypothesized that covalently coupling a psychotropic drug with a GABA agonist would result in a chemical conjugate that exerts psychotropic activity with minimized side effects.

In particular, it was assumed that such a coupling of a psychotropic drug and a GABA agonist would be highly beneficial in this respect since it would result in a compound that simultaneously exerts a psychotropic activity and a GABA-increased activity.

An increase of the GABA system activity, which is presently achieved by the administration of analgesics, GABA agonists or GABA-like compounds, is known to reduce the side effects induced by psychotropic drugs and to further provide other therapeutic benefits related to the GABA system (e.g., mood stabilization and relaxation). GABA agonists are further known to antagonize the increased sensitivity of dopaminergic receptors induced by psychotropic drugs. However, the administration of certain GABA agonists and analgesics is limited by their hydrophilic nature.

Therefore, it was further hypothesized that a chemical conjugate obtained by covalently coupling a psychotropic drug and a GABA agonist would be characterized by (i) synergistic psychotropic and GABA-increased activities induced by both the psychotropic drug moiety and the GABA agonist moiety; (ii) reduced psychotropics-induced side effects; (iii) improved pharmacokinetics with respect to crossing the blood brain barrier of the coupled psychotropic drug and the GABA agonist as compared to the parent compounds; and (iv) higher affinity to dopaminergic receptors in the brain, which would result in improved psychotropic activity.

Moreover, it is known in the art that some psychotropic drugs, in particular neuroleptic drugs such as phenothiazines, are potent anti-proliferative agents and can further serve as chemosensitizers when used in combination with a chemotherapeutic drug. Therefore it was still further hypothesized that a chemical conjugate covalently coupling a psychotropic drug and a chemical moiety having anti-proliferative activity would exert even higher anti-proliferative and/or chemosensitization activity. Such chemical conjugate could be highly beneficial in the treatment of proliferative disorders and diseases, especially in the brain, due to the affinity of the psychotropic derivative toward brain receptors and its improved brain pharmacokinetics.

While reducing the present invention to practice, as is further exemplified in the Examples section that follows, it was found that covalently coupling a psychotropic drug and a chemical moiety selected so as to reduce side effects induced by the psychotropic drug, such as a GABA agonist, or selected so as to exert anti-proliferative activity, results in chemical conjugates that are synergistically characterized by (i) minimized adverse side effects; (ii) high psychotropic activity; (iii) high anti-proliferative activity; (vi) high chemosensitization activity; and (iv) reduced toxicity, all as compared to known psychotropic drugs. The chemical conjugates that include a GABA agonist were further characterized by synergistic psychotropic and GABA induced activities.

Thus, the chemical conjugates are used according to the present invention to treat psychotropic disorders and diseases as well as proliferative disorders and diseases, as anti-proliferative agents and/or as chemosensitizers. Each of the chemical conjugates which are used to treat psychotropic and/or proliferative disorders and diseases according to the present invention includes a first chemical moiety that is covalently linked to a second chemical moiety. The first chemical moiety is a psychotropic drug residue, whereas the second chemical moiety is an organic acid, selected so as to reduce side effects induced by the psychotropic drug when administered per se and/or to exert anti-proliferative activity.

As used herein, the term "chemical moiety" refers to a residue derived from a chemical compound, which retains its functionality.

The term "residue" refers herein to a major portion of a molecule which is covalently linked to another molecule, as is well accepted in the art.

Thus, the phrase "psychotropic drug residue" refers to a major portion of a psychotropic drug that is covalently linked to another chemical moiety, as this term is defined hereinabove.

As is described hereinabove, the phrase "psychotropic drug" encompasses any agent or drug that exerts an activity in the central nervous system and thereby can be used in the treatment of various central nervous system diseases or disorders.

Hence, psychotropic drug residues, according to the present invention, include, for example, residues derived from anxiolytic drugs such as, but not limited to, benzodiazepines, phenothiazines and butyrophenones, MAO inhibitors, anti-depressants anti-convulsive drugs (also referred to as anti-convulsants), anti-parkinsonian drugs, and acetylcholine esterase inhibitors. The psychotropic drugs can be tricyclic, bicyclic or monocyclic.

According to a preferred embodiment of the present invention, the psychotropic drug residues are preferably derived from anti-psychotic drugs, including typical and atypical psychotic drugs.

Particularly preferred psychotropic drugs, according to the present invention, are those having an amine group, a thiol group or an hydroxyl group, as these terms are defined hereinbelow, which can be reacted with the organic acid or a reactive derivative thereof. Such groups can be present in the psychotropic drug either as a free functional group or as a part of another functional group, e.g., an amide group, a carboxylic acid group and the like, as these terms are defined hereinbelow.

Representative examples of residues of such psychotropic drug residues, include, without limitation, a chlorpromazine residue, a perphenazine residue, a fluphenazine residue, a zuclopenthixol residue, a thiopropazate residue, a haloperidol residue, a benperidol residue, a bromperidol residue, a droperidol residue, a spiperone residue, a pimozide residue, a piperacetazine residue, an amilsulpride residue, a sulpiride residue, a clothiapine residue, a ziprasidone residue, a remoxipride residue, a sultopride residue, an alizapride residue, a nemonapride residue, a clozapine residue, an olanzapine residue, a ziprasidone residue, a sertindole residue, a quetiapine residue, a fluoxetine residue, a fluvoxamine residue, a desipramine residue, a paroxetine residue, a sertraline residue, a valproic acid residue a temazepam residue, a flutemazepam residue, a doxefazepam residue, an oxazepam residue, a lorazepam residue, a lormetazepam residue, a cinolazepam residue, a flutazolam residue, a lopirazepam residue, a meprobamate residue, a carisoprodol residue, an acetophenazine residue, a carphenazine residue, a dixyrazine residue, a priciazine residue, a pipothiazine residue, a homophenazine resdiue, a perimetazine residue, a perthipentyl residue, a flupentixol residue, a piflutixol residue, a teflutixol residue, an oxypethepin residue, a trifluperidol residue, a penfluridol residue, a meclobemide residue, a norclomipramine residue, an amoxapine residue, a nortriptyline residue, a protriptyline residue, a reboxetine residue, a tacrine residue, a rasagiline residue, an amatadine residue, a phenobarbital residue and a phenyloin residue.

According to a preferred embodiment of the present invention, the psychotropic drug residue further exerts anti-proliferative activity. Such dual active psychotropic drugs include, for example, phenothiazines and derivatives thereof.

According to another preferred embodiment of the present invention, the psychotropic drug residue further exerts chemosensitization activity. Such dual active psychotropic drugs include, for example, phenothiazines and derivatives thereof, thioxanthenes and derivatives thereof, clozapine, clomipramine and paroxetine.

As used herein, the term "chemosensitization" means an increase or an enhancement of the measured cytotoxicity of a chemotherapeutic agent on cancer cells, particularly multi-drug resistant cancer cells, in the presence of a chemosensitizing agent, as is compared to the level of cytotoxicity exerted by the chemotherapeutic agent in the absence of the chemosensitizing agent.

The terms "chemosensitizing agent" and "chemosensitizer", which are used herein interchangeably, describe compounds that render cancer cells more sensitive to chemotherapy.

As stated hereinabove, the psychotropic drug residue, according to the present invention, is covalently coupled to a second chemical moiety, which is an organic acid residue.

The phrase "organic acid residue" refers to a residue, as defined herein, that is derived from an organic acid that includes a free carboxylic group.

The term "free carboxylic group" includes a "—C(=O)OH" group either as is, in its protonated or in its ionized or salt state.

The organic acid residue, according to the present invention, is selected so as to either reduce the side effects that could be induced by the psychotropic drug if administered alone or to exert anti-proliferative activity. The organic acid residue, according to the present invention, can be, for example, a residue that has a general formula —R—C(=O)—, where R can be, for example, a hydrocarbon residue that has 1-20 carbon atoms.

The term "hydrocarbon" as used herein refers to an organic compound that includes, as its basic skeleton, a chain of carbon atoms and hydrogen atoms that are covalently linked.

Thus, the hydrocarbon residue according to the present invention can be alkyl or cycloalkyl.

As used herein, the term "alkyl" refers to a saturated aliphatic hydrocarbon including straight chain and branched chain groups. Preferably, the alkyl group has 1 to 20 carbon atoms.

Whenever a numerical range, e.g., "1-20", is stated herein, it means that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, the alkyl has 3 to 5 carbon atoms.

As used herein, the term "cycloalkyl" includes an all-carbon monocyclic or fused ring (i.e., rings which share an adjacent pair of carbon atoms) group wherein one of more of the rings does not have a completely conjugated pi-electron system. Examples, without limitation, of cycloalkyl groups include cyclopropane, cyclobutane, cyclopentane, cyclopentene, cyclohexane, cyclohexadiene, cycloheptane, cycloheptatriene and adamantane.

The hydrocarbon residue, according to the present invention, can be straight or branched. The hydrocarbon residue can further be saturated or unsaturated. When unsaturated, the hydrocarbon residue can include a double bond or a triple bond in its carbon chain. An unsaturated hydrocarbon residue can further include an aryl.

As used herein, an "aryl" group refers to an all-carbon monocyclic or fused-ring polycyclic (i.e., rings which share adjacent pairs of carbon atoms) groups having a completely conjugated pi-electron system. Examples, without limitation, of aryl groups include phenyl, naphthalenyl and anthracenyl.

The hydrocarbon residue can further be substituted or non-substituted. When substituted, the substituent can be, for example, alkyl, cycloalkyl, aryl, heteroaryl, heteroalicyclic, hydroxy, alkoxy, aryloxy, cyano, halo, oxo, amido and amino.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups, include pyrrole, furane, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, alkyl, cycloalkyl, hydroxy, alkoxy, aryloxy, cyano, halo, oxo, amido and amino.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituted group can be, for example, alkyl, cycloalkyl, aryl, heteroaryl, halo, trihalomethyl, hydroxy, alkoxy, aryloxy, cyano, oxo, amido and amino.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

An "oxo" group refers to a —C(=O)—R' group, where R' can be, for example, alkyl, cycloalkyl or aryl.

A "halo" group refers to fluorine, chlorine, bromine or iodine.

A "trihalomethyl" group refers to a —CX$_3$— group wherein X is a halo group as defined herein.

An "amino" or "amine" group refers to a —NH$_2$ group.

An "amido" or "amide" group refers to a —C(=O)—NR$_a$R$_b$ group, where R$_a$ and R$_b$ can be, for example, hydrogen, alkyl, cycloalkyl and aryl.

The hydrocarbon residue, according to the present invention, can further include one or more heteroatoms interspersed within its chain. The heteroatoms can be, for example, oxygen, nitrogen and/or sulfur.

The hydrocarbon residue can further be a residue that has a general formula -Z-C(=O)O—CHR$_2$—R$_3$, where Z can be, for example, a single bond or a substituted or non-substituted hydrocarbon residue as described hereinabove; R$_2$ can be, for example, hydrogen or an alkyl residue having 1-10 carbon atoms; and R$_3$ can be, for example, hydrogen or a hydrocarbon residue as defined hereinabove.

Thus, representative examples of organic acids from which an organic acid residue according to the present invention can be derived include oxalic acid, malonic acid, succinic acid, glutaric acid, maleic acid, fumaric acid, phthalic acid, isophthalic acid, tetraphthalic acid, butyric acid, 4-phenylbutyric acid, 4-aminobutyric acid (GABA), valeric acid, propionic acid, retinoic acid, acetyl salicylic acid and ibuprofen.

According to a presently most preferred embodiment of the present invention, the second chemical moiety of the chemical conjugates is a GABA agonist residue.

As used herein, the phrase "GABA agonist residue" refers to a residue, as this term is defined hereinabove, of a GABA agonist, while the term "GABA agonist" describes compounds that are capable of activating the GABA system in the brain and are therefore pharmacologically related to GABA. The term "GABA agonist" is hence understood to include GABA itself, whereas the term "GABA agonist residue" is hence understood to include a residue of GABA agonist itself.

Thus, GABA agonist residues, according to the present invention, include, in addition to the GABA (γ-aminobutyric acid) residue itself, residues of other GABA agonist which can be covalently coupled to an anti-psychotic drug.

Examples of such GABA agonists residues include a (±) baclofen residue, an isonipecotic acid residue, a γ-hydroxybutyric acid residue, an aminooxyacetic acid residue, a β-(4-chlorophenyl)-γ-aminobutyric acid residue, a piperidine-4-sulfonic acid residue, an 3-aminopropylphosphonous acid residue, an 3-aminopropylphosphinic acid residue, an 3-(aminopropyl)methylphosphinic acid residue, a 1-(aminomethyl)cyclohexaneacetic acid residue (gabapentin), an 4-amino-5-hexenoic acid (γ-vinyl GABA, vigabatrin) and an 3-(2-imidazolyl)-4-aminobutanoic acid residue.

According to another presently preferred embodiment of the invention, the second chemical moiety in the chemical conjugates of the present invention is an anti-proliferative agent residue.

The term "anti-proliferative agent residue", as used herein, refers to a residue, as defined herein, of a compound characterized by an anti-proliferative activity.

According to a preferred embodiment of the present invention, the anti-proliferative agent is butyric acid or 4-phenylbutyric acid. These compounds are known to exert anti-cancer activity and are further characterized as compounds of which GABA is a derivative and may therefore further act as GABA mimetic agents.

According to another preferred embodiment of the present invention, the second chemical moiety in the chemical conjugates of the present invention is an analgesic.

The incorporation of analgesics in the chemical conjugates of the present invention may also provide for dual pharmacological activity, namely, psychotropic activity and pain relief. Furthermore, the presently known analgesics typically suffer many disadvantages such as poor pharmacokinetics and adverse side effects, e.g. significant convulsive effects, oftentimes associated with systemic administration thereof. Conjugation of analgesics with psychotropic agents can therefore improve their pharmacokinetics and reduce these side affects. Moreover, it is well accepted in the art that some analgesics are associated GABA activity.

Thus, the second chemical moiety of the chemical conjugates of the present invention include an organic acid residue, which is preferably a GABA agonist residue, an analgesic residue or an anti-proliferative agent residue, as these terms are defined and exemplified hereinabove.

The second chemical moiety in the chemical conjugates of the present invention is covalently linked to the first chemical moiety preferably via an ester bond. The ester bond can be a carboxylic ester bond, an oxyalkyl carboxylic ester bond, an amide bond or a thioester bond.

As used herein, the phrase "carboxylic ester bond" includes an "—O—C(=O)-" bond.

As used herein, the phrase "oxyalkyl carboxylic ester bond" includes an "O—R—O—C(=O)-" bond, where R is an alkyl, as defined hereinabove. Preferably R is methyl.

The phrase "amide bond" includes a "—NH—C(=O)-" bond.

The phrase "thioester bond" includes a "—SH—C(=O)-" bond.

Such ester bonds are known to be hydrolizable by brain derived enzymes, such as esterases and amidases, and it is therefore assumed and further demonstrated by the experimental results described herein (see, for example, FIGS. 5a-b) that the chemical conjugates of the present inventions act as prodrugs that are metabolized in the brain and thereby simultaneously release the psychotropic drug and the organic acid, thus, providing for advantageous co-pharmacokinetics for the psychotropic drug and the organic acid.

This process is highly advantageous since it provides (i) a simultaneous action of the psychotropic drug and the organic acid, which synergistically results in reduced side effects induced by the drug and in dual activity of both moieties; (ii) higher affinity of the prodrug to the dopaminergic receptors which results in synergistically higher psychotropic activity and synergistically higher anti-proliferative activity toward brain proliferative disorders; and (iii) improved brain permeability of both chemical moieties.

In another aspect, the present invention further provides a method of synthesizing the chemical conjugates described hereinabove. The method is effected, generally, by reacting an organic acid with a psychotropic drug, so as to obtain a residue of the organic acid covalently linked to a residue of the psychotropic drug.

Herein, the terms "a residue of an organic acid" and "a residue of a psychotropic drug" are equivalent to the terms "organic acid residue" and "psychotropic drug residue", respectively, as these terms are defined hereinabove. It should be evident to a skilled artisan that by reacting an organic acid and a psychotropic drug, to thereby form a covalent link therebetween, a final product that includes residues of the organic acid and the psychotropic drug is produced.

Hence, the organic acid that is reacted in the method of this aspect of the present invention, includes any compound that corresponds to the organic acid residue described hereinabove and can therefore include all the organic acids from which the organic acid residues described hereinabove are derived.

For example, organic acids that are usable in the context of this aspect of the present invention include GABA agonists which correspond to the preferred GABA agonist residues described hereinabove. Similarly, the organic acids can include anti-proliferating agents, such as butyric acid and 4-phenylbutyric acid, which correspond to the anti-proliferating agent residues described hereinabove.

In the same manner, the psychotropic drug that is reacted in the method according to this aspect of the present invention corresponds to any of the psychotropic drug residues described hereinabove.

The method of synthesizing the chemical conjugates of the present invention, described hereinabove, can be further manipulated in accordance with the type of the organic acid used and/or the type of the covalent linkage between the organic acid residue and the psychotropic drug residue.

As is discussed in detail hereinabove, preferred organic acids according to the present invention include, for example, anti-proliferating agents such as butyric acid and derivatives thereof, organic acids that have the general formula R—C(=O)—OH (corresponding to the organic acid residue R—(C=O)—O), and others. Most of these preferred organic acids do not include a free amino group and can therefore be used in the synthesis of the present invention without further manipulations.

As is further discussed in detail hereinabove, in the chemical conjugates of the present invention, the organic acid residue and the psychotropic drug residue are covalently linked by an ester bond that can be either a carboxylic ester bond, an alkyloxy carboxylic ester bond, a thioester bond or an amide bond, as these terms are defined hereinabove.

In cases where the residues are covalently linked via a carboxylic aster bond, the method of synthesizing the chemical conjugates of the present invention is preferably effected by first converting the organic acid into its corresponding acyl chloride derivative, or any other acyl halide derivative, so as to activate the organic acid. The acyl chloride derivative is thereafter reacted with the psychotropic drug, which typically includes a free hydroxyl group, in a well-known nucleophilic-addition reaction, so as to obtain the desired chemical conjugate having the organic acid residue covalently linked to the psychotropic drug residue via a carboxylic ester bond. This reaction is preferably performed under basic conditions, so as to activate the psychotropic drug and/or to neutralize compounds that are present as their hydrochloride salts. However, the organic acid and/or the psychotropic drug can be activated by any other known method.

In cases where the residues are covalently linked via a thioester bond, the method of synthesizing the chemical conjugates of the present invention is preferably effected by converting the psychotropic drug into its corresponding thiol derivative and converting the organic acid into its corresponding acyl chloride derivative, or into any other activated derivative thereof. The thiol derivative is thereafter reacted with the activated organic acid, by well-known procedures, so as to obtain the desired chemical conjugate having the organic acid residue covalently linked to the psychotropic drug residue via a thioester bond. It should be noted that some of the presently known psychotropic drugs include a free thiol group and therefore such drugs can be directly reacted with an acyl chloride derivative of the organic acid. Psychotropic drugs that do not include a free thiol group can be easily reacted so as to obtain a thiol derivative thereof, by methods well known in the art.

In cases where the residues are covalently linked via an amide bond, the method of synthesizing the chemical conjugates of the present invention is preferably effected by first converting the organic acid into its corresponding acyl chloride derivative, so as to activate the organic acid and by further converting the psychotropic drug into an amine derivative thereof. The acyl chloride derivative is thereafter reacted with the amino group of the psychotropic drug, in a well-known nucleophilic-addition reaction, or by any other of the known procedures for producing an amide bond, so as to obtain the desired chemical conjugate having the organic acid residue covalently linked to the psychotropic drug residue via an amide bond. It should be noted that some of the presently known psychotropic drugs include a free amine group and therefore such drugs can be directly reacted with an acyl chloride derivative of the organic acid. Psychotropic drugs that do not include a free amine group can be easily reacted so as to obtain an amine derivative thereof, by methods well-known in the art.

In cases where the residues are covalently linked via an alkyloxy carboxylic ester bond, the method of synthesizing the chemical conjugates of the present invention is preferably effected by converting the psychotropic drug into a chloroalkyl ester derivative thereof, preferably chloromethyl ester derivative thereof. The chloromethyl ester derivative is thereafter reacted with the organic acid, in a well-known nucleophilic-addition reaction, or by any other of the known procedures for producing an alkyloxy carboxylic ester bond, so as to obtain the desired chemical conjugate having the organic acid residue covalently linked to the psychotropic drug residue via an alkyloxy carboxylic ester bond. It should be noted that covalently linking the organic acid and the psychotropic drug via an alkyloxy carboxylic ester bond is particularly preferred in cases where the psychotropic drug includes a free carboxylic acid group, since it avoids the formation of the typically unstable anhydride conjugate.

The methods described above are typically effective when the organic acid does not have a free amino group. However, in cases where the organic acid includes a free amino group, as is the case of GABA agonists, for example, the amino group should be protected during the described reaction with psychotropic drug. Protecting the free amino group is required since it is a relatively chemically active group, which can therefore undesirably participate in the reaction.

Hence, a preferred method of synthesizing chemical conjugates that include a GABA agonist residue having a free amino group is preferably effected by first protecting the free amino group. Protecting the amino group can be performed by reacting the organic acid with a known protecting group such as, but not limited to, tert-butoxycarbonyl (Boc) and benzyloxycarbonyl (Cbz). The amino-protected organic acid is then reacted with the anti-psychotic drug, so as to obtain an amino-protected organic acid residue covalently linked to the psychotropic drug residue. The protecting group is then removed. Further preferably, the amino-protected organic acid is converted to its acyl imidazole derivative, so as to activate the organic acid prior to the reaction with the psychotropic drug.

Further according to the present invention there is provided a pharmaceutical composition including the chemical conjugate of the invention as an active ingredient.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of lactic acid.

In this respect, it should be pointed out that some of the chemical conjugates of the present invention, according to preferred embodiments, are readily soluble in aqueous media and are therefore easily formulated. Such convenient formulation provides an additional advantage of the chemical conjugates of the present invention over the known ester conjugates of anti-psychotic drugs, which typically include long-chain fatty acids and are therefore non-soluble in aqueous media and administered as oily formulation.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

For injection, the chemical conjugates of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the chemical conjugates can be formulated readily by combining the active compounds with pharmaceutically acceptable carriers well known in the art. Such carriers enable the conjugates of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, manioc, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the chemical conjugates for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The chemical conjugates described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active compound in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the conjugates to allow for the preparation of highly concentrated solutions.

Alternatively, the active ingredient may be in powder form for constitution with a suitable vehicle, e.g., sterile, pyrogen-free water, before use.

The chemical conjugates of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of chemical conjugate effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any chemical conjugate used in the methods of the invention, the therapeutically effective amount or dose can be estimated initially from activity assays in cell cultures and/or animals. For example, a dose can be formulated in animal models to achieve a circulating concentration range that includes the IC50 as determined by activity assays (e.g., the concentration of the test compound, which achieves a half-maximal inhibition of the proliferation activity). Such information can be used to more accurately determine useful doses in humans.

Toxicity and therapeutic efficacy of the chemical conjugates described herein can be determined by standard pharmaceutical procedures in experimental animals, e.g., by determining the IC50 and the LD50 (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain the psychotropic and/or the anti-proliferative effects, termed the minimal effective concentration (MEC). The MEC will vary for each preparation, but can be estimated from in vitro and/or in vivo data, e.g., the concentration necessary to achieve 50-90% inhibition of a proliferation of certain cells may be ascertained using the assays described herein. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as a FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a chemical conjugate of the invention formulated in a compatible pharmaceutical carrier may also be prepared, placed in an appropriate container, and labeled for treatment of an indicated condition. Suitable conditions indicated on the label may include, for example, psychotropic disease or disorders such as schizophrenia, paranoia, childhood psychoses, Huntington's disease, Gilles de la Tourette's syndrome, depression, manic depression, anxiety, Parkinson disease, Alzheimer disease and epilepsy, brain proliferative disorders and MDR cancer, and chemosensitization, as this term is defined hereinabove.

Hence, according to preferred embodiments of the present invention, the pharmaceutical composition is packaged in a packaging material and is identified in print, on or in the packaging material, for one or more of the following uses: for use in the treatment of psychotropic disorders or diseases, for use in the treatment of brain or peripheral proliferative disorders or diseases, for use in the treatment of cancer such as MDR cancer and for use in chemosensitization, in combination with a chemotherapeutic agent and/or in a medical condition for which chemosensitization is beneficial.

Further according to the present invention, there is provided a method for treating or preventing a psychotropic disorder or disease in a subject (e.g., a human being). The method is effected by administering a therapeutically effective amount of one or more of the chemical conjugates of the invention to a treated subject.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease, substantially ameliorating clinical symptoms of a disease or substantially preventing the appearance of clinical symptoms of a disease.

As used herein, the phrase "psychotropic disorder or disease" refers to a disorder or disease characterized by an impairment in the central nervous system. Examples of psychotropic disorders and diseases that are treatable using the chemical conjugates of the invention, include, without limitation, psychotic disorders or diseases, anxiety disorders, dissociative disorders, personality disorders, mood disorders, affective disorders, neurodegenerative diseases or disorders, convulsive disorders, boarder line disorders and mental diseases or disorders.

Representative examples of such psychotropic disorders or diseases include, without limitation, schizophrenia, paranoia, childhood psychoses, Huntington's disease, Gilles de la Tourette's syndrome, depression, manic depression, anxiety, Parkinson disease, Alzheimer disease and epilepsy.

The term "administering" as used herein refers to a method for bringing a chemical conjugate of the present invention into an area or a site in the brain that affected by the psychotropic disorder or disease.

The chemical conjugate of the present invention can be administered intraperitoneally. More preferably, it is administered orally.

The term "subject" refers to animals, typically mammals having a blood brain barrier, including human beings.

The term "therapeutically effective amount" refers to that amount of the chemical conjugate being administered which will relieve to some extent one or more of the symptoms of the psychotic disorder or disease being treated.

A therapeutically effective amount according to this method of the present invention preferably ranges between 0.5 mg/kg body and 50 mg/kg body, more preferably between 0.5 mg/kg body and 30 mg/kg body, more preferably between 0.5 mg/kg body and 20 mg/kg body and most preferably between 1 mg/kg body and 10 mg/kg body.

The present invention is thus directed to chemical conjugates which exert psychotropic activity. The chemical conjugates of the present invention are highly advantageous since they exert enhanced psychotropic activity and are further characterized by minimized adverse side effects induced thereby.

The term "side effects" as used herein refers to adverse symptoms that may develop as a result of administering to a subject a certain drug. Such symptoms may include, for example, extrapyramidal symptoms, as is detailed hereinabove, and are typically associated with the administration of psychotropic drugs.

Further according to the present invention, there is provided a method for treating or preventing a proliferative disorder or disease in a subject (e.g., a human being). The method is effected by administering a therapeutically effective amount of one or more of the chemical conjugates of the invention to a treated subject.

As used herein, the term "proliferative disorder or disease" refers to a disorder or disease characterized by cell proliferation. Cell proliferation conditions which may be prevented or treated by the present invention include, for example, malignant tumors such as cancer and benign tumors.

As used herein, the term "cancer" refers to various types of malignant neoplasms, most of which can invade surrounding tissues, and may metastasize to different sites, as defined by Stedman's medical Dictionary 25th edition (Hensyl ed., 1990). Examples of cancers which may be treated by the chemical conjugates of the present invention include, but are not limited to, brain and skin cancers. These cancers can be further broken down. For example, brain cancers include glioblastoma multiforme, anaplastic astrocytoma, astrocytoma, ependyoma, oligodendroglioma, medulloblastoma, meningioma, sarcoma, hemangioblastoma, and pineal parenchymal. Likewise, skin cancers include melanoma and Kaposi's sarcoma. Other cancerous diseases treatable using the chemical conjugates of the present invention include papilloma, blastoglioma, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, hepatocellular carcinoma, leukemia, lymphoma, Hodgkin's lymphoma and Burkitt's lymphoma.

Other, non-cancerous proliferative disorders are also treatable using the chemical conjugates of the present invention. Such non-cancerous proliferative disorders include, for example, stenosis, restenosis, in-stent stenosis, vascular graft restenosis, arthritis, rheumatoid arthritis, diabetic retinopathy, angiogenesis, pulmonary fibrosis, hepatic cirrhosis, atherosclerosis, glomerulonephritis, diabetic nephropathy, thrombic microangiopathy syndromes and transplant rejection.

As is demonstrated in the Examples section that follows, the chemical conjugates of the present invention exert high and potent anti-proliferative activity on a wide variety of cancer cells, including MDR cancer cells.

As is further demonstrated in the Examples section that follows, the chemical conjugates of the present invention further exert chemosensitization activity when used in combination with various chemotherapeutic drugs.

Hence, further according to the present invention there is provided a method of chemosensitization, as this term is defined hereinabove. The method is effected by administering to a subject a therapeutically effective amount of one or more chemotherapeutic agent(s) and a chemosensitizing effective amount of the chemical conjugate of the present invention.

As used herein, the phrase "chemosensitizing effective amount" describes an amount sufficient for measurable chemosensitization in the presence of therapeutic amounts of a chemotherapeutic agent.

This method is particularly useful in cases where the subject has MDR cancer such as, but not limited to, leukemia, lymphoma, carcinoma or sarcoma. According to the present invention the chemotherapeutic agent may be, for example, one of the following: an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Preferably, the chemotherapeutic agent is a nitrogen mustard, an epipodophyllotoxin, an antibiotic, or a platinum coordination complex. A more preferred chemotherapeutic agent is Cisplatin or Vincistine.

Thus, the present invention teaches novel chemical conjugates of psychotropic drugs, which exert higher psychotropic activity, substantially lower side effects and lower toxicity than the corresponding non-conjugated psychotropic drugs. These novel conjugates further exert anti-proliferative activity and chemosensitization activity and can be therefore beneficially used in the treatment of proliferative disorders either as prodrugs characterized by reduced side effects, low toxicity and high affinity toward brain cells or as chemosensitizers that are used in combination with chemotherapeutic drugs.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Chemical Syntheses and Analyses

Exemplary chemical conjugates of the present invention were synthesized by reacting the psychotropic agents perphenazine, fluphenazine and valproic acid with the short-chain fatty acids propionic acid, butyric acid and valeric acid and/or with 4-phenylbutyric acid and γ-aminobutyric acid (GABA). The compounds were prepared in high yields and were isolated as crystalline solids, soluble in aqueous 1% lactic acid.

Synthesis of chemical conjugates prepared from perphenazine or fluphenazine and an organic acid—General Procedure: A mixture of the neuroleptic agent perphenazine or fluphenazine (1 equivalent), an acyl chloride derivative of a short-chain fatty acid (1.1 equivalents) and, optionally, $Et_3N$ (2 equivalents) (used to free starting materials found as their HCl salts) in 5-10 ml dimethylformamide (DMF) was stirred at room temperature, under nitrogen atmosphere, for 24 hours. The mixture was then partitioned between ethyl acetate and water. The organic layer was thereafter washed with 5% $NaHCO_3$ and brine, dried over $MgSO_4$, filtered and evaporated, to give the desired product.

Synthesis of perphenazine 4-phenylbutyrate (AN 130): Perphenazine and 4-phenylbutyryl chloride (the acyl chloride of 4-phenylbutyric acid) were reacted as described above. The obtained crude residue was purified by silica gel chromatography, using a mixture of 1:10 methanol:ethyl acetate as eluent. The product was obtained as a yellow oil (78% yield).

$^1$H-NMR ($CDCl_3$): δ=1.94 (quint, J=6 Hz, 4H, $CO_2CH_2CH_2$, $ArNCH_2CH_2$), 2.32 (t, J=6 Hz, 2H, $CO_2CH_2$), 2.64 (m, 12H, six $NCH_2$), 3.93 (t, J=5.6 Hz, 2H, $ArNCH_2$), 4.17 (t, J=5.3 Hz, 2H, $NCH_2CH_2O$), 6.82-7.30 (m, 12H, Ar, Ph) ppm.

$^{13}$C-NMR ($CDCl_3$): δ=23.25 ($CH_2CH_2CO_2$), 26.46 ($ArNCH_2CH_2$), 33.56 ($CH_2Ph$), 35.06 ($CH_2CO_2$), 45.10 ($ArNCH_2$), 52.23 (two $NCH_2$), 52.72 (two $NCH_2$), 55.25 ($ArNCH_2CH_2$), 57.04 ($NCH_2CH_2O$), 61.32 ($NCH_2CH_2O$), 116.00 ($C_1$, $C_{10}$), 122.51 ($C_3$), 123.15 ($C_8$), 123.86 ($CH_2C(CH)_2$), 125.13 ($C_2$), 126.02 (p-Ph), 127.56 ($C_9$), 127.63 ($C_7$), 128.01 (o-Ph), 128.41 (m-Ph), 128.49 ($C_4$), 173.33 ($CO_2$) ppm.

MS (CI, i-Bu): m/z (%)=550 ($MH^+$, 1.7).

Synthesis of perphenazine butyrate (AN 167): Perphenazine and butyryl chloride (the acyl chloride of butyric acid) were reacted as described above. The product was obtained as a yellow oil (74% yield) and was used without further purification.

$^1$H-NMR ($CDCl_3$): δ=0.93 (t, J=7.36 Hz, 3H, Me), 1.63 (sext, J=7.44 Hz, 2H, $CH_2Me$), 1.95 (quint, J=6.7 Hz, 2H, $ArNCH_2CH_2$), 2.27 (t, J=7.46 Hz, 2H, $CO_2CH_2$), 2.43 (m, 10H, five $NCH_2$), 2.57 (t, J=5.96 Hz, 2H, $NCH_2CH_2O$), 3.66 (t, J=5.96 Hz, 2H, $ArNCH_2$), 4.18 (t, J=5.9 Hz, 2H, $NCH_2CH_2O$), 6.66 (m, 7H, Ar) ppm.

$^{13}$C-NMR ($CDCl_3$): δ=13.54 ($CH_3CH_2$), 18.29 ($MeCH_2$), 24.06 ($ArNCH_2CH_2$), 36.03 ($CH_2CO_2$), 45.15 ($ArNCH_2$), 53.09 (two $NCH_2$), 53.23 (two $NCH_2$), 55.30 ($ArNCH_2CH_2$), 56.51 ($NCH_2CH_2O$), 61.48 ($NCH_2CH_2O$), 115.64 ($C_1$, $C_{10}$), 122.02 ($C_3$), 122.69 ($C_8$), 123.27 ($C_5$), 124.52 ($C_6$), 127.23 ($C_7$), 127.29 ($C_9$), 127.68 ($C_4$), 133.00 ($C_2$), 144.32 ($C_{12}$), 146.29 ($C_{11}$), 173.37 ($CO_2$) ppm.

MS (CI, $NH_3$): m/z (%)=473 ($M^+$, 100), 474 ($MH^+$, 82.64).

Synthesis of perphenazine propionate (AN 177): Perphenazine and propionyl chloride (the acyl chloride of propionic acid) were reacted as described above. The product was obtained as a yellow oil (85% yield) and was used without further purification.

$^1$H-NMR ($CDCl_3$): δ=1.12 (t, J=7.53 Hz, 3H, Me), 1.95 (quint, J=6.8 Hz, 2H, $ArNCH_2CH_2$), 2.32 (q, J=7.57 Hz, 2H, $CO_2CH_2$), 2.51 (m, 10H, five $NCH_2$), 2.61 (t, J=5.95 Hz, 2H, $NCH_2CH_2O$), 3.89 (t, J=6.8 Hz, 2H, $ArNCH_2$), 4.16 (t, J=9.92 Hz, 2H, $NCH_2CH_2O$), 6.98 (m, 7H, Ar) ppm.

$^{13}$C-NMR ($CDCl_3$): δ=9.01 ($CH_3$), 24.08 ($ArNCH_2CH_2$), 27.44 ($CH_2CO_2$), 45.18 ($ArNCH_2$), 53.09 (two $NCH_2$), 53.26 (two $NCH_2$), 55.32 ($ArNCH_2CH_2$), 56.50 ($NCH_2CH_2O$), 61.63 ($NCH_2CH_2O$), 115.67 ($C_1$, $C_{10}$), 122.05 ($C_3$), 122.72 ($C_8$), 123.30 ($C_5$), 124.56 ($C_6$), 127.26 ($C_7$), 127.33 ($C_9$), 127.71 ($C_4$), 133.03 ($C_2$), 144.35 ($C_{12}$), 146.32 ($C_{11}$), 174.24 ($CO_2$) ppm.

MS ($C_1$, $NH_3$): m/z (%)=459 ($MH^+$, 100), 458 (M, 47.63).

Synthesis of perphenazine valerate (AN 178): Perphenazine and valeryl chloride (the acyl chloride of valeric acid) were reacted as described. The obtained crude residue was purified by silica gel chromatography, using a mixture of 7:4 ethyl acetate:hexane as eluent. The product was obtained as a yellowish oil (75% yield).

$^1$H-NMR ($CDCl_3$): δ=0.86 (t, J=7.23 Hz, 3H, Me), 1.29 (sext, J=6.97 Hz, 2H, $CH_2Me$), 1.56 (quint, J=7.09 Hz, 2H, $CH_2CH_2CO_2$), 1.87 (quint, J=6.79 Hz, 2H, $ArNCH_2CH_2$), 2.26 (t, J=7.64 Hz, 2H, $CH_2CO_2$), 2.37 (m, 10H, five $NCH_2$), 2.54 (t, J=5.93 Hz, 2H, $ArNCH_2$), 4.14 (t, J=5.95 Hz, 2H, $NCH_2CH_2O$), 6.53-7.14 (m, 7H, Ar) ppm.

$^{13}$C-NMR ($CDCl_3$): δ=13.51 ($CH_3CH_2$), 22.02 ($CH_2Me$), 23.89 ($CH_2CH_2Me$), 26.82 ($ArNCH_2CH_2$), 33.80 ($CH_2CO_2$), 45.07 ($ArNCH_2$), 53.00 (two $NCH_2$), 53.16 (two $NCH_2$), 55.09 ($ArNCH_2CH_2CH_2$), 56.46 ($NCH_2CH_2O$), 61.42 ($NCH_2CH_2O$), 111.68 (q, J=3.77 Hz, $C_1$), 115.73 ($C_{10}$), 118.74 (q, J=3.77 Hz, $C_3$), 122.85 ($C_8$), 123.77 ($C_6$), 124.02 (q, J=272 Hz, $CF_3$), 127.20 ($C_7$), 127.29 ($C_9$), 127.42 ($C_4$), 129.34 (q, J=32 Hz, $C_2$), 129.69 ($C_5$), 144.08 ($C_{11}$), 145.51 ($C_{12}$), 173.45 ($CO_2$) ppm.

MS (CI/$NH_3$): m/z (%)=522 ($MH^+$, 100).

Synthesis of fluphenazine propionate (AN 179): Fluphenazine and propionyl chloride (the acyl chloride of propionic acid) were reacted as described above. The product was obtained as a yellowish oil (95% yield) and as used without further purification.

$^1$H-NMR ($CDCl_3$): δ=1.12 (t, J=7.55 Hz, 3H, Me), 1.91 (quint, J=7.18 Hz, 2H, $ArNCH_2CH_2$), 2.32 (q, J=7.56 Hz, 2H, $CO_2CH_2$), 2.45 (m, 10H, five $NCH_2$), 2.59 (t, J=5.92 Hz, 2H, $NCH_2CH_2O$), 3.93 (t, J=7.12 Hz, 2H, $ArNCH_2$), 4.17 (t, J=5.95 Hz, 2H, $NCH_2CH_2O$), 6.67-7.14 (m, 7H, Ar).

$^{13}$C-NMR (CDCl$_3$): δ=8.91 (Me), 23.87 (ArNCH$_2$CH$_2$), 27.33 (CH$_2$CO$_2$), 45.05 (ArNCH$_2$), 52.98 (two NCH$_2$), 53.17 (two NCH$_2$), 55.07 (ArNCH$_2$CH$_2$CH$_2$), 56.42 (NCH$_2$CH$_2$O), 61.54 (NCH$_2$CH$_2$O), 111.65 (q, J=3 Hz, C$_1$), 115.71 (C$_{10}$), 118.73 (q, J=3.77 Hz, C$_3$), 122.84 (C$_8$), 123.73 (C$_6$), 123.99 (q, J=272 Hz, CF$_3$), 127.18 (C$_7$), 127.27 (C$_9$), 127.41 (C$_4$), 129.30 (q, J=32 Hz, C$_2$), 129.65 (C$_5$), 144.05 (C$_{11}$), 145.48 (C$_{12}$), 174.10 (CO$_2$).

MS (CI/NH$_3$): m/z (%)=494 (MH$^+$, 100).

Synthesis of fluphenazine butyrate (AN 180): Fluphenazine and butyryl chloride were reacted as described above. The product was obtained as a yellowish oil (97% yield) and was used without further purification.

$^1$H-NMR (CDCl$_3$): δ=0.93 (t, J=7.4 Hz, 3H, Me), 1.32 (sext, J=7.4 Hz, 2H, CH$_2$Me), 1.92 (quint, J=7.18 Hz, 2H, ArNCH$_2$CH$_2$), 2.27 (t, J=7.4 Hz, 2H, CO$_2$CH$_2$), 2.45 (m, 10H, five NCH$_2$), 2.58 (t, J=5.9 Hz, 2H, NCH$_2$CH$_2$O), 3.93 (t, J=7.2 Hz, 2H, ArNCH$_2$), 4.17 (t, J=5.98 Hz, 2H, NCH$_2$CH$_2$O), 6.67-7.13 (m, 7H, Ar) ppm.

$^{13}$C-NMR (CDCl$_3$): δ=13.42 (CH$_3$CH$_2$), 18.20 (MeCH$_2$), 23.85 (ArNCH$_2$CH$_2$), 35.92 (CH$_2$CO$_2$), 45.02 (ArNCH$_2$), 52.97 (two NCH$_2$), 53.14 (two NCH$_2$), 55.04 (ArNCH$_2$CH$_2$CH$_2$), 56.43 (NCH$_2$CH$_2$O), 61.39 (NCH$_2$CH$_2$O), 111.62 (q, J=3 Hz, C$_1$), 115.68 (C$_{10}$), 118.68 (q, J=3.77 Hz, C$_3$), 122.80 (C$_8$), 123.70 (C$_6$), 123.98 (q, J=272 Hz, CF$_3$), 127.15 (C$_7$), 127.24 (C$_9$), 127.38 (C$_4$), 129.27 (q, J=32 Hz, C$_2$), 129.62 (C$_5$), 144.03 (C$_{11}$), 145.46 (C$_{12}$), 173.23 (CO$_2$) ppm.

MS (CI/CH$_4$): m/z (%)=507.18 (M$^+$, 75.3), 508.18 (MH$^+$, 57.57), 419.13 (M-C$_4$H$_8$O$_2$, 82).

Synthesis of fluphenazine valerate (AN 181): Fluphenazine and valeryl chloride (the acyl chloride of valeric acid) were reacted as described. The obtained crude residue was purified by silica gel chromatography, using a mixture of 7:4 ethyl acetate:hexane as eluent. The product was obtained as a yellowish oil (75% yield).

$^1$H-NMR (CDCl$_3$): δ=0.86 (t, J=7.23 Hz, 3H, Me), 1.29 (sext, J=6.97 Hz, 2H, CH$_2$Me), 1.56 (quint, J=7.09 Hz, 2H, CH$_2$CH$_2$CO$_2$), 1.87 (quint, J=6.79 Hz, 2H, ArNCH$_2$CH$_2$), 2.26 (t, J=7.64 Hz, 2H, CH$_2$CO$_2$), 2.37 (m, 10H, five NCH$_2$), 2.54 (t, J=5.93 Hz, 2H, ArNCH$_2$), 4.14 (t, J=5.95 Hz, 2H, NCH$_2$CH$_2$O), 6.53-7.14 (m, 7H, Ar).

$^{13}$C-NMR (CDCl$_3$): δ=13.51 (Me), 22.02 (CH$_2$Me), 23.89 (CH$_2$CH$_2$Me), 26.82 (ArNCH$_2$CH$_2$), 33.80 (CH$_2$CO$_2$), 45.07 (ArNCH$_2$), 53.00 (two NCH$_2$), 53.16 (two NCH$_2$), 55.09 (ArNCH$_2$CH$_2$CH$_2$), 56.46 (NCH$_2$CH$_2$O), 61.42 (NCH$_2$CH$_2$O), 111.68 (q, J=3.77 Hz, C$_1$), 115.73 (C$_{10}$), 118.74 (q, J=3.77 Hz, C$_3$), 122.85 (C$_8$), 123.77 (C$_6$), 124.02 (q, J=272 Hz, CF$_3$), 127.20 (C$_7$), 127.29 (C$_9$), 127.42 (C$_4$), 129.34 (q, J=32 Hz, C$_2$), 129.69 (C$_5$), 144.08 (C$_{11}$), 145.51 (C$_{12}$), 173.45 (CO$_2$).

MS (CI/NH$_3$): m/z (%)=522 (MH$^+$, 100).

Synthesis of chemical conjugates prepared form perphenazine or fluphenazine and amino organic acids—general procedure: A mixture of an N-protected amino acid (1 equivalent) and carbonyl diimidazole (CDI) (1.1 equivalents) in 5-10 ml DMF was stirred, under nitrogen atmosphere, for 1 hour. Perphenazine or Fluphenazine (1 equivalent) was added thereafter and the mixture was stirred under nitrogen atmosphere, at 90° C., for 24 hours. The resulting slurry was evaporated and partitioned between ethyl acetate and water. The aqueous phase was extracted twice with ethyl acetate and the combined organic layer was washed trice with NaHCO$_3$, twice with brine, dried over MgSO$_4$, filtered and evaporated. The N-protected product was obtained as a yellowish oil.

The N-protecting group was removed from the product as follows: To a solution of the N-protected product in ethyl acetate, a solution of 4N HCl in ethyl acetate was added dropwise. The mixture was stirred for 2 hours at room temperature. The solvent was thereafter evaporated and the residue was further dried under high vacuum. The obtained product, as a trihydrochloride salt, was recrystallized from a mixture of methanol/ether, filtered and dried.

Synthesis of perphenazine N-boc-4-aminobutyrate: Perphenazine and N-t-boc-GABA (N-t-boc-protected 4-aminobutyric acid) were reacted as described above. The crude product was purified by silica gel chromatography, using a mixture of 20:1 ethyl acetate:ethanol as eluent. The product was obtained as a yellowish oil (63% yield).

$^1$H-NMR (CDCl$_3$): δ=1.43 (s, 9H, t-Bu), 1.82 (quint, J=7.18 Hz, 2H, CH$_2$CH$_2$NHBoc), 1.90 (quint, J=7.18 Hz, 2H, ArNCH$_2$CH$_2$), 2.35 (t, J=8.97 Hz, 2H, CO$_2$CH$_2$), 2.42 (m, 10H, five NCH$_2$), 2.60 (t, J=5.98 Hz, 2H, NCH$_2$CH$_2$O), 3.16 (q, J=6.85 Hz, 2H, CH$_2$NHBoc), 3.84 (t, J=7.2 Hz, 2H, ArNCH$_2$), 4.18 (t, J=5.98 Hz, 2H, NCH$_2$CH$_2$O), 5.10 (bs, 1H, NH), 6.83 (m, 7H, Ar) ppm.

$^{13}$C-NMR (CDCl$_3$): δ=23.92 (CH$_2$CH$_2$NHBoc), 24.98 (ArNCH$_2$CH$_2$), 28.21 (t-Bu), 39.50 (CH$_2$CO$_2$), 45.05 (ArNCH$_2$), 52.89 (two NCH$_2$), 53.03 (two NCH$_2$), 55.15 (ArNCH$_2$CH$_2$CH$_2$), 56.34 (NCH$_2$CH$_2$O), 60.13 (CH$_2$NHBoc), 61.29 (NCH$_2$CH$_2$O), 78.80 (CMe$_3$), 115.60 (C$_1$, C$_{10}$), 121.96 (C$_3$), 122.65 (C$_8$), 123.22 (C$_5$), 124.45 (C$_6$), 127.21 (C$_7$, C$_4$), 127.62 (C$_9$), 132.93 (C$_2$), 144.23 (C$_{12}$), 146.23 (C$_{11}$), 155.79 (NCO$_2$), 172.92 (CO$_2$) ppm.

Synthesis of Fluphenazine N-boc-4-aminobutyrate: Fluphenazine and N-t-boc-GABA (N-t-boc-protected 4-aminobutyric acid) were reacted as described above. The crude product was purified by silica gel chromatography, using a mixture of 20:1 ethyl acetate:ethanol as eluent. The product was obtained as a yellowish oil (75% yield).

$^1$H-NMR (CDCl$_3$): δ=1.49 (s, 9H, t-Bu), 1.77 (quint, J=6.38 Hz, 2H, CH$_2$CH$_2$NHBoc), 1.90 (quint, J=6.96 Hz, 2H, ArNCH$_2$CH$_2$), 2.35 (t, J=6.38 Hz, 2H, CO$_2$CH$_2$), 2.45 (m, 10H, five NCH$_2$), 2.58 (t, J=5.8 Hz, 2H, NCH$_2$CH$_2$O), 3.14 (q, J=5.8 Hz, 2H, CH$_2$NHBoc), 3.94 (t, J=6.38 Hz, 2H, ArNCH$_2$), 4.2 (t, J=5.8 Hz, 2H, NCH$_2$CH$_2$O), 4.92 (bs, 1H, NH), 6.8-7.2 (m, 7H, Ar) ppm.

$^{13}$C-NMR (CDCl$_3$): δ=23.88 (CH$_2$CH$_2$NHBoc), 25.07 (ArNCH$_2$CH$_2$), 28.28 (t-Bu), 39.60 (CH$_2$CO$_2$), 45.13 (ArNCH$_2$), 52.94 (two NCH$_2$), 53.04 (two NCH$_2$), 55.13 (ArNCH$_2$CH$_2$CH$_2$), 56.43 (NCH$_2$CH$_2$O), 60.22 (CH$_2$NHBoc), 61.36 (NCH$_2$CH$_2$O), 78.92 (CMe$_3$), 111.77 (q, J=3 Hz, C$_1$), 115.82 (C$_{10}$), 118.85 (q, J=3.77 Hz, C$_3$), 122.97 (C$_8$), 123.91 (C$_6$), 124.05 (q, J=272 Hz, CF$_3$), 127.30 (C$_7$), 127.39 (C$_9$), 127.52 (C$_4$), 129.42 (q, J=32 Hz, C$_2$), 129.82 (C$_5$), 144.12 (C$_{11}$), 145.58 (C$_{12}$), 155.82 (NCO$_2$), 173.01 (CO$_2$) ppm.

Synthesis of perphenazine 4-aminobutyrate trihydrochloride (AN 168): Perphenazine N-boc-4-aminobutyrate, prepared as described above, was reacted with HCl as described above. The trihydrochloride product was obtained as a viscous semi-solid oil (quantitative yield).

$^1$H-NMR (CDCl$_3$): δ=1.93 (quint, J=7.14 Hz, 2H, CH$_2$CH$_2$NH$_2$), 2.23 (m, 2H, ArNCH$_2$CH$_2$), 2.61 (t, J=7.14 Hz, 2H, CO$_2$CH$_2$), 3.01 (m, 2H, CH$_2$NH$_2$), 3.33 (m, 2H, ArNCH$_2$CH$_2$), 3.48-3.87 (m, 10H, five NCH$_2$), 4.10 (t, J=6.4 Hz, 2H, NCH$_2$CH$_2$O), 4.48 (m, 2H, ArNCH$_2$), 7-7.31 (m, 7H, Ar) ppm.

$^{13}$C-NMR (CDCl$_3$): δ=22.34 (CH$_2$CH$_2$NH$_2$), 22.93 (ArNCH$_2$CH$_2$), 31.11 (CH$_2$CO$_2$), 39.56 (CH$_2$NH$_2$), 44.76

(ArNCH$_2$), 49.42 (two NCH$_2$), 49.61 (two NCH$_2$), 55.29 (ArCH$_2$CH$_2$CH$_2$), 56.08 (NCH$_2$CH$_2$O), 58.64 (NCH$_2$CH$_2$O), 116.69 (C$_{10}$), 117.20 (C$_1$), 123.49 (C$_3$), 124.19 (C$_8$), 125.44 (C$_5$), 126.42 (C$_6$), 128.20 (C$_7$), 128.56 (C$_9$), 128.80 (C$_4$), 134.23 (C$_2$), 144.97 (C$_{12}$), 147.37 (C$_{11}$), 173.04 (CO$_2$) ppm.

MS (CI/CH$_4$): m/z (%)=403.09 (MH$^+$-C$_4$H$_7$NO, 100), 489.18 (MH$^+$, 1.7).

Synthesis of fluphenazine 4-aminobutyrate trihydrochloride (AN 187): Fluphenazine N-boc-4-aminobutyrate was reacted with HCl, as described above. The product was obtained as a white solid (75% yield).

$^1$H-NMR (CDCl$_3$): δ=1.93 (quint, J=7.25 Hz, 2H, CH$_2$CH$_2$NH$_2$), 2.29 (quint, J=5.42 Hz, 2H, ArNCH$_2$CH$_2$), 2.49 (t, J=7.14 Hz, 2H, CO$_2$CH$_2$), 2.99 (t, J=7.54 Hz, 2H, CH$_2$NH$_2$), 3.39 (t, J=4.87 Hz, 2H, ArNCH$_2$CH$_2$CH$_2$), 3.40 (t, J=5.42 Hz, 2H, NCH$_2$CH$_2$N), 3.4-4.0 (m, 8H, four NCH$_2$), 3.91 (m, 2H, NCH$_2$CH$_2$O), 4.18 (t, J=6.12 Hz, 2H, ArNCH$_2$), 7.02-7.33 (m, 7H, Ar) ppm.

$^{13}$C-NMR (CDCl$_3$): δ=22.76 (ArNCH$_2$CH$_2$), 23.36 (CH$_2$CH$_2$NH$_2$), 31.49 (CH$_2$CO$_2$), 39.96 (CH$_2$NH$_2$), 45.21 (ArNCH$_2$), 49.57 (two NCH$_2$), 50.02 (two NCH$_2$), 55.72 (ArNCH$_2$CH$_2$), 56.48 (NCH$_2$CH$_2$O), 58.99 (NCH$_2$CH$_2$O), 113.41 (q, J=3.77 Hz, C$_1$), 117.80 (C$_{10}$), 120.70 (q, J=3.77 Hz, C$_3$), 124.89 (C$_8$), 126.24 (C$_6$), 125.59 (q, J=272 Hz, CF$_3$), 128.75 (C$_7$), 128.97 (C$_9$), 129.25 (C$_4$), 130.96 (q, J=32 Hz, C$_2$), 132.51 (C$_5$), 145.12 (C$_{11}$), 147.25 (C$_{12}$), 173.48 (CO$_2$) ppm.

MS (CI/CH$_4$): m/z (%)=523 (MH$^+$, 0.5), 280 (M-C$_{14}$H$_9$NF$_3$S, 100).

Synthesis of chemical conjugates prepared from valproic acid and organic acids or amino organic acids—general procedure:

Valproic acid is reacted with chloromethyl chlorosulfate (1.2 equivalents), in the presence of NaHCO$_3$, Bu$_4$N$^+$HSO$_4^-$, water and CH$_2$Cl$_2$ at room temperature. The aqueous phase is thereafter separated and washed with CH$_2$Cl$_2$. The organic phase is washed with a saturated aqueous solution of NaHCO$_3$, brine, dried (MgSO$_4$) and is evaporated to give the chloromethyl ester of valproic acid as a residual oil, which is purified by distillation. The valproic acid chloromethyl ester is then reacted with an organic acid or with an N-protected amino organic acid, similarly to the general procedures described above, to thereby yield the desired product.

Synthesis of 2-Propyl-pentanoic acid (valproic acid) chloromethyl ester (AN-215): To a mixture of valproic acid (2.76 grams, 19 mmol), NaHCO$_3$ (5.75 grams, 68.4 mmol), Bu$_4$N$^+$HSO$_4^-$ (0.5 gram), water (25 ml) and CH$_2$Cl$_2$ (25 mL), chloromethyl chlorosulfate (3.79 grams, 23 mmol, 1.2 equivalents) was added. The mixture was stirred at room temperature overnight. The aqueous layer was thereafter separated and was washed with CH$_2$Cl$_2$. The organic layer was washed consecutively with a saturated aqueous solution of NaHCO$_3$ and brine, dried (MgSO$_4$) and evaporated, to give a residual oil, which was purified by distillation (b.p. 70° C./4 mm Hg), to give 2.05 grams (56% yield) of AN-215.

$^1$H NMR (CDCl$_3$): δ=0.92 (t, J=7.3 Hz, 6H, two CH$_3$), 1.26-1.66 (m, 8H, two CH$_2$CH$_2$), 2.36-2.48 (m, 1H, CH), 5.71 (s, 2H, OCH$_2$Cl).

$^{13}$C NMR (CDCl$_3$): δ=13.9 (two CH$_3$), 20.4 (MeCH$_2$CH$_2$), 34.3 (two CH$_2$CH), 45.0 (CH), 68.5 (OCH$_2$Cl), 174.4 (CO$_2$).

MS (EI): m/z (%)=193 (MH$^+$, 100), 150 (MH$^+$-C$_3$H$_7$).

Synthesis of 2-Propyl-pentanoic acid (valproic acid) N-boc-4-aminobutyryloxymethyl ester (AN-217): A mixture of N-t-boc-GABA (N-t-boc-protected 4-aminobutyric acid) (1.78 grams, 8.8 mmol) and 2-propyl-pentanoic acid chloromethyl ester (1.8 grams, 8.27 mmol) in dry ethyl methyl ketone, was stirred under nitrogen atmosphere. Et$_3$N (1 gram, 9.5 mmol) was added dropwise and the reaction mixture was heated for 60 hours. The obtained white precipitate was filtered and the filtrate was evaporated. The residue was dissolved in ethyl acetate, washed consecutively with saturated aqueous NaHCO$_3$ and brine, dried (MgSO$_4$), filtered, evaporated and further dried under high vacuum to give the product as an oil (1.7 grams, 57% yield), which was used subsequently without further purification.

$^1$H-NMR (CDCl$_3$): δ=0.80 (t, J=7.1 Hz, 6H, two CH$_3$), 1.19-1.72 (s+m, 17H, two CH$_2$CH$_2$Me+t-Bu), 1.82 (q, J=7.1 Hz, 2H, CH$_2$CH$_2$CH$_2$), 2.36-2.43 (m, 3H, CH$_2$CO +CHCO), 3.16 (t, J=6.8 Hz, 2H, NHCH$_2$), 4.74 (bs, 1H, NH), 5.75 (s, 2H, OCH$_2$O).

$^{13}$C-NMR (CDCl$_3$): δ=18 (two CH$_3$), 23 (two MeCH$_2$), 25 (CH$_2$CH$_2$CH$_2$), 28.2 (Me$_3$C), 31.1 (COCH$_2$), 34.1 (two CH$_2$CH), 39.6 (NHCH$_2$), 44.81 (CH), 79 (OCH$_2$O), 155.8 (NHCO$_2$), 171.7 (CH$_2$CO), 175 (CHCO$_2$).

MS (ES$^+$): m/z (%)=382 (M+Na$^+$, 65), 360 (MH$^+$, 100), 304 (MH$^+$-C$_4$H$_8$, 98).

Synthesis of 2-Propyl-pentanoic acid (valproic acid) 4-aminobutyryloxymethyl ester hydrochloride (AN-216): To a solution of 2-propyl-pentanoic acid N-t-boc-4-amino-butyryloxymethyl ester (AN-217, prepared as described hereinabove) (1.7 grams, 4.7 mmol) in ethyl acetate, a solution of 4N HCl in ethyl acetate was added. The obtained mixture was stirred for 4 hours at room temperature, the solvent was thereafter evaporated and the residue was further dried under high vacuum. The residue was dissolved in ether, and addition of hexane lead to precipitation of the desired product AN-216 (0.75 gram, 62%) as an amorphous solid having a melting point of 35-37° C.

$^1$H-NMR (CD$_3$OD): δ=0.9 (t, J=7.1 Hz, 6H, two CH$_3$), 1.2-1.64 (m, 8H, two CH$_2$CH$_2$Me), 1.95 (q, J=7.5 Hz, 2H, CH$_2$CH$_2$CH$_2$), 2.4-2.5 (m, 1H, CHCO), 2.53 (t, J=7.2 Hz, 2H, CH$_2$CO), 2.99 (t, J=7.2 Hz, 2H, CH$_2$N), 5.77 (s, 2H, OCH$_2$O).

$^{13}$C-NMR (CD$_3$OD): δ=14.2 (two CH$_3$), 21.5 (two MeCH$_2$), 23.5 (CH$_2$CH$_2$CH$_2$), 31.3 (COCH$_2$), 35.5 (two CH$_2$CH), 39.9 (NCH$_2$), 46.2 (CH), 80.6 (OCH$_2$O), 172.5 (CH$_2$CO), 176.4 (CHCO$_2$).

MS (CI/NH$_3$): m/z (%)=260 (MH$^+$, 100).

Table 1 below presents the chemical conjugates synthesized by the methods described hereinabove.

TABLE 1
AN-130  Perphenazine 4-Phenylbutyrate
C$_{31}$H$_{36}$ClN$_3$O$_2$S
550.16
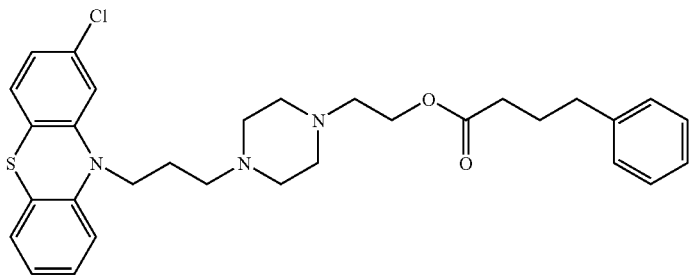
AN-167  Perphenazine Butyrate
C$_{25}$H$_{32}$ClN$_3$O$_2$S
474.06
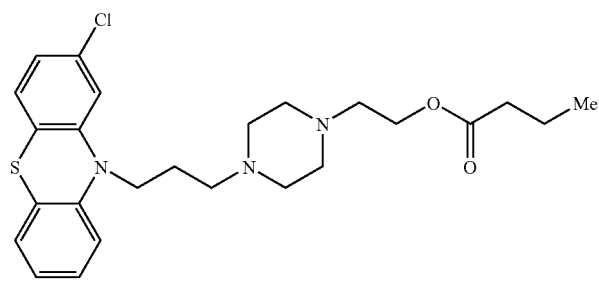
AN-168  Perphenazine 4-aminobutyrate
Trihydrochloride
C$_{25}$H$_{33}$ClN$_4$O$_2$S•3HCl
598.46
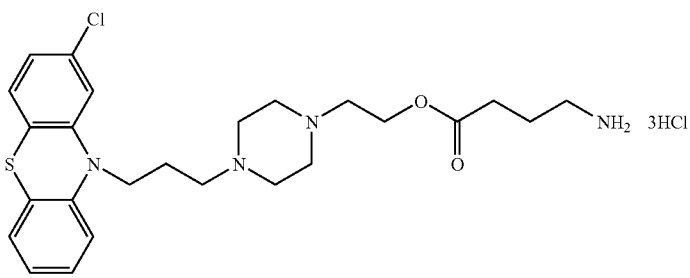
AN-177  Perphenazine Propionate
C$_{24}$H$_{30}$ClN$_3$O$_2$S
460.03
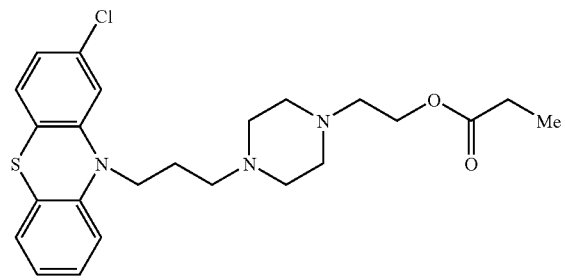
AN-178  Perphenazine Valerate
C$_{26}$H$_{34}$ClN$_3$O$_2$S
488.09
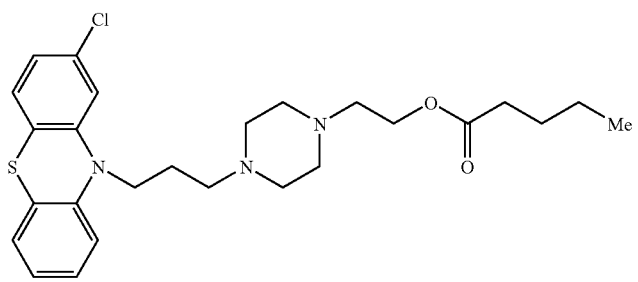

TABLE 1-continued

| | | |
|---|---|---|
| AN-180 | Fluphenazine Butyrate<br>C$_{26}$H$_{32}$F$_3$N$_3$O$_2$S<br>507.61 | 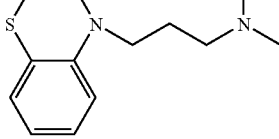 |
| AN-179<br>(NSK-I-52) | Fluphenazine Propionate<br>C$_{25}$H$_{30}$F$_3$N$_3$O$_2$S<br>493.59 | 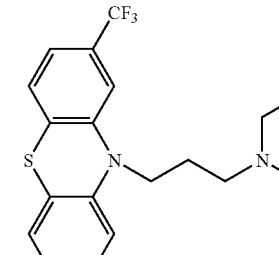 |
| AN-181<br>(NSK-I-42) | Fluphenazine Valerate<br>C$_{27}$H$_{34}$F$_3$N$_3$O$_2$S<br>521.64 | 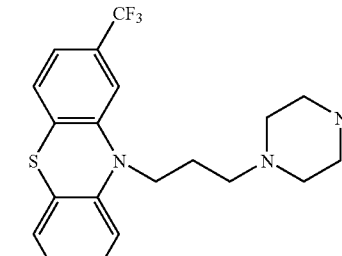 |
| AN-187 | fluphenazine 4-Aminobutyrate<br>Trihydrochloride<br>C$_{26}$H$_{33}$F$_3$N$_4$O$_2$S•3HCl<br>632.01 | 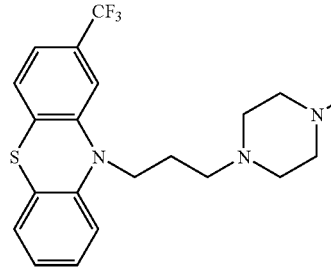 |
| AN-216 | 2-Propyl-pentanoic acid 4-amino-butyryloxymethyl ester hydrochloride | 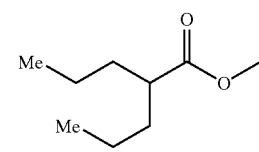 |

Activity Assays

Materials and Experimental Methods

Cell lines: Human prostate carcinoma (PC-3), human colon carcinoma (HT-29), murine melanoma (B-16) and its drug resistant subclone (B-16 MDR), mouse fibroblasts (3T3), myeloid leukemia (HL 60) and its drug resistant subclone (HL 60 MX2), endometrium cell line (MES SA) and its drug resistant subclone (MES DX5), jurkat T lymphoma and monocyte leukemia (U-937), were used in this study.

The primary cultures of rat fibroblasts were obtained from neonatal rats using known procedures [7].

Neuron cells and glia cells were prepared from pregnant (days 14-15) ICR mice embryo brains. The brains were dissected and homogenized in a mixture of Leibowitch L-15 medium (Beth Aemek), 75 □g/ml gentamycin and 0.2 mM glutamin. The cells, 300-500K/well, were seeded in poly-D-lysine-treated 96 well microplates. The selected neuronal culture was obtained by adding, 48 hours thereafter, 5-fluorodeoxyuridine (FUDR) and uridine to half of the plates. The untreated cultures included a mixture on neuronal and glial cells. The cells were grown in RPMI or DMEM medium supplemented with 10% FCS (fetal calf serum) and with 2 mM glutamine and were incubated at 37° C. in a humidified 5% $CO_2$ incubator.

Rat myocytes culture was prepared from 1-2 day old Wistar newborn rats (Harlan). Thirty newborn rats were used for obtaining about 25-30 million cells. To this end, the hearts were dissected and were tissue-dissociated enzymatically at room temperature using RDB™ (a protease isolated from fig tree extract). This protocol was repeated five times, until the cells were completely dispersed. The dispersed cells were pre-plated in tissue culture flasks, $3 \times 10^6$/ml in DMEM medium, for 45 minutes, and were then transferred to a gelatin coated microtiter plate for 24 hours, in order to reduce non myocytic cells. The cytotoxic agent ARO-C was thereafter added to the culture, to thereby eliminate dividing cells and leave only the undividing myocytes in the culture. The cells were incubated for 4 days and microscopic inspection was performed thereafter.

Proliferation of cancer and normal cells: Proliferation was measured by neutral red assay [8] or by a fluorometric assay quantitating DNA content [9]. In the neutral red assay, the neutral red is absorbed by lysosomes, thus causing coloring of living cells. Quantitative analysis is performed by colorimetric assay (ELISA reader at 550 nm). In the fluorometric assay, alamar blue is used as a redox indicator. Alamar blue fluorescence was measured at an excitation wavelength of 544 nm and an emission wavelength of 590 mm (FLUOstar BMG Lab Technologies, Offenburg, Germany).

Apoptosis and DNA fragmentation: Fragmentation of cell nuclei was studied by flow cytometric analysis of propidium iodide-stained cells. This analysis was performed using a FACScan (Becton Dickinson, Mountain View, Calif.) equipped with an argon ion laser adjusted to an excitation wavelength of 480 nm and with a Doublet Discrimination Module (DDM). Lysis II (Becton Dickinson) software was used for data acquisition. Apoptotic nuclear changes were evaluated according to the criteria of Nicolletti et al. [13].

Chemosensitization: The chemosensitizing effect of perphenazine and its chemical conjugate AN 168 was measured in vitro. Various concentrations of perphenazine or AN 168 were co-administered together with a chemotherapeutic agent to either C6 rat glioma cells or to Jurkat T lymphoma cells. Cells viability and/or DNA fragmentation following treatment with either the chemotherapeutic agent, perphenazine, AN 168, a combination of the chemotherapeutic agent and perphenazine or a combination of a chemotherapeutic agent with AN 168 were measured as described hereinabove.

Animals: Young adult male rats (150-230 grams) were purchased from Harlan (Israel). Animals were divided 2-5/cage and housed in controlled conditions in the animal room for a week prior to the experiments. The experiments were conducted with naive animals, in a double blind procedure. In each experiment various treatment groups (about 5-10 animals each) were tested.

Young adult male and female mice were purchased from Harlan, Israel. The animals were housed for 4-7 days under controlled conditions prior to experimentation. Experiments were conducted in a double blind procedure. In each experiment various treatment groups (about 10 animals each) were tested.

Catalepsy in rats: The manifestation of the extrapyramidal adverse effects induced by typical neuroleptics was evaluated by the appearance of stereotypic cataleptic behavior in rats following the neuroleptic treatment. Catalepsy was determined by two methods: (i) by measuring the time it took an animal hanging on a cage wall to move its hind legs and reach a flat surface (the "wall" test); and (ii) rats were placed on a flat surface with their anterior limbs leaning on a flat bar (5.5 cm height) resembling a piano playing position. Catalepsy was determined by the time it took an animal to descend and reach the flat surface (the "piano" test). The maximum time of follow up was 2 minutes and these measurements were performed hourly and individually for each animal. These tests provide an assessment of central dopamine (DA) blocking activity and are acceptable criteria for extrapyramidal symptoms induced by anti-psychotic drugs [10]. The total induced catalepsy and the time course thereof were measured for perphenazine, fluphenazine and for compounds AN 167, AN 168, AN 177, AN 178, AN 180 and AN 187 (see Table 1 hereinabove), comparing different sets of compounds and different conditions. Generally, 5 mg/Kg of the parent drug perphenazine and 7.5 mg/Kg fluphenazine and equimolar doses of their related chemical conjugates of the present invention, dissolved in 1% lactic acid, were injected to the animals intraperitoneally. In a different set of measurements, AN 168 and perphenazine, dissolved in 1% lactic acid, were orally administered to the animals.

Catalepsy in mice: The appearance of stereotypic cataleptic behavior in mice following the neuroleptic treatment was measured in two different sets of experiments.

In the first set, adult males were divided into groups and each group was treated by either perphenazine (1.5 mg/kg, 9 mice), a mixture of perphenazine and an equimolar dose of GABA (7 mice), an equimolar dose of AN-168 (8 mice) or by no treatment (control group, 6 mice). The catalepsy was determined using a system of two cages and a bar therebetween. The mouse was hung in the middle of the bar, and the percentage of animals reaching the target within 2 minutes was monitored 1 hour, 2 hours and 3 hours following the treatment.

In the second set, young females were divided into groups and each group was treated by either 2.5 mg/kg perphenazine (6 mice), a mixture of perphenazine and an equimolar dose of GABA (6 mice), an equimolar dose of AN-168 (7 mice) or by no treatment (control group, 7 mice). The catalepsy was determined using the system described hereinabove. The mouse was hung in the middle of the bar, and the time it took the animal to reach the target was measured.

Prolactin secretion: Typical neuroleptics induce hyperprolactinemia, which is frequently associated with gallactorehea and impaired gonadal and sexual function [11]. The measurement of the circulatory plasma prolactin level was therefore used as a sensitive biochemical marker for the psychotropic activity of the known neuroleptics and the chemical conjugates of the present invention, following intraperitoneal or oral administration thereof. Thus, blood was collected from the punctured eye orbital of rats under ether anesthesia and the assay was performed using Millennia, rat prolactin enzyme immunometric assay-kit (DPC, USA).

Behavioral criteria: Sedation of the animals treated by the chemical conjugates of the present invention was observed and scored as described bellow (Table 2). The degree of animal sedation and mobility in the various treated groups was evaluated using a score of from 0 to 3, while a score of 0 represents active and mobile animals, a score of 1 represents calm and mobile animals, a score of 2 represents calm and immobile animals and a score of 3 represents completely ataxic and non-alert animals. The behavior of the treated animals provided an estimation of the neuroleptic efficacy of the tested known neuroleptics and of the chemical conjugates, as well as the severity of the extrapyramidal symptoms induced thereby.

Toxicity: In vitro toxicity was determined by measuring the effect of the tested compounds (either known neuroleptics or the chemical conjugates of the invention) on primary cultures of neurons and whole brain neuron and glia cells obtained from the brains of neonatal mice. In vitro toxicity of perphenazine and its chemical conjugate AN 168 was also determined with rat myocytes. Acute toxicity in vivo as determined by the $LD_{50}$ was evaluated on 2 months old ICR mice following the administration of a single intraperitoneal bolus-dose of drug.

D-Amphetamine-induced hyperactivity in rats: The efficacy of the chemical conjugates of the present invention was studied using the D-amphetamine-induced hyperactivity and motility model, which is known as one of the most established animal models for schizophrenia [14].

Naïve Wistar male rats were placed in individual boxes. In each experiment 4 rats were studied. Perphenazine or equimolar doses of its chemical conjugate AN-168 were administered intraperitoneally (ip) to the rats 30 minutes prior to intraperitoneal administration of amphetamine (2.5 mg/kg), or 90 minutes prior to oral administration of amphetamine (2.5 mg/kg). The animals locomotor activity was assessed using two parameters: climbing attempts of the animal on the barrel walls (as big movements) and head movement of the animal (as small movements). Assessment was recorded every 15 minutes for two hours. Each animal was tested at each time point for 120 seconds.

Experimental Results

Induced-catalepsy and psychotropic activity of perphenazine and chemical conjugates containing same: The induced catalepsy and psychotropic activity of 5 mg/kg perphenazine and equimolar concentrations of its chemical conjugates AN 130, AN 167 and AN 168 (see Table 1 hereinabove) was measured by intraperitoneally injecting the compounds, dissolved in 1% lactic acid, to young adult Wistar male rats (weighing 150-200 grams), divided 5 per cage and was determined by the "wall" test described hereinabove. A control animals group was treated with the vehicle (lactic acid) only. The effects of the treatment on both catalepsy and prolactin secretion were followed for a period of 2 hours and the results are presented in FIGS. 1a and 1b.

FIG. 1a shows the data obtained for induced catalepsy as the sum of 3 determinations that were carried out in duplicates at 0, 60 and 120 minutes after the treatment. Each column depicts averages of 5 animals. The total time was normalized to perphenazine (e.g., 100%). The obtained data show that catalepsy was induced by the treatment of perphenazine and AN 130 while AN 167 and AN 168 did not induce catalepsy at all.

FIG. 1b shows the prolactin blood level measured at 0, 60 and 120 minutes after the treatment and represents the sum of three determinations at each time reference. The prolactin blood level serves as a biochemical marker for the psychotropic activity of the compounds. The obtained data show similar profiles of the prolactin blood level in the animals when treated with perphenazine, AN 130, AN 167 or AN 168, which peaked at 60 minutes and decreased thereafter. The prolactin blood levels, at each time point, in the animals treated with the chemical conjugates AN 130, AN 167 and AN 168 was similar to that of perphenazine, indicating that the psychotropic activity of the chemical conjugates is similar to that of the parent drug. In the control animals, treated with the vehicle (1% lactic acid) only, the level of prolactin was unchanged.

SAR (Structure Activity Relationship) studies: SAR studies were performed for perphenazine and the chemical conjugates including same. The induced catalepsy was measured as described hereinabove and was determined by the "wall" test. The results are presented in FIG. 2. The conjugate of perphenazine and GABA, AN 168, was found to be the most effective, resulting with almost maximal reduction of induced catalepsy, followed by the valerate containing conjugate AN178, the propionate containing conjugate AN177 and the butyrate containing conjugate AN167. This experiment shows a significant reduction of the induced catalepsy following treatment with the chemical conjugates as compared with the catalepsy induced by treatment with perphenazine per se.

Catalepsy and animal behavior induced by perphenazine, fluphenazine and chemical conjugates containing same: Perphenazine, fluphenazine and the butyric acid- and GABA-containing chemical conjugates thereof (AN 167, AN 168, AN 180 and AN 187, see Table 1) were tested for the total catalepsy induced thereby, the time course of the induced catalepsy and animal behavior following the administration thereof. The measurements were performed following intraperitoneal injections of 5 mg/Kg perphenazine, equimolar concentrations of AN 167 and AN 168, 7.5 mg/Kg fluphenazine and equimolar concentrations of AN 180 and AN 187. The catalepsy was determined by the "wall" test.

FIG. 3a demonstrates the total catalepsy induced by the tested compounds. The obtained data is a sum of determinations taken at 0, 30, 60, 90, 120, 180, 240 and 420 minutes following administration, with total time normalization to perphenazine and fluphenazine (=100%). Both the butyric acid containing chemical conjugates, AN 167 and AN 180, reduced catalepsy significantly. The GABA containing conjugates of perphenazine, AN168, abolished it, while the GABA conjugate of fluphenazine, AN187, reduced it considerably.

FIG. 3b shows the prolactin blood level measured at 0, 60 and 120 minutes after treatment with perphenazine, its GABA conjugate AN 168, fluphenazine and its GABA conjugate AN 187. The obtained data show similar profiles of the prolactin blood level in the animals when treated with perphenazine, fluphenazine or with their GABA chemical conjugates, which peaked at 60 minutes and decreased thereafter. The prolactin blood levels, at each time point, in the animals treated with AN 168 and AN 187 were similar to those of perphenazine and fluphenazine, respectively.

FIG. 4a demonstrates the time course of the catalepsy induced by perphenazine and the chemical conjugates containing same, over a period of 7 hours. Catalepsy induced by perphenazine peaked after 2 hours and declined thereafter. The butyric acid-containing conjugate AN 167 induced reduced catalepsy as compared with perphenazine while the animals treated with the GABA-containing conjugate AN 168 had no catalepsy through the entire 7 hours period of the study.

FIG. 4b demonstrates the time course of the catalepsy induced by fluphenazine and the chemical conjugates containing same, over a period of 7 hours. The animals treated with fluphenazine displayed catalepsy during the measured 7 hours while those treated with AN 180 and AN 187 showed lower catalepsy. The catalepsy induced by AN 180 fluctuated during the measurement time while the catalepsy induced by AN 187 was abolished at the end of the 7-hours period. None of the animals in the study had catalepsy after 24 hours.

The effect of the administration of the tested compound on animals behavior was measured by evaluating the degree of animal sedation and mobility following the treatment described hereinabove, using a score of from 0 to 3. A score of 0 represents active and mobile animals, 1 represents calm and mobile animals, 2 represents calm and immobile animals and 3 represents completely ataxic and non-alert animals. The scores obtained are summarized in Table 2 below and demonstrate the reduced effect of the chemical conjugates on animal behavior as is compared with that of the known drugs.

TABLE 2

|  | 30 min | 60 min | 90 min | 120 min | 180 min | 240 min |
|---|---|---|---|---|---|---|
| Perphenazine | 1 | 2 | 2 | 3 | 2 | 2 |
| AN-167 | 0 | 1 | 1 | 2 | 2 | 2 |
| AN-168 | 0 | 0 | 1 | 1 | 1 | 1 |
| Fluphenazine | 1 | 2 | 3 | 3 | 2 | 2 |
| AN-180 | 1 | 2 | 3 | 2 | 1 | 1 |
| AN-187 | 1 | 2 | 2 | 2 | 1 | 1 |

Induced-catalepsy in rats by AN 168 and a mixture of perphenazine and GABA: The effect of AN 168, the GABA conjugate of perphenazine, on the catalepsy induced in rats was compared with the catalepsy induced by a mixture of its parent drugs—non-conjugated perphenazine and GABA. The catalepsy was measured at 60, 90 and 120 minutes following an intraperitoneal injection of the conjugate or the described mixture and was determined by the "wall" test.

FIG. 5a shows the data obtained for the total catalepsy induced by the various treatments. The animals in the group treated with AN 168 exhibited very low catalepsy while the catalepsy in the group treated with the mixture of perphenazine and GABA was high.

FIG. 5b shows the time course of catalepsy following both treatments and demonstrates reduced catalepsy in animals treated with AN 168, which is abolished after 120 minutes.

Catalepsy induced in rats by AN 167 and AN 168: The total catalepsy induced by AN 167 and AN 168 in four independent experiments was tested and compared with perphenazine-induced catalepsy under the same experimental conditions.

The average of total catalepsy following equimolar doses of AN 167 and AN 168, as percentage of the perphenazine-induced catalepsy, is shown in FIG. 6. Although AN 167 induced lower catalepsy as compared with perphenazine, AN 168 reduced the induced catalepsy to almost a zero value.

Induced-catalepsy in mice by perphenazine, a mixture of perphenazine and GABA and by AN 168: The effect of AN 168, the GABA conjugate of perphenazine, on the catalepsy induced in mice was compared with the catalepsy induced by perphenazine alone and by a mixture of the parent drugs—non-conjugated perphenazine and GABA. The catalepsy was measured at 60, 90 and 120 minutes following an intraperitoneal injection of the treatment, and was determined as described hereinabove.

FIG. 7a shows the data obtained for the catalepsy induced by the various treatments in terms of percentage of animals reaching the targets within 2 minutes. The animals in the group treated with AN 168 exhibited substantially lower disability while the animals in the groups treated with perphenazine alone and with a mixture of perphenazine and GABA exhibited higher catalepsy.

FIG. 7b shows the data obtained for the catalepsy induced by the various treatments, 2 and 3 hours following the above treatments, in terms of the time it took the animals to reach the target. The animals in the group treated with AN 168 were much faster than the animals treated with perphenazine alone and with a mixture of perphenazine and GABA.

Induced-catalepsy, induced animal behavior and psychotropic activity of orally administered perphenazine and its GABA conjugate AN 168: As AN 168, the chemical conjugate of perphenazine and GABA was found to be the presently most effective chemical conjugate when administered intraperitoneally, additional comparative experiments were performed in order to determine the oral efficacy of this chemical conjugate as compared with perphenazine. To this end, the induced catalepsy, the prolactin blood levels and the animal behavior were measured as described hereinabove, following oral administration of either AN 168 or perphenazine alone to rats. Animals, divided 5 per cage, were treated by oral administration of perphenazine or AN-168 dissolved in 1% lactic acid. Control animals received vehicle (lactic acid) only.

The catalepsy induced by oral administration of various concentrations of AN 168 and perphenazine was measured by the "wall" test and the "piano" test described hereinabove. The time course of catalepsy was measured 4-24 hours following oral administration of 2.5, 5, 10 and 20 mg/kg perphenazine and respective equimolar doses of 3.5, 7, 14 and 28 mg/kg AN-168. The total catalepsy represents the sum of average catalepsy per treated group during the 4-24 hours of follow-up.

FIG. 8a shows the time course of catalepsy following the various treatments, as measured by the "piano" test during 4-6 hours, and demonstrates the consistent reduction in the cataleptic behavior at all concentrations of AN 168. Statistical analysis indicated that the reduction was more significant ($p<0.05$) at the low and intermediate doses of AN 168 (7 and 14 mg/kg) as compared to their respective equimolar doses of perphenazine. At higher doses of the chemical conjugate (14 and 28 mg/kg) the detected cataleptic symptoms were consistently lower than those of perphenazine although the differences were less substantial. It is assumed though that these smaller differences between the catalepsy induced by the drug and the chemical conjugate at the higher doses result from the assessment procedure. Due to practical considerations, the maximal cataleptic signal measured was limited to 120 seconds. However, in reality, it is estimated that the maximum cataleptic signal induced by perphenazine is higher than the one elicited by the chemical conjugate. This estimation is further supported by the greater and substantial differences between AN-168 and perphenazine that were observed, at high doses, for both the catalepsy determined by the "wall" test and the sedation score, which are described hereinafter. Moreover, the experiments conducted showed that muscular rigidity and tachypnea were observed only in the animals treated with the intermediate and high doses of perphenazine (10 and 20 mg/kg) and not in the animals treated with the respective equimolar doses of the chemical conjugate.

FIG. 8b shows the time course of catalepsy following the various treatments, as measured by the "piano" test during 4-6 hours, in separate experiments conducted 3 months after the experiments presented in FIG. 8a. The obtained data indicate that at high doses of AN 168 (14 and 28 mg/kg), higher catalepsy was induces as compared with the proceeding experiments. NMR spectroscopy revealed that slow decomposition, probably due to hydrolysis, occurred and therefore the unique properties of the chemical conjugate were affected. These findings suggest that this compound should be stored in sealed vials and exposed only prior to use. It should be noted in this respect that the analogous chemical conjugate of fluphenazine, AN 187, does not appear to be hygroscopic and therefore does not tend to decompose upon a prolonged storage.

FIGS. 9a and 9b show the total catalepsy induced by the oral administration of 5, 10 and 20 mg/kg perphenazine and respective equimolar doses of 7, 14 and 28 mg/kg AN-168, observed during 4-6 hours. FIG. 9b presents the data obtained in experiments conducted 3 months after the experiments presented in FIG. 9a. Although the reduction in the cataleptic behavior induced by AN 168 as compared with perphenazine is less significant in the data presented in FIG. 9b, it is clearly shown that the catalepsy induced by AN 168 is consistently lower than that induced by perphenazine.

FIGS. 10a and 10b show the time course of catalepsy (FIG. 10a) and the total catalepsy (FIG. 10b) as measured by the "piano" test during 24 hours following the various treatments. The data obtained demonstrate that the maximal cataleptic effect of both perphenazine and AN-168 was achieved 5-6 hours following treatment and that 24 hours post-treatment the catalepsy was reduced in all treatment groups. These data are in line with the clinical time course observed for perphenazine administered to patients (once daily).

FIG. 11 shows the total catalepsy following the various treatments, as measured by the "wall" test and clearly demonstrates that the cataleptic symptoms were almost abolished following treatment with all the tested doses of AN 168.

The effect of the oral administration of the chemical conjugate AN 168 on animals behavior was measured by evaluating the degree of animal sedation and mobility, 4-6 hours following oral treatments with various concentrations of AN 168 and perphenazine, using a score of from 0 to 3, as is described hereinabove. The scores obtained are summarized in Table 3 below and demonstrate the reduced effect of the chemical conjugate on animal behavior as compared with perphenazine.

and AN 168. The prolactin blood levels, at each time point, in the animals treated with AN 168 were similar to those of perphenazine, at low and intermediate doses, while at a higher dose the prolactin blood level in the animals treated with AN 168 was much higher as compared with animals treated with perphenazine.

These results demonstrate that AN 168 is highly efficient, and therefore relevant to clinical use, at low doses (e.g., 3.5 and 7 mg/kg), when orally administered. It is further shown herein that at these low doses, AN 168 caused minimal extrapyramidal symptoms, and is therefore almost devoid of antagonistic activity at the nigro-striatal pathway.

Anti-proliferative activity: The anti-proliferative activity of perphenazine, the chemical conjugates thereof AN 167, AN 168 AND an 177, fluphenazine, the chemical conjugates thereof AN 179, AN 180, AN 181 and AN 187, and of butyric acid (BA), 4-phenylbutyric acid (PBA) and GABA was measured by proliferation tests performed (usually in more than one independent experiment) with normal and transformed cells. The cells were sub-cultured and the tested compounds were added thereto in increasing concentrations. The $IC_{50}$ values were determined by linear regression of the survival percentage of the cells. The $IC_{50}$ values obtained for the tested compounds with the various tested cell lines are summarized in Table 4 and Table 5 below.

TABLE 4

| Drugs | Cells | | | | | |
|---|---|---|---|---|---|---|
| | B16 MDR | B16 | HT-29 | PC-3 | 3T3 | Normal rat fibroblasts |
| Perphenazine | 18.45 ± 5.4 n = 3* | 12.5 ± 1.29 n = 4 | 8.85 ± 2.7 n = 4 | 23.1 ± 2.3 n = 2 | 26.6 | |
| BA | 8000 ± 546 n = 3 | 1300 ± 113 n = 3 | 7170 ± 2034 n = 4 | | | 5540 |
| GABA | >20000 n = 3 | >20000 n = 3 | >20000 n = 3 | | | >20000 |
| AN-167 | 41.5 ± 1.8 n = 3 | 17.3 ± 4.5 n = 5 | 13.3 ± 2.4 n = 4 | 49.1 | 21.7 | 31.64 |
| AN-168 | 23 ± 16 n = 3 | 26.8 ± 1.8 n = 3 | 23.1 ± 9 n = 3 | 45.5 | 25 | 45.8 |
| AN-130 | 58 | 36.5 ± 8.1 n = 5 | 17.27 ± 3.07 n = 5 | 52.9 ± 28.7 n = 3 | | 41.9 ± 16.8 n = 2 |
| AN-177 | | | 25.8 | | 24.6 | |
| AN-178 | | | 11.5 | | 18.6 | |

*Number of independent experiments.

TABLE 3

| Treatment | Dose (mg/kg) | Sedation score |
|---|---|---|
| perphenazine | 20 | 3 |
| perphenazine | 10 | 2 |
| perphenazine | 5 | 1 |
| perphenazine | 2.5 | 0 |
| AN 168 | 28 | 2 |
| AN 168 | 14 | 1 |
| AN 168 | 7 | 0 |
| AN 168 | 3.5 | 0 |
| control | | 0 |

As a marker for the dopaminergic activity of the orally administered compounds, the prolactin blood levels were measured 0, 90 and 180 minutes following the various treatments described hereinabove. The obtained data is summarized in FIG. 12 and demonstrate the similar profiles of the prolactin blood level in the animals treated with perphenazine

TABLE 5

| Drugs | Cells | | | | | |
|---|---|---|---|---|---|---|
| | HL 60 | HL 60 MX2 (MDR) | MES SA | MES SA DX5 (MDR) | JURKAT | U-937 |
| Perphenazine | 19.76 | 22.55 | 15.31 | 16.24 | 11.34 | 21.30 |
| AN 167 | 17.29 | 19.86 | 17.23 | 20.90 | 11.40 | 23.28 |
| AN 168 | 15.14 | 18.36 | 18.20 | 17.16 | 11.35 | 14.23 |
| AN 177 | 15.13 | 17.59 | | | | |
| Fluphenazine | 20.94 | 21.77 | 14.79 | 13.74 | 14.30 | 21.51 |
| AN 179 | 18.25 | 21.42 | | | | |
| AN 180 | 19.00 | 18.76 | 11.96 | 12.74 | 10.43 | 12.25 |
| AN 181 | 14.79 | 16.69 | | | | |
| AN-187 | 18.57 | 17.10 | 14.37 | 9.47 | 10.31 | 18.86 |

These results show that although GABA, by itself, fails to demonstrate a significant anti-proliferative activity ($IC_{50}$>20 mM), and BA ($IC_{50}$ range of 1-8 mM) and PBA ($IC_{50}$ range of 2-12 mM, data not shown) showed noticeable yet relatively low anti-proliferative activity, their respective perphenazine and fluphenazine conjugates had significantly higher activity ($IC_{50}$ range of 8-60 μM).

These results further demonstrate the versatile anti-proliferative activity of the chemical conjugates of the present invention in a wide variety of cell lines, including multidrug resistant (MDR) cells, such as HL 60 MX2, B 16 MDR subcolon and MES SA DX5.

FIG. 13 shows the results obtained in a representative experiment where the effect of perphenazine and the chemical conjugates thereof on the proliferation of B16 murine melanoma cells was measured. AN 167 and AN 168 were found to be relatively active as anti-proliferative drugs.

The cytotoxic effect of perphenazine, GABA and the chemical conjugate thereof AN 168, were measured and compared with the cytotoxic effect of the known chemotherapeutic drugs Cisplatin and Vincistine, on C6 rat glioma cells. The cells were sub-cultured and the tested compounds were added thereto in increasing concentrations, up to 100 μM. The cells viability following these treatments (24 hours) was determined by the neutral red method described hereinabove and the results are presented in FIG. 14. The $IC_{50}$ values of perphenazine and AN 168 were determined as described hereinabove, and were found to be 19.2 μM and 24.2 μM, respectively.

As is shown in FIG. 14, the obtained data demonstrates the superior anti-proliferative activity of the chemical conjugates of the present invention, as compared with representative known chemotherapeutic drugs. C6 glioma cells are known as MDR cells, and indeed, the anti-proliferative activity of the known chemotherapeutic drugs was found to be substantially low. In contrast, AN 168 was found to exert high anti-proliferative activity, causing substantial cell death at relatively low concentrations (about 20 μM).

FIG. 15 presents the data obtained following treatment of Jurkat T lymphoma cells with increasing concentrations of perphenazine, AN 168 and Dexamethasone. The results are presented in terms of cells viability, determined by the alamar blue method, and demonstrate the superior cytotoxic effect of AN 168 and perphenazine, as compared with Dexamethasone. The $IC_{50}$ values of perphenazine and AN 168 were 16 μM and 19 μM, respectively.

It should be further noted that although perphenazine, fluphenazine and their chemical conjugates exert anti-proliferative activity to about the same extent, the clinical use of the chemical conjugates of the present invention is highly superior over the clinical use of the neuroleptic drugs, as the administration of the chemical conjugates is almost completely devoid of adverse side effects.

Chemosensitizing effect by co-administration of perphenazine or AN 168 and chemotherapeutic drugs: The chemosensitizing effects of 5, 10 and 15 μM perphenazine and equimolar doses of its chemical conjugate AN 168 were measured by co-administering these compounds with varying concentrations of known chemotherapeutic drugs such as Vincistine, Cisplatin and Dexamethasone. The cells viability and/or the DNA fragmentation, determined as described hereinabove in the methods section, following these combined treatments was compared with the results obtained following treatments with the chemotherapeutic drug alone.

FIG. 16 presents the data obtained following 24 hours treatment of rat C6 glioma cell line (MDR cells) with Vincistine (30 μM), perphenazine, AN 168 and combinations thereof. The results clearly demonstrate the chemosensitizing effect of AN 168, which, when co-administered with the chemotherapeutic drug, substantially enhance the cytotoxic effect thereof, even at low concentrations of the chemical conjugate (e.g., 5 μM), as compared with the cytotoxic activity of the drug when administered alone.

FIG. 17 presents the data obtained following treatment of rat C6 glioma cell line (MDR cells) with Cisplatin at various concentrations ranging between 5 μM and 50 μM, and with a combination of Cisplatin and 10 and 15 μM of AN 168. The results are presented in terms of cells viability, measured by the neutral red method, and clearly demonstrate that while the cells were completely resistant to Cisplatin at all the tested concentrations, the combined treatment of Cisplatin and AN 168 rendered the cells susceptible to the chemotherapeutic drug.

FIG. 18 presents the DNA fragmentation data obtained following treatment of rat C6 glioma cells with Cisplatin (30 μM), perphenazine (25 and 50 μM), AN 168 (25, 50 μM), a combination of Cisplatin (30 μM) and AN 168 (50 μM), compared with untreated cells. The DNA fragmentation was determined by the propidium iodide flow cytometric method described hereinabove. The results demonstrate that while Cisplatin alone has no effect of DNA fragmentation, perphenazine and AN 168 both induced a dramatically increase in DNA fragmentation. These results suggest that the chemosensitizing effect of the chemical conjugates of the present invention results from this activity thereof.

Toxicity: The in vitro toxicity of perphenazine, AN 167 and AN 168 was measured on primary cultures of neuronal cells and a mixture of neuronal and glial cells, obtained from neonatal mouse brains. The cell cultures were treated with the tested compounds for 24 hours and their viability was determined thereafter by the neutral red colorimetric test. The $IC_{50}$ values obtained in these tests demonstrate that perphenazine and AN 167 had similar toxicity while AN 168 exhibited significantly lower toxicity toward normal brain cells, as shown in FIG. 19. The in vitro toxicity of perphenazine and AN 168 was further measured on cultured rat myocytes. FIG. 20 presents the cells viability, determined as described hereinabove, following treatment with various concentrations of perphenazine or AN 168. The obtained data show that AN 168 did not cause any decrease in cells viability at all concentrations, while perphenazine caused a 20% decrease in cells viability at high concentrations.

The in vivo toxicity of perphenazine and AN 167 was evaluated following the intraperitoneal administration of a single dose thereof to mice. The $LD_{50}$ values, determined two weeks following the treatment, were 109 mg/kg for perphenazine and 120 mg/kg for AN 167. In addition to the lower toxicity of AN 167 compared with perphenazine (per), the mortality caused by the conjugated compound was delayed, as shown in FIG. 21.

D-Amphetamine-induced hyperactivity in rats: The efficacy of the chemical conjugates of the present invention was studied using the D-amphetamine-induced hyperactivity and motility model. This model has the advantage of being a predictive and reproducible model for the selection of compounds that have anti-psychotic activity in amphetamine-associated disorders such as schizophrenia[14]. Using this model, the efficacy of a chemical conjugate of perphenazine and GABA, AN-168, was studied and compared with that of the parent compounds, perphenazine and GABA, administered alone.

Thus, naïve Wistar male rats were divided into several groups, each group was treated, 90 minutes prior to intraperitoneal administration of 2.5 mg/kg amphetamine, by intraperitoneal administration of a certain concentration of perphenazine (0.5, 1.5 or 3 mg/kg) a certain concentration of AN-168 (0.5 or 1.5 mg/kg), of 5 mg/kg GABA or of 1.5 mg/kg perphenazine and 5 mg/kg GABA. The climbing behavior of the rats in each group was measured as described hereinabove.

As is shown in FIGS. 22 and 23, AN-168 completely antagonized the climbing behavior induced by amphetamine even at low doses, thereby demonstrating its high and superior psychotropic efficacy, as compared with its parent drugs perphenazine and GABA.

However, as is shown in FIGS. 24 and 25, the effect of AN-168 in reducing head movements and other small body movement was inferior to that of perphenazine. It is believed that this inferiority results from the reduced extrapyramidal side effects, namely cataleptic symptoms and sedation, induced by the conjugate AN-168, as compared with the parent perphenazine. As is further shown in FIGS. 22-25, the administration of GABA alone did not modify the effect of amphetamine, neither it changed the effect of perphenazine, thereby suggesting that the enhanced efficacy and the reduced adverse side effects results from the administration of the conjugate AN-168.

As is shown in FIGS. 26-28, similar results were obtained when 2.5 mg/kg perphenazine, alone or in combination with 5 mg/kg GABA, and 3.5 mg/kg AN-168 were orally administered to rats, 90 minutes prior to intraperitoneal administration of amphetamine, demonstrating the superior efficacy of the conjugate in versatile administration routes.

The efficacy of AN-168 was further compared with that of olanzapine, a known atypical anti-psychotic drug. Various concentrations of olanzapine (2.5, 5 or 10 mg/kg) of olanzapine were orally administered to rats, followed by intraperitoneal administration of amphetamine. As is shown in FIGS. 29-31, while olanzapine was capable of substantially antagonizing the climbing behavior induced by amphetamine only at high doses (10 mg/kg), almost no effect thereof was observed with respect to head movements.

These results stand in line with the previously reported lower efficacy of olanzapine in the amphetamine model [15]. However, the data obtained in these studies further suggest that the chemical conjugates of the present invention exert lower anti-dopaminergic activity, as compared with neuroleptic drugs and therefore may show some resembles to atypical drugs.

The data obtained in this model further support the high efficacy of the conjugates of the present invention in exerting psychotropic activity while reducing the adverse side effects induced by the parent psychotropic drug.

The overall experimental results delineated hereinabove demonstrate the high and advantageous efficacy of the novel chemical conjugates of the present invention in exerting psychotropic activity, anti-proliferative activity and chemosensitizing activity, with minimized toxicity to normal cells and minimized adverse side effects.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Additional References are Cited in the Text

1. Lloyd K G, Morselli P L, Depoortere H, Fournier V, Zivkovic B, Scatton B, Broekkamp C, Worms P, Bartholini G. The potential use of GABA agonists in psychiatric disorders: evidence from studies with progabide in animal models and clinical trials. *Pharmacol. Biochem. Behav.* 1983, 18, 957-66.
2. Capasso A, Biondi A, Palagiano F, Bonina F P, Montenegro L, de Caprariis P, Pistorio E, Sorrentino L. Anticonvulsive activity of a new GABA mimetic drug. *Eur. Neuropsychopharmacol.* 1997, 7, 57-63.
3. Toth I. A novel chemical approach to drug delivery: lipid amino conjugates. *J Drug Target.* 1994, 2, 217-39.
4. Nordenberg J, Fenig E, Landau M, Weizman R, Weizman A. Effects of psychotropic drugs on cell proliferation and differentiation. *Biochem. Pharmacol.* 1999 58, 1229-369.
5. a) Prasad K N. Butyric acid: A small fatty acid with diverse biological functions. *Life Sci* 1980, 27, 1351-1358. b) Kruh J. Effects of sodium butyrate, a new pharmacological agent, on cells in culture. *Mol. Cell. Biochem.* 1982, 42, 65-82.
6. Wolffe A. Transcriptional control. Sinful repression. *Nature* 1997, 387, 16-17.
7. Shalitin N, Friedman M, Schlesinger H, Barhum Y, Levy M J, Schaper W, Kessler-Icekson G. The effect of angiotensin II on myosin heavy chain expression in cultured myocardial cells. *In Vitro Cell Dev. Biol. Anim.* 1996, 32, 573-8.
8. Kopf-Maier P, Kolon B. An organoid culture assay (OCA) for determining the drug sensitivity of human tumor. *Int. J. Cancer* 1992, 51, 99-107.
9. Mc Cafferty T A, et al. *In Vitro Cellular Develop. Biol.,* 1988, 24, 247.
10. Worms P, Kan J P, Wermuth C G, Biziere K. Dopamine-like activities of an aminopyridazine derivative, CM 30366: a behavioural study. *Naunyn Schmiedebergs Arch Pharmacol* 1986, 334, 246-5.
11. a) Pieron C., Effect of centrally acting drugs on serum prolactin levels in rhesus monkeys. *Neuroendocrinology,* 1978, 27, 136-47; b) Rubin R T. Prolactin and schizophrenia in: Psychopharmacology The Third Generation of Progress. *Meitzer HI* (Ed) New York; Raven Press 1987, 803-8.
12. a) Yale L H, Sowinski F A, Bernstaein J. Trifluoromethylphenothiazines. U.S. Pat. No. 3,227,708, Jan. 4, 1966; b) Buus J L M, Lassen N. Phenothiazine derivatives, compositions thereof and methods of preparation thereof. U.S. Pat. No. 3,966,930, Jun. 29, 1976.
13. Nicolletti I., Migliorato G., Pagliacci M. C., Grimsani F., and Riccardi C: A rapid and simple method for measuring thymocyte apoptosis by propidium—iodide staining and flow cytometry. *J Immunol. Methods,* 139, 271-79 1991.
14. Pouzet B., Didriksen M., Arnt J. Effects of the 5-HT(7) receptor antagonist SB-258741 in animal models for schizophrenia. *Pharmacol. Biochem. Behav.* 2002, 71(4), 655-65.

15. Geyer M. A., Ellenbroek B. Animal behavior models of the mechanisms underlying antipsychotic atypicality. Progress in *Neuropsychopharmacol & Biological Psychiatry.* 2003, 27, 1071-9.

What is claimed is:

1. A compound being fluphenazine 4-aminobutyrate or a trihydrochloride salt thereof.

2. A pharmaceutical composition comprising, as an active ingredient, the compound of claim 1 and a pharmaceutically acceptable carrier.

3. The pharmaceutical composition of claim 2, being packaged in a packaging material and identified in print, on or in said packaging material, for use in the treatment of schizophrenia.

4. A method of treating schizophrenia in a subject, the method comprising administering to the subject a therapeutically effective amount of the chemical conjugate of claim 1.

5. The method of claim 4, wherein said chemical conjugate is administered intraperitoneally.

6. The method of claim 4, wherein said chemical conjugate is administered orally.

7. A method of synthesizing the chemical conjugate of claim 1, the method comprising:
reacting γ-aminobutyric acid and fluphenazine, so as to obtain fluphenazine 4-aminobutyrate or a trihydrochloride salt thereof.

8. The method of claim 7, further comprising:
protecting the amino group of γ-aminobutyric acid with a protecting group, prior to said reacting, so as to obtain by said reacting an amino-protected fluphenazine 4-aminobutyrate or a trihydrochloride salt thereof; and
removing said protecting group after obtaining said amino-protected fluphenazine 4-aminobutyrate or a trihydrochloride salt thereof.

* * * * *